United States Patent [19]

Yamamoto et al.

[11] Patent Number: 5,624,798
[45] Date of Patent: Apr. 29, 1997

[54] DETECTION METHOD OF NUCLEIC ACID BY USE OF FLUORESCENT PYRYLIUM STAIN IN INTERCALATION INTO NUCLEIC ACIDS

[75] Inventors: Nobuko Yamamoto, Isehara; Tadashi Okamoto, Yokohama; Yoshinori Tomida, Atsugi; Takeshi Miyazaki, Ebina; Masahiro Kawaguchi, Atsugi, all of Japan

[73] Assignee: Canon Kabushiki Kaisha, Tokyo, Japan

[21] Appl. No.: 170,689

[22] Filed: Dec. 21, 1993

[30] Foreign Application Priority Data

| Dec. 21, 1992 | [JP] | Japan | 4-340755 |
| Mar. 10, 1993 | [JP] | Japan | 5-49530 |
| Sep. 13, 1993 | [JP] | Japan | 5-227204 |
| Oct. 26, 1993 | [JP] | Japan | 5-266866 |
| Dec. 17, 1993 | [JP] | Japan | 5-318045 |

[51] Int. Cl.$^6$ .............. C12Q 1/68; D06P 5/00; C07D 335/00; C07D 309/00
[52] U.S. Cl. .................. 435/6; 8/506; 549/13; 549/28; 549/356; 549/424
[58] Field of Search ............ 424/3, 7.1; 8/506; 549/13, 28, 356, 424

[56] References Cited

U.S. PATENT DOCUMENTS

| 3,786,369 | 1/1974 | Drexhage et al. | 331/94.5 |
| 4,341,894 | 7/1982 | Regan et al. | 544/333 |
| 4,555,396 | 11/1985 | Frank et al. | 424/3 |
| 4,840,784 | 6/1989 | Frank et al. | 434/3 |
| 5,229,297 | 7/1993 | Schnipelsky et al. | 436/94 |

FOREIGN PATENT DOCUMENTS

| 229943 | 12/1986 | European Pat. Off. | C12Q 1/68 |
| 232967 | 1/1987 | European Pat. Off. | C12Q 1/68 |
| 320308 | 12/1988 | European Pat. Off. | C12Q 1/68 |
| 0315491 | 5/1989 | European Pat. Off. | |
| 439036 | 1/1991 | European Pat. Off. | C12Q 1/68 |
| 487218 | 10/1991 | European Pat. Off. | C12Q 1/68 |
| 455517 | 11/1991 | European Pat. Off. | C12Q 1/68 |
| 512334 | 4/1992 | European Pat. Off. | C12Q 1/68 |
| WO8603227 | 6/1986 | WIPO | C12Q 1/68 |
| WO8910415 | 11/1989 | WIPO | C12Q 1/68 |

OTHER PUBLICATIONS

Morrison et al., "Solution Phase Detection of Polynucleotides Using Interacting Fluorescent Labels and Competitive Hybridization", *Analytical Biochem.*, 183, 231–244 (1989).

C. Picard et al., "Detection and Enumeration of Bacteria in Soil by Direct DNA Extraction an Polymerase Chain Reaction", *Appl. and Env. Microbio.*, 58, 9, 2717–22 (1992).

D. Basting et al., "New Laser Dyes", *Appl. Phys.*, 3, 81–88 (1974).

O. Strobel et al., "Preparation and Characterization of Spin-Labeled Oligonucleotides for DNA Hybridization", *Bioconjugate Chem.*, 1991, 2, 89–95 (1991).

A. Rahman et al., "Complexes involving quercetin, DNA and Cu(II)", *Carcinogenesis*, 11, 11, 2001–03 (1990).

P. Fromherz et al., "Photoinduced Electron Transfer in DNA Matrix from Intercalated Ethidium to Condensed Methylviologen", *J. Am. Chem. Soc.*, 108, 5361–62 (1986).

J. Barton et al., "DNA-Mediated Photoelectron Transfer Reactions", *J. Am. Chem. Soc.*, 108, 6391–6393 (1986).

A. Brun et al., "Dynamics of Electron Transfer between Intercalated Polycyclic Molecules: Effect of Interspersed Bases", *J. Am. Chem. Soc.*, 114, 3656–60 (1986).

P. Cullis et al., "Electron Conduction and Trapping in DNA—An Electron Spin Resonance Study", *J. Chem. Soc.—Faraday Trans.*, 86(3), 591–92 (1990).

T. Shimidzu et al., "Synthesis of oligonucleotide derivatives with P(V) porphyrin and their properties", *Nucleic Acids Symp. Ser.*, vol. 27, 97–98 (1992).

R. Cardullo et al., "Detection of nucleic acid hybridization by nonradiative fluorescence resonance energy transfer", *Proc. Natl. Acad. Sci.*, 8790–94 (1988).

M. Purugganan et al., "Accelerated Electron Transfer Between Metal Complexes Mediated by DNA", *Science*, 241, 23 Sep. 1988, 1645–49.

C. Murphy et al., "Long-Range Photoinduced Electron Transfer Through a DNA Helix", *Science*, 262, 12 Nov.n 1993, 1625–29.

Yamamoto et al, (1993), "Novel intercalators of pyrylium dye into double-stranded DNA" Nucleic Acids Symposium Series No. 29 pp. 83–84.

Detty et al, (1987), "Rational design of properties in chalcogenapyrylium dyes" In SPIE vol 847 New Directions in Photodynamic Therapy, D. Neckers Ed. pp. 68–73.

Balaban et al, (1982), "Regioselective deuteriation kinetics of 2-, 4-, and 6-methyl groups in $D_2O$ solutions of pyrylium and N-methyl pyridinium perchlorates possessing also 3-methyl or 3-phenyl groups" J. Labelled Compounds and Radiopharmaceuticals 19(6):783–793.

(List continued on next page.)

*Primary Examiner*—Stephanie W. Zitomer
*Assistant Examiner*—Jeffrey Fredman
*Attorney, Agent, or Firm*—Fitzpatrick, Cella, Harper & Scinto

[57] ABSTRACT

A stain for a nucleic acid characterized by containing, as an effective component, a pyrylium salt compound having Y as a negative portion and a pyrylium ring or a pyrylium-similar ring, wherein the ring is comprised of X selected from O, S, Se and Te as a hetero atom and has substituents $R^1$, $R^2$ and $R^3$, wherein each of $R^1$ and $R^2$ is independently a hydrogen atom, sulfonate group, amino group, substituted or unsubstituted aryl group, etc., $R^3$ is -A or -L-A, L is -$L^1$-, -$L^2$-$L^3$- or -$L^4$-$L^5$-$L^6$-, and each of $L^1$ to $L^6$ is independently —(CH=CH)—, a divalent group derived from the substituted or unsubstituted aryl group, etc., A is a substituted or unsubstituted aryl group, etc., and $Y^-$ is an anion. A method for detecting a nucleic acid which comprises the steps of reacting a sample with the stain, and then detecting, by an optical means, the double-strand nucleic acid stained with the stain in the case that the double-strand nucleic acid is contained in the sample.

32 Claims, 11 Drawing Sheets

OTHER PUBLICATIONS

Detty et al, (1990), "Chalcogenapyrylium dyes as photochemotherapeutic agents. 2. tumor uptake, mitochondrial targeting, and singlet oxygen induced inhibition of cytochrome c oxidase", J. Med. Chem. 33:1108–1116.

K.K. Sanford, et al., *Journal of the National Cancer Institute,* Dec. 1948, pp. 229–246.

S.A. Latt et al., "New Fluorochromes . . . ", Jour. Soc. Analyt. Cytology, vol. 5, No. 4, Jul. 1984, pp. 339–347.

D. Basting et al., "New Laser Dyes", Applied Physics, vol. 3, 1974, pp. 81–88.

G. Haucke et al., "Absorption and Fluorescence of Pyrylium Salts", Ber. Bunsenges, Phys. Chem., vol. 96, No. 7, 1992, pp. 880–886.

Blasko et al, "Approaches to the synthesis of benzo[c] phenanthridines", J. Heterocycl. Chem. 26(6):1601–3 Abstract Only. 1989.

Chatterjea et al, "Synthesis of 2-phenyl [1,2-b] naphthopyrylium salts: a study of michael reactions with 1-naphthol", Natl. Acad. Sci. Lett. (India) 11(10):311–12. Abstract Only. 1988.

Tilak et al, "Synthesis of sulfur heterocyclics. X. mono-and dicationoid heterocyclic systems containing one and two sulfur atoms", Indian J. Chem. 7(10):948–51. Abstract Only. 1969.

Bringmann et al, "Novel concepts in directed biaryl synthesis. XXXVIII Synthesis and structure of a protected lactolate bridged biaryl with relevance to the atropisomer-selective ring opening of biaryl lactones", Liebigs Ann. Chem. (4):439–44. Abstract On 1994.

DETECTION METHOD OF NUCLEIC ACID BY USE OF FLUORESCENT PYRYLIUM STAIN IN INTERCALATION INTO NUCLEIC ACIDS

BACKGROUND OF THE INVENTION

1. Field of the Invention

The present invention relates to a novel pyrylium salt useful for the detection of a nucleic acid by the use of an optical means. It also relates to a stain containing a pyrylium salt for use in the detection of a nucleic acid by the use of an optical means, and a detection method of a nucleic acid by the use of the stain. Furthermore, it relates to a stain for a nucleic acid containing a pyrylium salt useful for the detection of a hybrid by a hybridization method using a probe for the detection of a variation at a nucleic acid level, and a detection method of a nucleic acid by a hybridization method using the stain for the nucleic acid.

The present invention also relates to a staining method and an observation method for microorganisms such as bacteria, yeast, mold, algae and protozoan as well as cells, a tissue and a chromosome of an animal and a plant. In addition, it relates to a detection method of a nucleic acid by an in situ hybridization using a probe containing a pyrylium salt as a label for the detection and identification of a specific sequence of the nucleic acid in biological samples.

2. Related Background Art

As modes by which a substance can interact with the double helix of DNA, there are known a case where the substance Gets into the base pair of a nucleic acid as an intercalater, a case where the substance is buried in grooves of the double helix, and a case where the substance approaches so as to be contiguous with the double helix.

The above-mentioned intercalater is usually a lamellar compound having a spread electron cloud, and it is arranged on an extended line of the stacked base pairs of the nucleic acid, i.e., on the axis of the double helix at the same distance as the distance between the base pairs of the nucleic acid in parallel with the base pairs of the nucleic acid. When intercalated in DNA, the intercalater characteristically leads to the fact that an optical absorption spectrum shifts to a longer wavelength side, absorption intensity decreases, or fluorescent intensity increases. For example, a dyestuff, in which the fluorescent intensity increases more in the case that the interaction with DNA takes place (when intercalated) than in the case that the interaction with DNA of a free state or the like does not occur, is used for the various detection operations of the nucleic acids such as agarose gel electrophoresis by the utilization of its characteristics.

Examples of a well-known intercalater include acridine orange, proflavine, ethidium bromide, donomycin and actinomycin. In particular, ethidium bromide and acridine orange are well known.

However, most of these dyestuffs have excitation wavelengths in an ultraviolet region, and hence an intensive ultraviolet lamp must be used, so that special care is required in order to protect persons from the lamp. For example, at the time of the detection of DNA, some equipment is required to protect the eyes and skin of an operator from the ultraviolet rays, and such equipment is on the market. Furthermore, in order to take the photographs of the electrophoresis patterns of DNA, a device such as a transilluminator is usually used, but the exposure adjustment of a camera in this case cannot be directly seen by the naked eye and so it is an intricate operation of trial and error. Moreover, in the case that the cutting of DNA from the agarose gel is directly seen by the naked eye, the operator cannot be completely protected from the irradiation with the ultraviolet rays even by the employment of the protective equipment. In addition, in the detection of DNA in the state of a liquid by the utilization of the dyestuff which can be excited by the ultraviolet rays, the irradiation of the intensive ultraviolet is always continuously given, so that harmful ozone and the like are also generated. In a certain case, DNA itself might be damaged by the ultraviolet irradiation. Much attention is being paid to an in situ hybridization in which hybridization is carried out in live cells to detect the live cells, but in the case that the dyestuff which can be excited by the ultraviolet rays is used as a label, the cells themselves are damaged by the ultraviolet radiation for the detection on occasion.

On the other hand, in the fields of medicine, biology and the like, biological specimens of microorganisms, human cells or animal cells are observed by a microscope or another means for the purpose of research, diagnosis and the like, but for such an observation, staining is usually widely carried out. Staining methods which can be utilized in such a purpose can usually be classified roughly into two categories. In the first category, there is a staining method in which a specific component which can be utilized for the staining of a portion to be observed and present in the biological specimen is stained with a dyestuff. As principles of the staining, there are a case where a target is stained with the dyestuff itself and a case where a coloring component is deposited on the present position of a specific component through various chemical reactions. They can often be used for pathological tests, and various staining methods have been conceived for various target components. These staining methods mainly intend to make visible a specific component, a specific morphology or a specific region, and they are often used for the observation of relatively macroscopic targets.

On the contrary, the staining method of the second category is called a fluorescent staining method. In the fundamental operation of the fluorescent staining method, a fluorescent dyestuff is first introduced into a present site of a specific component to be stained. As an introduction technique, there is a case where a target specific affinity of the dyestuff itself is utilized (the staining of an nucleic acid with ethidium bromide), and a case where a substance having a target specificity such as an antibody is bonded to the dyestuff, and its specific affinity is utilized to introduce the dyestuff into the target to be stained. These fluorescent staining methods are often used in a research field such as biology. In the fluorescent staining method in which the target to be observed is fluorescent, the detection sensitivity of a signal is high, and precision is also higher than the above-mentioned staining method by the coloring, and the microscopic targets can be handled. In general, the main purpose of the fluorescent staining method is often to detect a specific component.

In either method of the usual staining method and the fluorescent staining method, the specimen which is the target to be stained such as cells is usually fixed with an aldehyde or the like prior to the staining. This has the effect of improving the permeability of the dyestuff for use in the staining or another reagent into the specimen, and the effect of preventing the specimen from breaking during various operations necessary for the staining. Furthermore, in addition to the fixing operation and the staining operation, a washing operation is required to remove the excessive dyestuff, reagent and the like. This is essential to decrease background and to obtain stable results at the time of the staining.

On the other hand, in recent years, as carcinogenesis mechanism and the metastasis mechanism of cancers have been elucidated, it becomes known that the translocation of a chromosome and the deletion of the chromosome are closely concerned with these mechanisms. That is, cellular cancer genes are those which take part in the adjustment of reception, transmission or transcription of a growth signal in normal cells, and it has been elucidated that the genes are activated as the cancer genes by the mutation or the abnormal amplification of this gene, the translocation of this gene to the neighborhood of the gene being vigorously transcribed, or the bond to another gene. Furthermore, it is considered that the deletion of a cancer inhibitory gene from the chromosome is also concerned with the carcinogenesis mechanism. In addition, also in various kinds of hereditary diseases, the gene deletion and the translocation have been made apparent. As described above, if the diagnosis by the detection of the abnormal gene at a chromosome level is possible, the growth of tumor can be inhibited by transfecting the normal chromosome into the abnormal chromosome, and the possibility of the remedy of the cancer and the hereditary disease by compensating the detection of the gene can also be expanded.

As a method for knowing the abnormal chromosome, there is FISH (fluorescence in situ hybridization). This method comprises observing a formation ability of a hybrid of a probe corresponding to a gene to be inspected and a gene of the chromosome, and at present, it is considered to be the most accurate method. In this method, the gene to be inspected is limited by the probe to be used, and so when the target to be detected is definite, this method can be directly utilized. However, in the case that it is intended to screen the whole chromosome, this method is not always suitable. Thus, the whole chromosome may be first checked, and sites, where abnormalities such as translocation presumable from an abnormal conformation or deletion presumable from an abnormal length takes place, may be then screened to focus the target on the abnormal site. Afterward, FISH can be utilized, whereby the precise genetic diagnosis is considered to be possible in a wide range.

In order to carry out such a screening, it is necessary to beforehand distinguish or identify the chromosome. As the distinction or the identification method of the chromosome, a differential staining method of the chromosome is utilized. The distinction of the chromosome by this differential staining method utilizes the fact that when the chromosome is dyed in a band state by the use of a specific dye or fluorescent dyestuff after various pretreatments, the relation between its distribution and density is constant for each chromosome and characteristics in each chromosome. This technique is utilized for the distinction of the chromosome or the detection of an abnormality.

As the usual differential staining method of the chromosome, there are known, for example, Giemsa staining (G band), quinacrine staining (Q band) and R band staining. In the Giemsa staining method, the strain of the higher-order structure of the chromosome which is caused by a trypsin treatment is differentiated and observed as the loose state of the chromosome. Furthermore, according to the staining with quinacrine which is a fluorescent dyestuff, the chromosome is stained in a deep and light striped pattern along its vertical axis, and this can be observed by a fluorescent microscope. This fluorescent pattern is inherent in each chromosome, and so the distinction or the identification of the chromosome can be achieved by this. The portion stained with quinacrine is a position where A-T pairs are rich, and the quinacrine staining is different from the above-mentioned Giemsa staining in a stained state. In the R band staining, chromomycin $A_3$ which is a fluorescent dyestuff is bonded to G-C pairs, and then treated with distamycin A which is a non-fluorescent dyestuff specific to the A-T pairs. In this case, a portion where G-C pairs are rich is only stained in the form of an R band, and the staining is characteristically carried out in a deep and light state opposite to the Q band staining and the G band staining. In the Q band staining and the R band staining of these differential staining methods, the detection sensitivity of a signal is higher as compared with the G band staining method by a coloring method, and they are also effective to handle a more precise microscopic target.

In this differential staining method of the chromosome, the more precise distinction or identification of the chromosome becomes possible by increasing the kinds of stains specific to sites of the chromosome, and so it is important for the more precise distinction or identification of the chromosome to develop the stain for permitting the differential staining specific to a different site, in addition to the already existent reagents (stains) for the differential staining.

On the other hand, many salts of pyrylium or thiopyrylium compounds in which the 2, 4 and 6-positions of a pyrylium ring or a thiopyrylium ring are substituted by substituted or unsubstituted phenyl groups have been suggested. Most of these salts are desirable as recording media, and for example, the specification of U.S. Pat. No. 4,341,894 describes that they are useful as sensitizers for electrical photoconductive compositions. In a biological field, it is described in Japanese Patent Application Laid-open No. 59-133460 that a 2,4,6-triphenylpyrylium or thiopyrylium compound, or a compound in which one of the phenyl groups substituted on the pyrylium ring or the thiopyrylium ring of this compound is replaced with a substituted styryl group is used as a stain for staining cells in a biological specimen. Furthermore, in Japanese Patent Application Laid-open No. 1-153683, it is described that a compound in which at least two of these phenyl-substituted groups have amino groups has a good efficacy for the remedy of a cancer.

When a dyestuff having an excitation wavelength in an ultraviolet region is used for the detection of a nucleic acid, the above-mentioned problems take place, and therefore as a means for avoiding these problems, it can be considered to use a dyestuff which can be excited by visible light. However, in most of the visible light excitation type dyestuffs which have been now utilized for the staining the nucleic acid, stokes shift is as slight as 20–30 nm, and so they have the drawback that an a signal to noise (S/N) ratio is bad at the time of the detection. As employed herein "S/N" means signal to noise ratio.

In an agarose gel electrophoresis or the like, when the degree of the increase of fluorescent intensity at the time of interaction with a nucleic acid is larger as compared with a case of no interaction with the double stand nucleic acid, the S/N ratio at the detection is good and it is possible to enhance detection sensitivity. However, the visible light excitation type dyestuffs which can sufficiently increase the fluorescent intensity are not known at present.

As described above, in order to solve the problems which the ultraviolet excitation type dyestuffs have, the visible light excitation type dyestuffs have been largely desired which has the large stokes shift and the much higher fluorescent intensity at the interaction with the nucleic acid as compared with the case of no interaction.

Moreover, in the conventional staining method of biological specimen such as cells, operations such as the fixation of the specimen by the use of formaldehyde or the like and the washing/removal of the excessive dyestuff are essential to obtain reproducible and stable results.

For example, the operation of the specimen fixation is important to improve the permeability of reagents of the dyestuff and the like or to maintain the morphology of the obtained specimen. In addition, the dyestuff for the staining, another reagent and the like are usually used in large excess of the specimen. This has effects of the curtailment of an operation (staining) time and the like but simultaneously causes the high background. Therefore, the washing operation between the respective operations is important to decrease the background at the time of observation or measurement and to thereby obtain a more correct judgement. For these reasons, the washing operation has been elaborately carried out. However, these operations are intricate and take much time, and hence in the case that a large amount of the specimens are treated, they interfere with a prompt treatment operation.

Therefore, the omission or simplification of operations such as the fixation and the washing of the specimens which are intricate and take much time are strongly desired.

Moreover, most of the fluorescent dyestuffs which have been heretofore used give rise to a vigorous fade phenomenon, and after the irradiation of the excitation light, the fluorescence rapidly disappears. Accordingly, contrary to the usual staining, it is difficult to observe a fluorescent image for a long period of time, and the preparation of the permanent specimen by the fluorescence staining is almost impossible. For these reasons, it is a desired to develop a preparation method of the fluorescence-stained specimens which can be stored for a long period of time.

In the field of the differential staining of the chromosome, a stain which can obtain a stained pattern different from that given by the conventional stain is highly desired, as described above. In addition, as in the case of the above-mentioned staining of the biological specimen, also in the differential staining of a chromosome, operations such as the fixation of the specimen by aldehyde and the washing of the excessive stain take time and equipment, and they interfere with the prompt achievement of a treatment such as mass screening of a large amount of the specimens.

SUMMARY OF THE INVENTION

Thus, an object of the present invention is to provide a stain for a nucleic acid containing, as an effective component, a visible light excitation type dyestuff giving a large stokes shift and having a much higher fluorescent intensity at the time of interaction with the nucleic acid, as compared with the state of no interaction.

Another object of the present invention is to provide a detection method of a nucleic acid by the use of the stain.

Still another object of the present invention is to provide a 2-methyl-4,6-bis-(4-N,N-dimethylamino)pyrylium or thiopyrylium salt which is useful as an effective component of the stain for the nucleic acid.

A further object of the present invention is to provide a staining method or a differential staining method which permits reproducible and stable staining and the prompt treatment of a large number of specimens.

A still further object of the present invention is to provide a differential staining method for a chromosome which can give a differential staining pattern different from that by a known stain.

A still further object of the present invention is to provide a fluorescence staining method or a differential staining method for preparing storage specimens in which stained portions neither fade nor disappear.

These objects can be achieved by the present invention.

The first aspect of the present invention is directed to a stain for a nucleic acid characterized by containing, as an effective component, a compound represented by the formula [I]

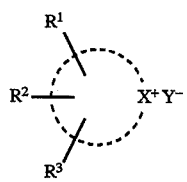

wherein

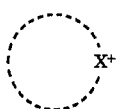

is a heterocyclic ring, and X is O, S, Se or Te, and it is a pyrylium ring and a pyrylium-similar ring, each of $R^1$ and $R^2$ is independently a hydrogen atom, halogen atom, sulfonate group, amino group, styryl group, nitro group, hydroxyl group, carboxyl group, cyano group, substituted or unsubstituted lower alkyl group, substituted or unsubstituted aryl group, substituted or unsubstituted lower aralkyl group, or substituted or unsubstituted cycloalkyl group, $R^3$ is —A or —L—A, L is —$L^1$, —$L^2$—$L^3$— or —$L^4$—$L^5$—$L^6$—, and each of $L^1$ to $L^6$ is independently —(CH=CH)—, a divalent group derived from the substituted or unsubstituted aryl group, a substituted or unsubstituted lower alkylene group, or —CH=$R^4$— ($R^4$ is a ring structure having an oxo group), A is a substituted or unsubstituted aryl group or —CH=$R^5$— ($R^5$ is a substituted or unsubstituted heterocyclic ring, a substituted or unsubstituted cycloalkyl group, or a substituted or unsubstituted aromatic ring), the hydrogen atom bonded to a carbon atom not having $R^1$, $R^2$ and $R^3$ on the pyrylium ring or its similar ring containing X may be substituted by a halogen atom, sulfonate group, amino group, styryl group, nitro group, hydroxyl group, carboxyl group, cyano group, substituted or unsubstituted lower alkyl group, substituted or unsubstituted aryl group, or substituted or unsubstituted lower aralkyl group, and $Y^-$ is an anion.

The second aspect of the present invention is directed to a method for detecting a nucleic acid which comprises the steps of reacting a sample with a stain for a nucleic acid described above, and then detecting, by an optical means, the double-strand nucleic acid stained with the stain in the case that the double-strand nucleic acid is contained in the sample.

The third aspect of the present invention is directed to a probe for the detection of a target nucleic acid which is characterized by comprising a nucleic acid having a base sequence which was complementary to a base sequence of the target nucleic acid, and a compound represented by the above formula [I] which is bonded as a label to the nucleic acid.

The fourth aspect of the present invention is directed to a method for the detection of a target nucleic acid which comprises a step of reacting a sample with a probe described above, and a step of optically detecting a hybrid of the probe and the target nucleic acid obtained in the case that the target nucleic acid is present in the sample solution by a label bonded to the probe.

The fifth aspect of the present invention is directed to a salt of 2-methyl-4,6-bis-(4-N,N-dimethylaminophenyl) pyrylium or thiopyrylium which is represented by the formula [VIII]

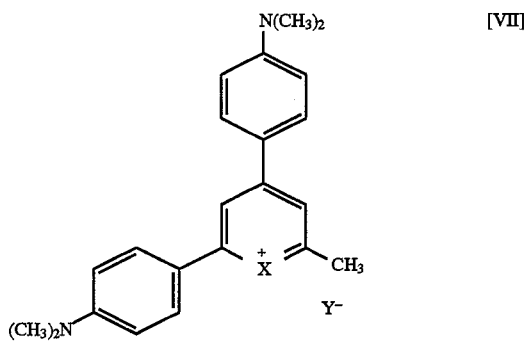

(wherein X is O or S, and Y⁻ is an anion).

The sixth aspect of the present invention is directed to a method for the fluorescence staining of a biological sample which comprises bringing the biological sample into contact with a solution of a fluorescence dyestuff, said method being characterized in that the fluorescence dyestuff is a compound represented by the above formula [I].

The seventh aspect of the present invention is directed to a method for preparing a storage specimen of a biological sample which comprises the step of sealing, in a vessel, a biological sample stained by the above fluorescence staining method.

The eighth aspect of the present invention is directed to the above detection method for the detection of a target nucleic acid by the use of in situ hybridization in which the reaction step and the detection step are carried out in an organism, live cells or live bacteria.

The ninth aspect of the present invention is directed to a kit for carrying out the above detection method.

DESCRIPTION OF THE PREFERRED EMBODIMENTS

Figure 1:
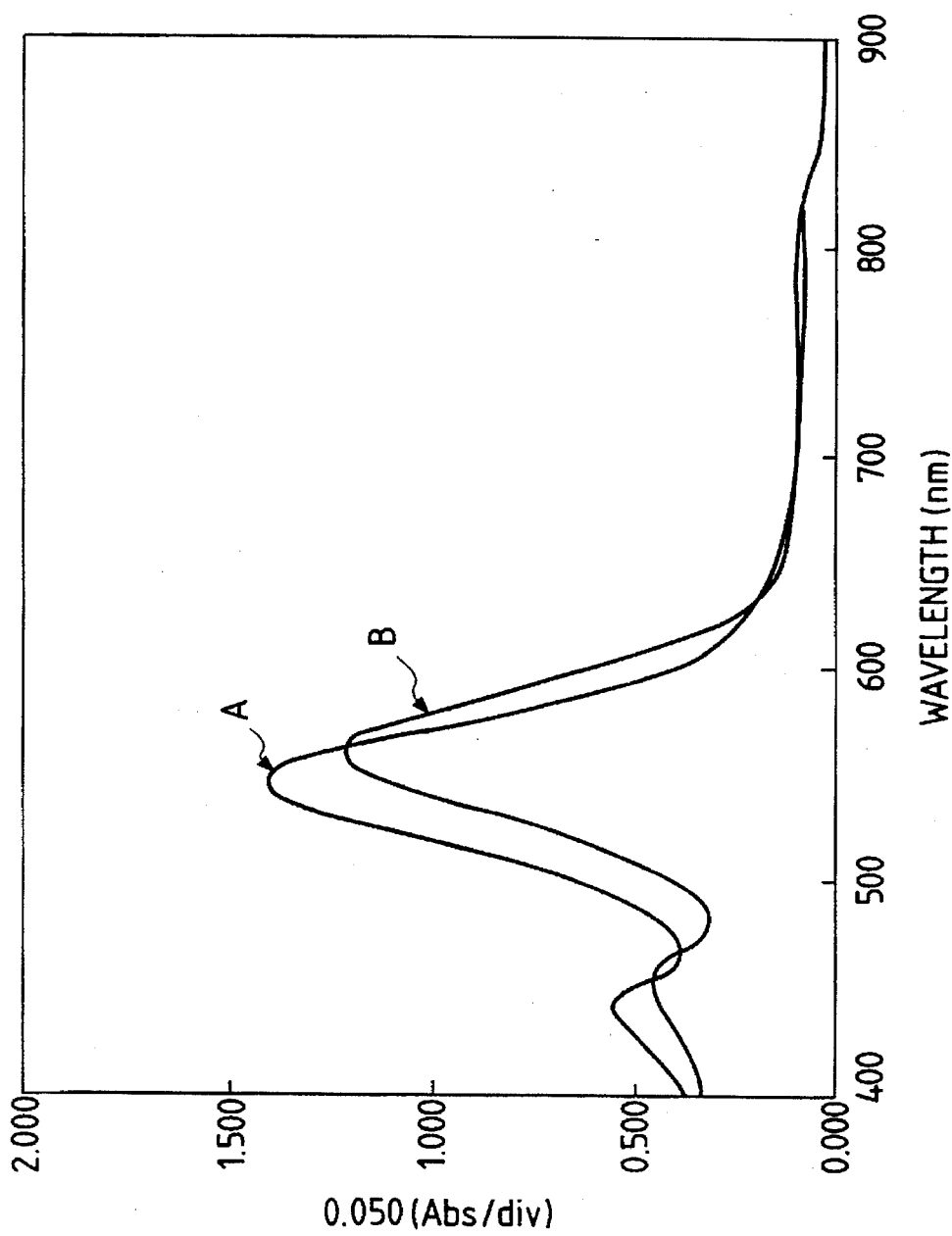
FIG. 1 is a graph showing the shift of an absorption peak in Example 3, and A denotes an absorption spectrum in the absence of DNA and B denotes an absorption spectrum in the presence of DNA (50 μg/ml).

A stain for a nucleic acid of the present invention is characterized by containing a compound represented by the formula [I] as an effective component.

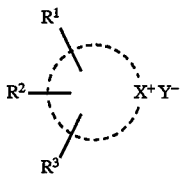

In the above-mentioned formula [I],

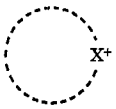

represents a heterocyclic ring, and X is O, S, Se or Te. Examples of the heterocyclic ring include a five-membered ring and a six-membered ring such as a pyrylium ring and a pyrylium-similar ring.

Each of $R^1$ and $R^2$ is independently a hydrogen atom, halogen atom, sulfonate group, amino group, styryl group, nitro group, hydroxyl group, carboxyl group, cyano group, substituted or unsubstituted lower alkyl group, substituted or unsubstituted aryl group, substituted or unsubstituted lower aralkyl group, or substituted or unsubstituted cycloalkyl group.

$R^3$ is —A or —L—A. L is —$L^1$—, —$L^2$—$L^3$— or —$L^4$—$L^5$—$L^6$—, and each of $L^1$ to $L^6$ is independently —(CH=CH)—, a divalent group derived from the substituted or unsubstituted aryl group, a substituted or unsubstituted lower alkylene group, or —CH=$R^4$— ($R^4$ is a ring structure having an oxo group). An example of the divalent group derived from the substituted or unsubstituted aryl group is a phenylene group to which substituents may be bonded at any position of ortho, meta and para positions. An example of the lower aralkyl group is a straight-chain or branched alkylene group having 1 to 4 carbon atoms, and an example of a substituent on the lower aralkyl group is a group represented by —L—A. Examples of the ring structure having the oxo group include a heterocyclic ring, aromatic ring and aliphatic ring having at least the oxo group.

Preferable examples of the —L— include groups represented by the formulae [II], [III], [IV], [V] and [VI]:

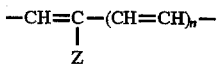 [II]

(wherein Z is a hydrogen atom or a substituted or unsubstituted lower alkylene group, and n is 0, 1 or 2). An example of a substituent on the alkyl group represented by Z is a group defined by the above-mentioned —L—A.

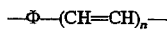 [III]

(wherein n is 0, 1 or 2, and Φ is a substituted or unsubstituted o-, m- or p-phenylene group.)

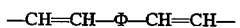 [IV]

(wherein Φ is a substituted or unsubstituted o-, m- or p-phenylene group.)

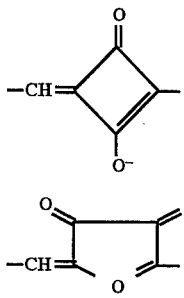

A substituent on the phenylene group in the above-mentioned formulae is previously exemplified.

A in $R^3$ of the formula [I] is a substituted or unsubstituted aryl group or —CH=$R^5$— ($R^5$ is a substituted or unsubstituted heterocyclic ring, a substituted or unsubstituted cycloalkyl group, or a substituted or unsubstituted aromatic ring). Examples of the heterocyclic ring represented by $R^5$ include groups derived from

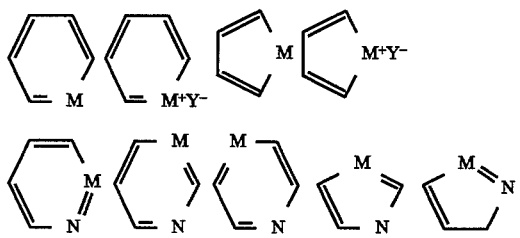

(each of M and N is independently an oxygen atom, sulfur atom or nitrogen atom, and Y⁻ is an anion), and an example of a substituent on the heterocyclic ring is a substituted or unsubstituted aryl group. The substituted or unsubstituted cycloalkyl group may be saturated or unsaturated, and examples of the substituted or unsubstituted cycloalkyl group include groups derived from resonance systems such as

Furthermore, an example of the substituted or unsubstituted aromatic ring is an azulene ring. Examples of substituents on these groups include lower alkyl groups and substituted or unsubstituted aryl groups.

The hydrogen atom bonded to a carbon atom not having $R^1$, $R^2$ and $R^3$ on the pyrylium ring or its similar ring containing X may be substituted by a halogen atom, sulfonate group, amino group, styryl group, nitro group, hydroxyl group, carboxyl group, cyano group, substituted or unsubstituted lower alkyl group, substituted or unsubstituted aryl group, or substituted or unsubstituted lower aralkyl group.

Y⁻ is an anion, and examples of the anion include $BF_4^-$, a perchlorate ion, $HO_3SCH_2COO^-$, halogen ions such as a chlorine ion, bromine ion, iodine ion and fluorine ion, compounds having an anionic function such as aliphatic hydrocarbons and aromatic sulfonates, and complex ions of transition metals such as Zn, Ni, Cu, Pt, Co and Pd.

A group which is further substituted on the above-mentioned various substituents may be a halogen atom, and examples of the halogen atom include Cl, Br and I. Moreover, the lower alkyl group may be straight-chain or branched, and the number of carbon atoms in this lower alkyl group is preferably from 1 to 4. An example of the aryl group is a phenyl group. An example of a substituent on the aryl group or phenylene group is an amino group (a lower alkylamino group) substituted by a lower alkyl group. This lower alkylamino group is preferably substituted by a dimethylamino group or diethylamono group at the para position. An example of the lower aralkyl group is a lower alkyl group substituted by the above-mentioned substituted or unsubstituted aryl group.

Among the compounds represented by the formula [I], preferable are compounds in which the heterocyclic ring containing X is substituted by the two or more substituted or unsubstituted aryl groups. For example, when the heterocyclic ring containing X is a six-membered ring, examples of such compounds include:

(1) a compound in which the 2-position and 4-position of the six-membered ring containing X are substituted by the substituted or unsubstituted aryl groups, and any of the 3-position, 5-position and 6-position is substituted by $R^3$, (2) a compound in which the 3-position and 5-position of the six-membered ring are substituted by the substituted or unsubstituted aryl groups, and any of the 2-position, 4-position and 6-position is substituted by $R^3$, (3) a compound in which the 2-position and 6-position of the six-membered ring are substituted by the substituted or unsubstituted aryl groups, and any of the 3-position, 4-position and 5-position is substituted by $R^3$.

The introduction of the substituted or unsubstituted aryl groups into such positions is preferable to obtain good characteristics as an intercalater to the base pair of the nucleic acid. In addition, more preferable is a compound in which the heterocyclic ring containing X is substituted by two or more of the substituted or unsubstituted aryl groups so that these substituted positions may not be adjacent to each other.

Typical examples of the compound represented by the formula [I] include compounds shown in Table 1 given below. Furthermore, particularly preferable examples are compounds represented by the formula [VII]

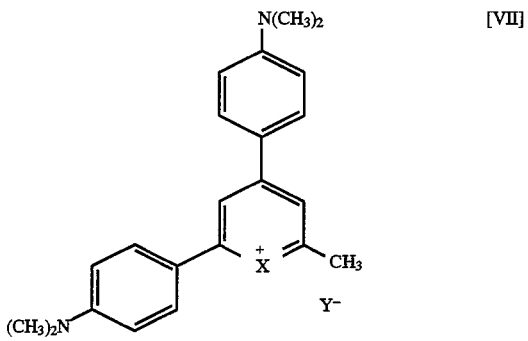

(wherein X is O or S, and Y⁻ is an anion), and compounds represented by the formula [VIII]

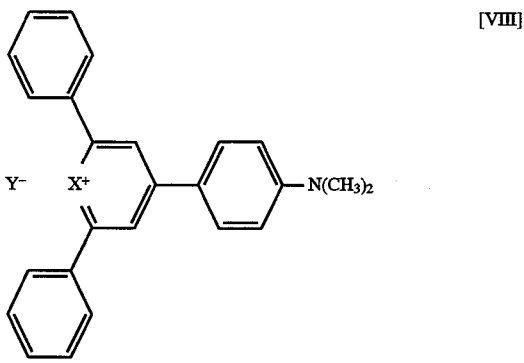

(wherein X is O or S, and Y⁻ is an anion).

In this connection, the compounds represented by the formula [VII], i.e., 2-methyl-4,6-bis-(4-N,N-dimethylaminophenyl)pyrylium salts and 2-methyl-4,6-bis-(4-N,N-dimethylaminophenyl)thiopyrylium salts are novel compounds.

That is, each of these pyrylium salts has a methyl group at the 2-position, and therefore they are different in structure from compounds which are heretofore known as sensitizers for recording materials and which possess substituted or unsubstituted phenyl groups at the 2, 4 and 6-positions of the pyrylium ring or the thiopyrylium ring. Moreover, they are also different in structure from compounds which are described in Japanese Patent Application Laid-open Nos. 59-133460 and 1-153683 and in which the 2, 4 and 6-positions of the pyrylium ring or the thiopyrylium ring are substituted by the substituted or unsubstituted phenyl groups, or two of the 2, 4 and 6-positions of the pyrylium ring or the thiopyrylium ring are substituted by the substituted or unsubstituted phenyl groups and the remaining one position is substituted by the substituted styrene group.

In addition, in these publications, it is not described that the pyrylium salt or the thiopyrylium salt of the present invention functions as an intercalater specific to the double strand nucleic acid owing to the structure in which kinds of substituted positions of the substituents of the pyrylium salt or the thiopyrylium salt are specified, i.e., the structure in which the 4 and 6-positions of the pyrylium ring or the thiopyrylium ring are substituted by phenyl groups having a dimethylamino group at the para position and the 2-position is substituted by a methyl group, so that fluorescence intensity can be increased. Moreover, the degree of the fluorescence increase by the intercalation to the double strand nucleic acid of the pyrylium salt or the thiopyrylium salt [VII] of the present invention is from about 5 times to about 10 times as much as that of the fluorescence increase by a 4-(4-N,N-dimethylaminophenyl)-2,6-diphenylpyrylium salt or a 4-(4-N,N-dimethylaminophenyl)-2,6-diphenylthiopyrylium salt, i.e., [VIII], and the stokes shift is also large, about 100 nm. Therefore, the pyrylium salt or the thiopyrylium salt [VII] of the present invention is particularly useful as the dyestuff for the detection of the double-strand nucleic acid.

The compound represented by the formula [I] can be directly used, or dissolved or dispersed in a suitable solvent or dispersant, thereby obtaining the stain for the nucleic acid of the present invention. Examples of the solvent or dispersant include water, acetonitrile, dimethyl sulfoxide, and various kinds of buffer solutions such as a phosphoric acid buffer solution and an acetic acid buffer solution. In this case, the content of the compound represented by the formula [I] can be suitably selected in compliance with its use and the sensitivity of a measuring device, and for example, for the detection of the double-strand nucleic acid in an aqueous nucleic acid solution, the content of the compound is in the range of from about $1\times10^{-6}$ to about $1\times10^{-4}$M.

The compound represented by the formula [I] can be utilized to stain the single-strand or the double-strand nucleic acid (DNA and RNA), and since the compound has the intercalater function, it has the advantage that it predominantly stains the double-strand nucleic acid. That is, when this compound is intercalated in the double helix, its fluorescence intensity more increases than in the case of a free state, and if the compound having the large stokes shift is selected, analysis can be carried out in a high S/N ratio.

In addition, this compound has feature that when bonded to the double-strand nucleic acid, the compound is stable and the fade phenomenon which is often seen in the case of a fluorescent dyestuff is scarcely observed.

Moreover, since the excitation wavelength of most of compounds [I] is 550 nm or more on the long wavelength side, a sufficient excitation state can be obtained by the use of a visible light source such as a tungsten lamp. Therefore, the above-mentioned problems in the case of using the ultraviolet rays can be avoided.

Furthermore, the specimen derived from an organism often contains a component having absorption/fluorescence in a wavelength region of 550 nm or less, and so if light in this wavelength region is used as excitation light, the S/N ratio decreases inconveniently owing to the rise of the measured background attributed to this component. On the contrary, the excitation wavelength of most of the compounds represented by the formula [I] is present on a long wavelength side of 550 nm or more, and therefore the rise of the background does not occur, so that the high-sensitive measurement is possible. This means that even if the purification of the nucleic acid is insufficient, the high-sensitive measurement can be achieved. In particular, it is effective for an efficient operation that a purification step can be omitted in the treatment of many specimens as in a blood test.

In addition, if the compound of the formula [I] having the absorption in a near infrared region is utilized, a small inexpensive semiconductor laser can be advantageously utilized as a light source for the excitation.

As described above, when the compound of the formula [I] is intercalated in the double helix, the fluorescence intensity is remarkably larger, as compared with the case of a free state (i.e., a state containing no interaction with the double helix), and so when a pattern of DNA digested by a restriction enzyme is detected as in an agarose gel electrophoresis, the background can be inhibited to a low level, so that the detection sensitivity of DNA can be relatively heightened. Furthermore, since the stokes shift is about 100 nm above, the influence of the excitation light can be completely eliminated at the time of the fluorescence detection, whereby a direct visual observation is possible.

In addition, the compound of the formula [I] of the present invention is stable when bonded to the double-strand nucleic acid, and the fade phenomenon which is often seen in the case of the fluorescent dyestuff is scarcely observed. This feature can be maintained even when the gel is dried, and thus the long-term storage of the gel is also possible.

Moreover, in the case of ethidium bromide which is the typical fluorescent intercalater, the fluorescence is observed even in the absence of DNA, but in the case of the compound of the formula [I], the fluorescence is scarcely observed under such conditions. In addition, the increase of the fluorescence intensity which depends upon the concentration of DNA can be observed until a certain high concentration of DNA, in contrast to ethidium bromide.

That is, the compound of the formula [I] has a higher detection sensitivity than ethidium bromide and is excellent in the S/N ratio, so that the detection of DNA is possible in a wide concentration range.

Additionally, even in the detection of the nucleic acid by a hybridization reaction of a solution system, if the compound of the formula [I] is used for the staining (labeling) of a hybrid, the fluorescence intensity of the compound is sufficiently high in a state in which it is intercalated in the double strand (double helix) than in the case that it is free or bonded to the single strand. Therefore, the hybrid of a probe and the target nucleic acid can be directly detected without separating the hybrid of the probe and the target nucleic acid from the unreacted probe.

Moreover, since having the function as the intercalater, the compound of the formula [I] is also advantageous to stabilize the hybrid of the target nucleic acid and the probe, and even if a short oligonucleotide is used as the probe, the stable hybrid can be formed and the stabilization of the measurement can be achieved.

As described above, if the compound of the formula [I] having the large stokes shift is selected, the fluorescence and the excitation light can be completely separated from each other. In consequence, the operation of subtracting the influence of the excitation light from the fluorescence spectrum is unnecessary, which is convenient for the sake of the automation of the detection and which leads to the advantage that the detection sensitivity can be heightened.

These features of the compound represented by the formula [I] are based on the heterocyclic ring and the specific substituents bonded thereto, and it can be presumed that the compound is intercalated in the nucleic acid base pair portion where the portions of the heterocyclic ring and the substituents are stacked, so that it interacts with both the portions to increase the fluorescence intensity. This enhancement effect of the fluorescence intensity is larger when the substituents have the substituted or unsubstituted aryl group, and it is further larger when the substituents are substituted by two or more of the substituted or unsubstituted aryl groups so that these substituted positions may not be adjacent to each other. Moreover, by partially changing the structure of the compound having the formula [I], a derivative having various absorption wavelength, excitation wavelength and fluorescence wavelength can be synthesized, and for example, the compound to which the semiconductor laser can be applied as the excitation wavelength can be obtained. In addition, when the heterocyclic ring or a condensed ring is introduced as the substituent, the characteristics of the introduced ring structure can be utilized for a chemical reaction or a biochemical reaction in combination with the intercalater and another mechanism.

Furthermore, in order to improve the water solubility of the compound having the formula [I], a hydrophilic group such as an amino group, a dimethylamino group or a sulfonate group may be introduced into a suitable portion. If the compound is used as the label of the nucleic acid probe and if the sufficient hydrophilic nature can be obtained when bonded to the nucleic acid, the compound can be directly utilized without introducing any hydrophilic group.

The nucleic acid stain of the present invention can be used as a stain for the nucleic acid, for example, to detect the nucleic acid separated by electrophoresis. This detection can be fundamentally carried out in accordance with a conventional method by the use of the nucleic acid stain of the present invention in place of ethidium bromide or the like. That is, after the usual electrophoresis, a gel is immersed in a dyestuff solution, followed by detecting. In this case, however, the visible light is used instead of the ultraviolet lamp, and so the constitution of the detection system which is different from the conventional case is necessary. That is, in the detection system, an excitation filter and a fluorescence filter are required in addition to the light source.

Examples of the utilizable light source include a halogen lamp, a tungsten lamp, an xenon lamp and a semiconductor laser. If the visible light source capable of Generating a light amount from a slide projector (100 V, 300 W) or the like is used, the detection can be made with the sensitivity higher than in the case of ethidium bromide. A strobe which can be used in photography by a camera is also effective in taking a photograph. In addition, if the semiconductor laser is used, a densitometer can be constituted in combination with a photomultiplier without using any filter for the excitation light.

Moreover, as the excitation light filter and the detection filter, filters corresponding to the respective dyestuffs are necessary. That is, the filter which covers the optical absorption of each dyestuff and cuts the fluorescence region is used on the excitation light side, and the filter which prevents the transmission of the excitation light and passes through the fluorescence alone is used on the detection side.

For example, a visible light source is attached in place of the ultraviolet lamp in a transilluminator, and a base equipped with the excitation light filter is put thereon. The gel is mounted on the base, and the detection is carried out through a slit provided with the fluorescence filter, or a photograph is taken by the camera provided with the fluorescence filter.

In consequence, bands moved in the gel can be observed by the naked eye without using any protective tool, and the cutting of the bands from the gel is also easy. Furthermore, also when the photographs are taken, a suitable exposure can be selected by the naked eye, in contrast to the case of ethidium bromide in which the exposure is selected by the transilluminator with trial and error, while the ultraviolet rays are avoided. Needless to say, a densitometer equipped with the photomultiplier can also be utilized. In addition, if a detection kit which uses a strobe as the light source and which can operate simultaneously with the camera is used, the detection of the nucleic acid can be simply carried out with a power source such as a dry cell without being affected by generated heat.

Furthermore, the nucleic acid stain of the present invention can be used to detect the target nucleic acid which is the detection object by the hybridization method using the probe. For example, the detection can be achieved by the procedures of reacting the target nucleic acid with a specimen, staining the formed double-strand nucleic acid with the stain of the present invention, and then optically detecting it. In this case, the compound of the formula [I] contained in the stain interacts with the double helix to increase the fluorescence intensity, and thus the detection is possible without a B/F separation. In addition, this interaction scarcely occurs on the double-strand nucleic acid in which mismatching takes place, and so the influence of the miss-matched double-strand nucleic acid on measured values can be eliminated. The staining technique which uses the stain of the present invention can be applied to a method in which the probe or the specimen is immobilized and then used, a method in which the probe is reacted with the specimen in a solution, a biopsy, and an in site hybridization method in which the probe is incorporated into cells or an organism. For example, the specimen is reacted with the probe, and the stain of the present invention is then added to the reaction system to stain the resulting target hybrid, followed by the detection. Moreover, the employment of a microscope permits inspecting a position in each cell where the probe is hybridized.

Needless to say, the stain of the present invention can also be used to detect the nucleic acid amplified by PCR or the like, and it can be immediately judged whether or not the nucleic acid is amplified, without quantitatively analyzing one by one. At this time, if the reaction of PCR is carried out on a microplate, many specimens can be inspected at one time.

Furthermore, when the compound of the present invention [I] is used as a label to be bonded to the probe, the features of the compound can be more effectively utilized. For example, in the hybridization reaction which is carried out in a solution, the compound can be applied to the object to be analyzed, i.e., the target nucleic acid having not only the single strand but also the double strand. In addition, since the compound has the function as the intercalater to the nucleic acid base pair, a steric hindrance of the label compound in the hybrid of the target nucleic acid and the probe can be avoided, and the hybrid can be effectively stabilized by stacking. In order to bond the compound of the formula [I] to the probe, various known methods can be utilized.

As described hereinafter, the compound represented by the formula [I] of the present invention shows high permeability to a biological specimen such as cells, bacteria, a tissue and a chromosome, and therefore it is easy to incorporate the probe labeled with the compound into the cells or the organism. Hence, the compound is suitable for the in situ hybridization method.

Moreover, as described hereinafter, since the compound of the formula [I] can be sufficiently used at a low concentration and has low residence properties, culture can be continued even after the reaction of the organism with the probe and the observation.

The compound represented by the formula [I] of the present invention can be applied to various detection methods, and what is better, it permits the detection of the nucleic acid very easily. Therefore, various kinds of nucleic acid detection kits can be provided which contain the compound represented by the formula [I] as it is, or in the form of the probe.

Furthermore, the stain containing the compound of the formula [I] of the present invention can be brought into contact with the biological specimen to stain or differentially stain it.

Examples of the biological specimen which can be stained by the method of the present invention include microorganisms, human cells, animal cells, a tissue and a section of creatures (a human, an animal and a plant), and a chromosome. When the chromosome is used as the specimen, it can be differentially stained in a sharp state.

In the present invention, one or more kinds of compounds represented by the formula [I] of the present invention are dissolved in a suitable solvent such as water, physiological saline or a mixed solvent of water and an alcohol such as ethanol, and then used for the fluorescence staining of the biological specimen. Moreover, when the biological specimens are live cells, microorganisms or the like, the compound of the present invention can be added to a certain solution in which they can be kept alive or a culture medium in which they can grow, to form a staining solution.

The concentration of the compound of the present invention in the staining solution is suitably in the range of from several tens ng to several μg/ml.

In the present invention, when the compound of the formula [I] is used as the dyestuff for the staining or the differential staining, the stable staining can be achieved with good reproducibility without unevenness, and what is better, operations such as the fixation of the specimen and the washing of the excessive dyestuff which are essential in conventional methods can be omitted, whereby the treatment operation can be simplified and a large number of the specimens can be promptly treated.

Also in the differential staining of the chromosome, a known stain and a differentially stained pattern can be obtained by the use of the compound of the present invention, and the distinction and the identification of the chromosome can be achieved with high precision.

In addition, the employment of the compound of the present invention also permits the preparation of storage specimens in which the stained portions neither fade nor disappear.

In particular, the compound of the formula [I] which can be used in the present invention is excellent in permeability into the specimen, and therefore operations for feeding this compound into the biological specimen, for example, the fixation of the specimen and the subsequent washing operation can be advantageously omitted. Moreover, in the case that the fixation operation is omitted, the specimen can be utilized in a non-fixed free state, i.e., in a natural state or a state similar thereto. For example, it can be stained in a live state. Also in the differential staining of the chromosome, the fixation operation by a calnoa fixation solution and the subsequent washing operation and a drying step can be omitted.

As described above, the compound of the present invention scarcely generates the fluorescence even by the irradiation of excitation light, when the compound is in a free state in the solution, i.e., when any nucleic acid is not present, but it emits the fluorescence, when it interacts with the existent double-strand nucleic acid. This means that background is extremely low, which permits highly precise staining. In addition, owing to the above-mentioned low background properties, it is possible to utilize the compound of the present invention in an extremely wide concentration range.

For example, in the case that 2-methyl-4,6-bis-(4-N,N-dimethylaminophenyl)pyrylium iodide (compound 1) is directly added to the culture medium of cells or microorganisms and observation is made in a state in which the staining solution is coexistent by a usual refractive fluorescence microscope, it is apparent that the compound can be used in a dyestuff concentration range of several tens ng/ml to several μg/ml in the staining solution without the background. In consequence, the washing after the staining operation which has been heretofore necessary can be completely omitted or simplified.

Even when the staining solution having a high concentration of several tens μg/ml or so is used in order to stain the tissues or sections of an animal or a human, the washing after the staining operation which has been heretofore necessary can be completely omitted or simplified.

On the other hand, with regard to stained images, the compound of the present invention sharply stains the nucleus of each cell, and in the staining of the live cells such as cultured cells, cultured bacteria or various tissues, the chromosome of the dividing cell can be clearly observed. This is due to the fact that the compound of the present invention has a strong affinity for the nucleic acid (i.e., DNA, RNA, the double-strand nucleic acid, the intramolecular double-strand portion of a single-strand nucleic acid, or the like), but the utilization of this feature permits the count of cells by FCM (a flow sight meter) and the classification of the cells in a division period step.

In the case that the live specimen is stained, the water solubility of the stain is very important. The live specimen is often handled in an aqueous environment. On the contrary, the dyestuff is often handled in an organic solvent system. In the field where the live specimen is treated, the dyestuff which can be used in the aqueous system is strongly desired, and it is utilizable in a wide range. The compound of the present invention is also very useful in that the water solubility of the compound of the present invention can be heightened by selecting a suitable counter ion (e.g., iodine).

The compound of the formula [I] in the present invention has the low residence properties in the cells, and so the live cells are not badly affected by the residence. Therefore, when the target to be stained is the cultured cells or microorganisms, the staining and the stained state can be observed without fixation only by taking slight care of the contamination with other microorganisms and the control of temperature, and after the observation, they can be continuously cultured. That is, the fluorescence stain observation with time of the same specimen is possible.

As described above, the compound of the present invention also has the feature that the fade phenomenon of the fluorescence which occurs in the case of the fluorescence dyestuff is very slight. The employment of both the features of the low background and the low fade phenomenon which the compound of the present invention has permits the preparation of the specimens for long-term storage of the fluorescence dyestuff. That is, in placing the specimen together with a storage solution in a vessel and then sealing up it, if the compound of the formula [I] of the present invention is added to the storage solution, the renewal of the dyestuff is carried out in the stored specimen, even though the fade phenomenon slightly occurs. Thus, the change of the images to be observed can be inhibited for a long period of time.

The preparation of the storage specimens by the utilization of the staining method of the present invention can be achieved by staining the biological specimen with the compound of the present invention, placing the stained specimen in a suitable vessel, and then sealing up it. Any vessel having an optional shape and size can be used in compliance with a purpose, so long as it can seal up the specimen. A container obtained by sealing the periphery of a cover glass put on a slide glass with a sealing material such as a resin is included in the category of this vessel.

The stained biological specimen is placed in the vessel, if necessary, together with a liquid medium containing an antiseptic such as sodium azide, and the vessel is then sealed up. Alternatively, the biological specimen may be mixed with the staining solution in the vessel, followed by sealing. Any liquid medium can be used, so long as it can be utilized as a staining solvent. Moreover, if the biological specimen is added to the liquid medium containing the fluorescence dyestuff in the sealable vessel, the a stained state can be stably maintained during the above-mentioned long-term storage.

Next, the present invention will be described in more detail in reference to examples, but the scope of the present invention should not be limited to these examples.

EXAMPLE 1

100 ml of acetic anhydride was mixed with 30 ml of concentrated sulfuric acid with cooling, and the resulting mixture was then heated for 3 hours on a water bath, while maintained at 80° C. Next, 20 ml of acetic anhydride and 30 ml of p-dimethylamino acetophenone were added thereto at room temperature, and the temperature of the solution was then raised up to 45° C., followed by stirring for 24 hours to carry out reaction. Afterward, ethanol was added to the reaction solution, the amount of ethanol being equal to that of the reaction solution. This solution was cooled, and an aqueous potassium iodide solution was then added thereto to precipitate crude crystals. Next, the crystals were collected by filtration, and then recrystallized from a mixing system of ethanol and ether (a volume ratio=1:4) to obtain Green crystals of 2-methyl-4,6-bis-(4-N,N-dimethylaminophenyl) pyrylium iodide (compound 1 in Table 1 wherein Y is I).

Analytical results of the obtained compound 1 (Y=I):

Melting point: 254°–257° C.

UV/visual ($CH_3CH$ $\epsilon \times 10^{-4}$) λmax: 444 nm (2.43), 550 nm (8.24)

NMR ($^1H$, DMSO) δppm: 8.3737 (1H, s), 8.2729 (1H, d, J=9.0 Hz), 8.1795 (1H, d, J=9.0 Hz), 7.8864 (1H, s), 6.9117 (4H, t, $J_{AB}=J_{BC}=9.77$), 3.1829 (6H, s), 3.1340 (6H, s), 2.6809 (3H, s)

FAB mass m/z 333

IR (KBr) V $cm^{-1}$: 1645, 1610 (sh), 1580 (s), 1490 (s), 1270, 1200, 1160

Furthermore, the same procedure as described above was carried out except that the aqueous potassium iodide solution was replaced with an aqueous perchloric acid solution, to obtain 2-methyl-4,6-bis-(4-N,N-dimethylaminophenyl) pyrylium perchlorate (compound 1 in Table 1 wherein Y is $ClO_4$).

EXAMPLE 2

20 g of sodium sulfide nonahydrate was dissolved in ion-exchanged water so as to bring the total volume to 50 ml. Next, 7 g of sodium hydrogencarbonate was added to and dissolved in this solution, and 50 ml of ethanol was further added thereto under ice cooling, followed by stirring at room temperature for 30 minutes. The precipitated sodium carbonate was collected by filtration, and then washed with 25 ml of ethanol. Afterward, the filtrate was mixed with the washing liquid to obtain about 125 ml of the water-ethanol solution of sodium hydrogen sulfide.

Next, 0.92 g of 2-methyl-4,6-bis-(4-N,N-dimethylaminophenyl)pyrylium iodide obtained in Example 1 was dissolved in 20 ml of DMSO, and 5 ml of the previously prepared water-ethanol solution of sodium hydrogen sulfide was then added to the resulting solution, followed by stirring at room temperature for 5 minutes. After the stirring, 0.75 ml of hydroiodic acid was added thereto, and the solution was further stirred for 5 minutes. Subsequently, dichloromethane extraction and silica gel column purification were carried out in usual manners, followed by recrystallication in an ethanol-ether mixed solution (a volume ratio=1:4), to obtain the crystals of 2-methyl-4,6-bis-(4-N,N-dimethylaminophenyl) thiopyrylium iodide (compound 2 in Table 1 wherein Y is I).

Analytical results of the obtained compound 1 (Y=I):

Melting point: 246°–248° C.

UV/visual ($CH_3CH$ $\epsilon \times 10^{-4}$) λmax: 495 nm(2.50), 587 nm (4.95)

NMR ($^1H$, DMSO) δppm: 8.5679 (1H, s), 8.4323 (1H, s), 8.2436 (2H, d, J=9.27 Hz), 7.9786 (2H, d, J=9.28), 6.8959 (4H, t, $J_{AB}=J_{BC}=9.28$), 3.1756 (6H, s), 3.1157 (6H, s), 2.8323 (3H, s)

FAB mass m/z 349

IR (KBr) V $cm^{-1}$: 1600 (s), 1560 (s), 1460 (s), 1430 (s), 1370 (s), 1260 (s), 1160 (s)

Furthermore, the same procedure as described above was carried out except that hydoriodic acid was replaced with an aqueous perchloric acid solution, to obtain 2-methyl-4,6-bis-(4-N,N-dimethylaminophenyl)thiopyrylium perchlorate (compound 2 in Table 1 wherein Y is $ClO_4$).

Reference Example 1

Compounds 3 to 55 shown in Table 1 were prepared. In Table 1, Φ is a p-phenylene group

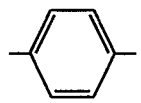

or a phenyl group.

TABLE 1

| Compd No. | X | Y | $R_i$ | L | A |
|---|---|---|---|---|---|
| 1 | O | $ClO_4$ or I | $R_6 = CH_3$<br>$R_7 = H$<br>$R_8 = \Phi\text{-N}(CH_3)_2$<br>$R_9 = H$<br>$R_{10} = A$ | | $\Phi\text{-N}(CH_3)_2$ |
| 2 | S | $ClO_4$ or I | $R_6 = CH_3$<br>$R_7 = H$<br>$R_8 = \Phi\text{-N}(CH_3)_2$<br>$R_9 = H$<br>$R_{10} = A$ | | $\Phi\text{-N}(CH_3)_2$ |
| 3 | O | $ClO_4$ or I | $R_6 = \Phi$<br>$R_7 = H$<br>$R_8 = A$<br>$R_9 = H$<br>$R_{10} = \Phi$ | | $\Phi\text{-N}(CH_3)_2$ |
| 4 | S | $ClO_4$ or I | $R_6 = \Phi$<br>$R_7 = H$<br>$R_8 = A$<br>$R_9 = H$<br>$R_{10} = \Phi$ | | $\Phi\text{-N}(CH_3)_2$ |
| 5 | O | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | $\Phi\text{-N}(CH_2CH_3)_2$ |
| 6 | S | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | $\Phi\text{-N}(CH_2CH_3)_2$ |
| 7 | O | $ClO_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | $\Phi\text{-N}(CH_3)_2$ |
| 8 | S | $ClO_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | $\Phi\text{-N}(CH_3)_2$ |
| 9 | O | $ClO_4$ or I | $R_6 = \Phi$<br>$R_7 = H$ | General Formula [II]<br>n = 1 | $\Phi\text{-N}(CH_3)_2$ |

TABLE 1-continued

[Structure: 6-membered ring with R8 (top), R9 and R7 (upper sides), R10 and R6 (lower sides), X+ at bottom with Y-]

| Compd No. | X | Y | R_i | L | A |
|---|---|---|---|---|---|
| 10 | S | ClO₄ or I | R₆ = Φ<br>R₇ = H<br>R₈ = L—A<br>R₉ = H<br>R₁₀ = Φ | General Formula [II]<br>n = 1<br>Z = H | Φ-N(CH₃)₂ |
| 11 | O | ClO₄ or I | R₆ = Φ<br>R₇ = H<br>R₈ = L—A<br>R₉ = H<br>R₁₀ = Φ | General Formula [II]<br>n = 1<br>Z = (-)CH=CH-Φ-N(CH₃)₂ | Φ-N(CH₃)₂ |
| 12 | S | ClO₄ or I | R₆ = Φ<br>R₇ = H<br>R₈ = L—A<br>R₉ = H<br>R₁₀ = Φ | General Formula [II]<br>n = 1<br>Z = (-)CH=CH-Φ-N(CH₃)₂ | Φ-N(CH₃)₂ |
| 13 | O | ClO₄ or I | R₆ = Φ<br>R₇ = H<br>R₈ = L—A<br>R₉ = H<br>R₁₀ = Φ | General Formula [III]<br>n = 1 | Φ-N(CH₃)₂ |
| 14 | S | ClO₄ or I | R₆ = Φ<br>R₇ = H<br>R₈ = L—A<br>R₉ = H<br>R₁₀ = Φ | General Formula [III]<br>n = 1 | Φ-N(CH₃)₂ |
| 15 | O | ClO₄ or I | R₆ = Φ<br>R₇ = H<br>R₈ = L—A<br>R₉ = H<br>R₁₀ = Φ | General Formula [IV] | Φ-N(CH₂CH₃)₂ |
| 16 | S | ClO₄ or I | R₆ = Φ<br>R₇ = H<br>R₈ = L—A<br>R₉ = H<br>R₁₀ = Φ | General Formula [IV] | Φ-N(CH₂CH₃)₂ |
| 17 | O | ClO₄ or I | R₆ = Φ<br>R₇ = H<br>R₈ = Φ<br>R₉ = H<br>R₁₀ = L—A | General Formula [IV] | Φ-N(CH₂CH₃)₂ |
| 18 | S | ClO₄ or I | R₆ = Φ<br>R₇ = H<br>R₈ = Φ<br>R₉ = H<br>R₁₀ = L—A | General Formula [IV] | Φ-N(CH₂CH₃)₂ |
| 19 | O | ClO₄ or I | R₆ = Φ<br>R₇ = H<br>R₈ = Φ<br>R₉ = H<br>R₁₀ = L—A | General Formula [V] | [Pyranyl structure with Φ-N(CH₃)₂ groups, O in ring, (-)CH= substituent] |
| 20 | S | ClO₄ or I | R₆ = Φ<br>R₇ = H<br>R₈ = Φ<br>R₉ = H<br>R₁₀ = L—A | General Formula [V] | [Thiopyranyl structure with Φ-N(CH₃)₂ groups, S in ring, (-)CH= substituent] |

TABLE 1-continued

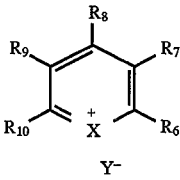

| Compd No. | X | Y | $R_i$ | L | A |
|---|---|---|---|---|---|
| 21 | O | ClO$_4$ or I | $R_6 = \Phi$<br>$R_7 = H$<br>$R_8 = \Phi$<br>$R_9 = H$<br>$R_{10} = L-A$ | General Formula [V] | 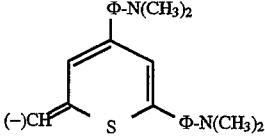 |
| 22 | O | ClO$_4$ or I | $R_6 = \Phi$<br>$R_7 = H$<br>$R_8 = \Phi$<br>$R_9 = H$<br>$R_{10} = L-A$ | General Formula [VI] | 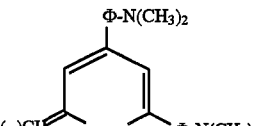 |
| 23 | S | ClO$_4$ or I | $R_6 = \Phi$<br>$R_7 = H$<br>$R_8 = \Phi$<br>$R_9 = H$<br>$R_{10} = L-A$ | General Formula [VI] | 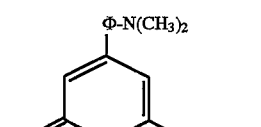 |
| 24 | O | ClO$_4$ or I | $R_6 = \Phi$<br>$R_7 = H$<br>$R_8 = \Phi$<br>$R_9 = H$<br>$R_{10} = L-A$ | General Formula [VI] | 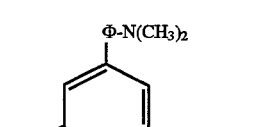 |
| 25 | O | ClO$_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | 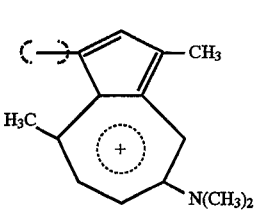 |
| 26 | S | ClO$_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | 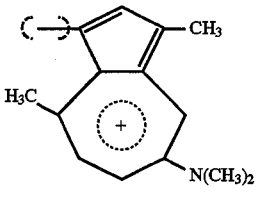 |
| 27 | O | ClO$_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | 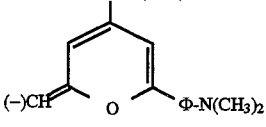 |
| 28 | S | ClO$_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | 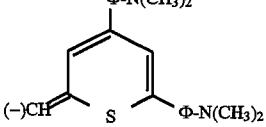 |

TABLE 1-continued

| Compd No. | X | Y | $R_i$ | L | A |
|---|---|---|---|---|---|
| 29 | O | $ClO_4$ or I | $R_6 = \Phi$<br>$R_7 = H$<br>$R_8 = \Phi$<br>$R_9 = H$<br>$R_{10} = L-A$ | General Formula [II]<br>n = 0<br>Z = H | (−)CH= attached to a 4H-pyran ring with $\Phi$-N(CH$_3$)$_2$ at 2,4-positions and O in ring, $\Phi$-N(CH$_3$)$_2$ |
| 30 | O | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | (−)CH= attached to a pyran ring with $\Phi$-N(CH$_3$)$_2$ groups, O in ring |
| 31 | S | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | (−)CH= attached to a thiopyran ring with $\Phi$-N(CH$_3$)$_2$ groups, S in ring |
| 32 | O | $ClO_4$ or I | $R_6 = \Phi$<br>$R_7 = H$<br>$R_8 = L-A$<br>$R_9 = H$<br>$R_{10} = \Phi$ | General Formula [II]<br>n = 0<br>Z = H | (−)CH= attached to a thiopyran ring with $\Phi$-N(CH$_3$)$_2$ groups, S in ring |
| 33 | O or S | $ClO_4^-$ or $I^-$ | $R_6 = \Phi$-N(CH$_3$)$_2$<br>$R_7 = H$<br>$R_8 = A$<br>$R_9 = H$<br>$R_{10} = \Phi$-N(CH$_3$)$_2$ | | $\Phi$-N(CH$_3$)$_2$ |
| 34 | O or S | $ClO_4^-$ or $I^-$ | Same as Compd No. 33 | | $CH_3$ |
| 35 | O or S | $ClO_4^-$ or $I^-$ | Same as Compd No. 33 | | $\Phi$-COOH |
| 36 | O or S | $ClO_4^-$ or $I^-$ | $R_6 = \Phi$-N(CH$_3$)$_2$<br>$R_7 = H$<br>$R_8 = L-A$<br>$R_9 = H$<br>$R_{10} = \Phi$-N(CH$_3$)$_2$ | General Formula [II]<br>n = 0<br>Z = H | $\Phi$-N(CH$_3$)$_2$ |
| 37 | O or S | $ClO_4^-$ or $I^-$ | Same as Compd No. 36 | General Formual [II]<br>n = 1<br>Z = H | $\Phi$-N(CH$_3$)$_2$ |
| 38 | O or S | $ClO_4^-$ or $I^-$ | Same as Compd No. 36 | General Formula [III]<br>n = 1 | $\Phi$-N(CH$_3$)$_2$ |
| 39 | O or S | $ClO_4^-$ or $I^-$ | Same as Compd No. 36 | General Formula [IV] | $\Phi$-N(CH$_3$)$_2$ |
| 40 | O or S | $ClO_4^-$ or $I^-$ | Same as Compd No. 36 | Gerneral Formula [II]<br>n = 0<br>Z = H | $\Phi$-COOH |
| 41 | O or S | $ClO_4^-$ or $I^-$ | Same as Compd No. 36 | General Formula [II]<br>n = 1<br>Z = H | $\Phi$-COOH |
| 42 | O or S | $ClO_4^-$ or $I^-$ | Same as Compd No. 36 | General Formula [III]<br>n = 1 | $\Phi$-COOH |

TABLE 1-continued

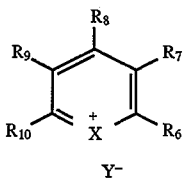

| Compd No. | X | Y | $R_i$ | L | A |
|---|---|---|---|---|---|
| 43 | S O or S | $ClO_4^-$ or $I^-$ | Same as Compd No. 36 | General Formula [IV] | Φ-COOH |
| 44 | O or S | $I^-$ or $ClO_4^-$ | $R_6 = L-A$<br>$R_7 = H$<br>$R_8 = \Phi\text{-}N(CH_3)_2$<br>$R_9 = H$<br>$R_{10} = \Phi\text{-}N(CH_3)_2$ | General Formula [II]<br>n = 0<br>Z = H | Φ-N(CH$_3$)$_2$ |
| 45 | O or S | $I^-$ or $ClO_4^-$ | $R_6 = L-A$<br>$R_7 = H$<br>$R_8 = \Phi\text{-}N(CH_3)_2$<br>$R_9 = H$<br>$R_{10} = \Phi\text{-}N(CH_3)_2$ | General Formula [II]<br>n = 1<br>Z = H | Φ-N(CH$_3$)$_2$ |
| 46 | O or S | $I^-$ or $ClO_4^-$ | $R_6 = L-A$<br>$R_7 = H$<br>$R_8 = \Phi\text{-}N(CH_3)_2$<br>$R_9 = H$<br>$R_{10} = \Phi\text{-}N(CH_3)_2$ | General Formula [III]<br>n = 1 | Φ-N(CH$_3$)$_2$ |
| 47 | O or S | $I^-$ or $ClO_4^-$ | $R_6 = L-A$<br>$R_7 = H$<br>$R_8 = \Phi\text{-}N(CH_3)_2$<br>$R_9 = H$<br>$R_{10} = \Phi\text{-}N(CH_3)_2$ | General Formula [IV] | Φ-N(CH$_3$)$_2$ |
| 48 | O or S | $I^-$ or $ClO_4^-$ | Same as Compd No. 44 | General Formula [II]<br>n = 0<br>Z = H | Φ-COOH |
| 49 | O or S | $I^-$ or $ClO_4^-$ | Same as Compd No. 44 | General Formula [II]<br>n = 1<br>Z = H | Φ-COOH |
| 50 | O or S | $I^-$ or $ClO_4^-$ | Same as Compd No. 44 | General Formula [III]<br>n = 1 | Φ-COOH |
| 51 | O or S | $I^-$ or $ClO_4^-$ | Same as Compd No. 44 | General Formula [IV] | Φ-COOH |
| 52 | O or S | $I^-$ or $ClO_4^-$ | $R_6 = A$<br>$R_7 = H$<br>$R_8 = -N(CH_3)_2$<br>$R_9 = H$<br>$R_{10} = \Phi\text{-}N(CH_3)_2$ | | A = COOH |
| 53 | O or S | $I^-$ or $ClO_4^-$ | $R_6 = A$<br>$R_7 = H$<br>$R_8 = -N(CH_3)_2$<br>$R_9 = H$<br>$R_{10} = \Phi\text{-}N(CH_3)_2$ | | A = Φ-COOH |
| 54 | O or S | $I^-$ or $ClO_4^-$ | $R_6 = \Phi$<br>$R_7 = H$<br>$R_8 = \Phi\text{-}N(CH_3)_2$<br>$R_9 = H$<br>$R_{10} = \Phi\text{-}N(CH_3)_2$ | | |
| 55 | O or S | $I^-$ or $ClO_4^-$ | $R_6 = \Phi\text{-}N(CH_3)_2$<br>$R_7 = H$<br>$R_8 = \Phi$<br>$R_9 = H$<br>$R_{10} = \Phi\text{-}N(CH_3)_2$ | | |

These compounds were synthesized in the following known methods. In this connection, the typical reaction operations were done in accordance with usual procedures.

A compound 7 was obtained by synthesizing the compound [i]

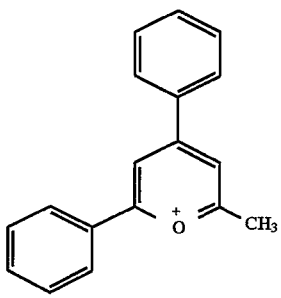 [i]

in accordance with a process described in W. Foerst et al., "New Methods of Preparative Organic Chemistry", Acad. Press (1964)"; reacting the synthesized compound [i] with

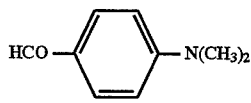

(p-N,N-dimethylaminobenzaldehyde) to form a compound; and then reacting the formed compound with desired anions. A compound 17 was obtained by reacting the above-mentioned compound [i] with

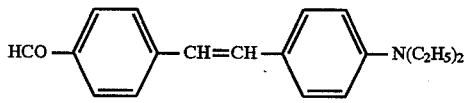

(p-diethylaminostyrylbenzaldehyde) to form a compound; and then reacting the formed compound with desired anions. Compounds 8 and 18 were synthesized by reacting the above-mentioned compound [i] with sodium hydrogen sulfide to form a compound [ii]

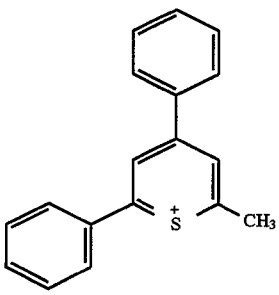 [ii]

and then treating this compound [ii] in the same manner as in the compounds 7 and 17.

A compound 5 was obtained by synthesizing a compound [iii]

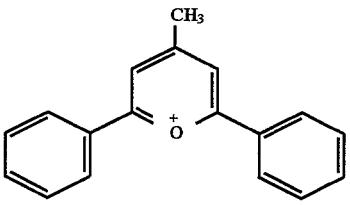 [iii]

from acetophenone and acetaldehyde in accordance with a process described in R. Wizinger et al., Helv. Chim. Acta., 39, p. 217 (1956) via the following route;

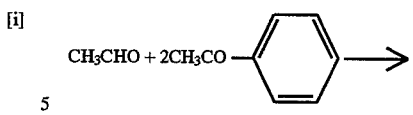 [i]

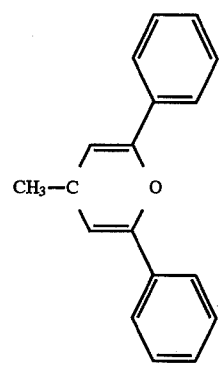

reacting this compound [iii] with p-dimethylaminobenzaldehyde to form a compound; and then reacting the formed compound with desired anions. A compound 15 was obtained by the same procedure as in the synthesis of the compound 5 except that p-dimethylaminobenzaldehyde was replaced with p-diethylaminostyrylbenzaldehyde. A compound 9 was obtained by the same procedure as in the synthesis of the compound 5 except that p-dimethylaminobenzaldehyde was replaced with p-dimethylaminocinnamic aldehyde. A compound 11 was obtained by the same procedure as in the synthesis of the compound 5 except that p-dimethylaminobenzaldehyde was replaced with the following compound:

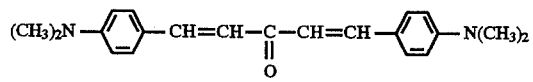

Compounds 6, 16, 10 and 12 were obtained by the same procedures as in the compound 5, 15 and 9, respectively, except that the above-mentioned compound [iii] was replaced with a compound [iv]

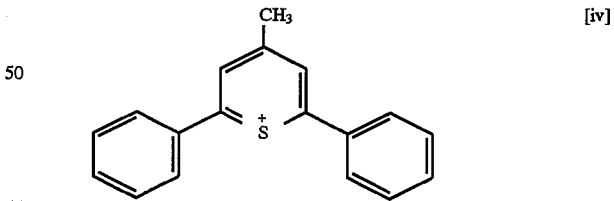 [iv]

which was obtained by reacting the above-mentioned compound [iii] with hydrated sodium sulfide.

A compound 4 was obtained by forming the compound 3 in the same manner as in the synthesis of the above-mentioned compound [iii] except that p-dimethylaminobenzaldehyde was replaced with a raw material acetaldehyde; reacting the compound 3 with sodium hydrogen sulfide to form a compound; and then reacting the formed compound with desired anions. A compound 13 was obtained by forming a compound [v]

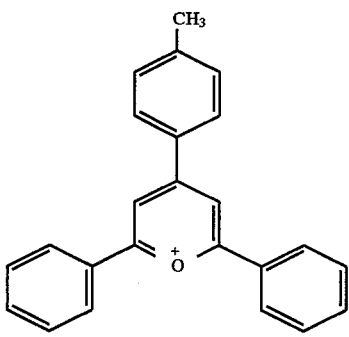

[v]

from p-methylbenzaldehyde and acetophenone in like manner; reacting the compound [v] with p-dimethylaminobenzaldehyde to form a compound; and then reacting the formed compound with desired anions. A compound 14 was obtained by the same procedure as in the compound 13 except that the above-mentioned compound [v] was replaced with a compound [vi]

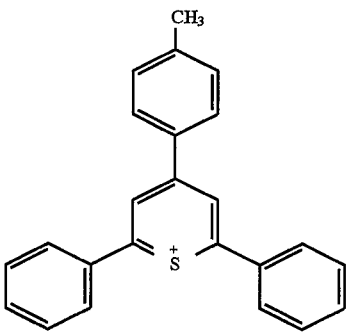

[vi]

which was formed by reacting the compound [v] with sodium hydrogen sulfide.

Compounds 19, 20 and 21 were each obtained by reacting the compound [i] or [ii], or the compound 1 or 2 and

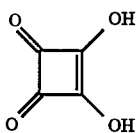

and then reacting the resulting compound with desired anions. Compounds 22, 23 and 24 were each obtained by reacting the compound [i] or [ii], or the compound 1 or 2 and

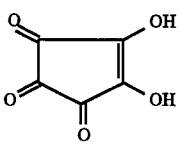

and then reacting the resulting compound with desired anions. Compounds 25 and 26 were each obtained by reacting the compound [i] or [ii] with

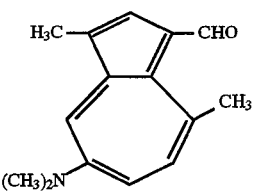

and then reacting the resulting compound with desired anions. Compounds 27, 28 and 29 were each obtained by reacting the compound [i] or [ii], or the compound 1 or 2 and triethoxymethane [$HC(OC_2H_5)_3$]; and then reacting the resulting compound with desired anions. Compounds 30, 31 and 32 were synthesized by reacting dimethylamino derivatives of the above-mentioned compounds [iii] and [iv] synthesized from p-dimethylamino acetophenone in the same manner as in the compounds [iii] and [iv], the compound [iii] or [iv] and triethoxymethane; and further reacting the resulting compound with desired anions.

Each of compounds 33 to 55 was synthesized in a manner as shown in the following:

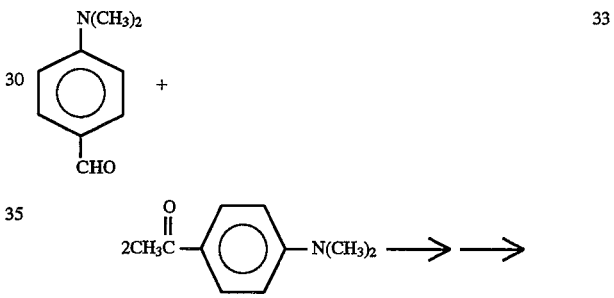

33

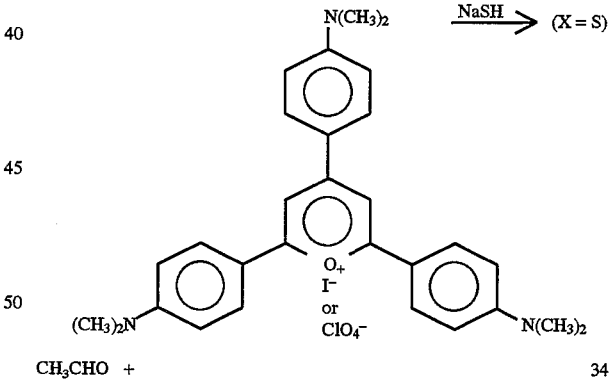

$CH_3CHO$ +

34

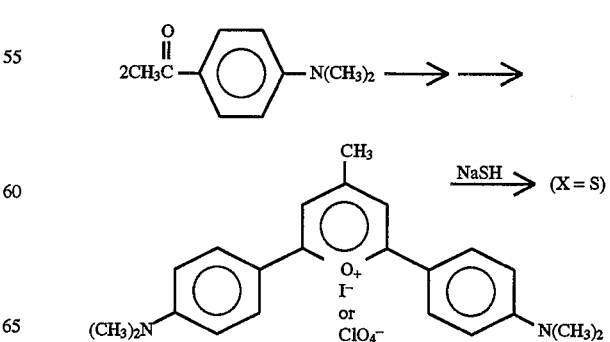

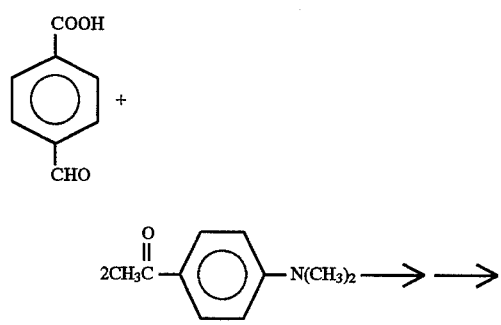
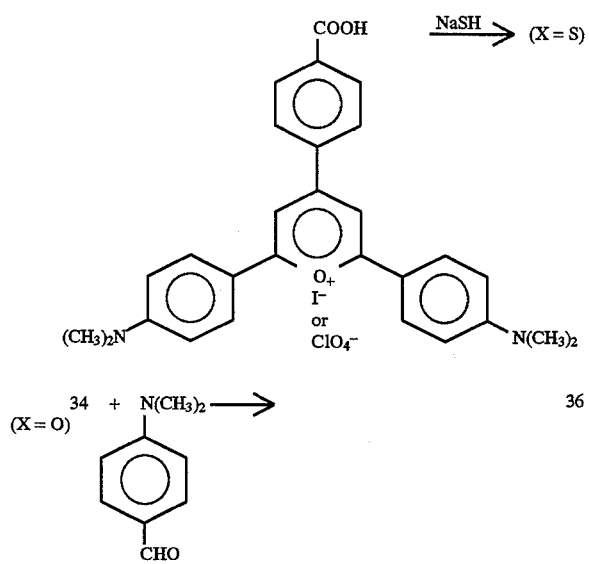
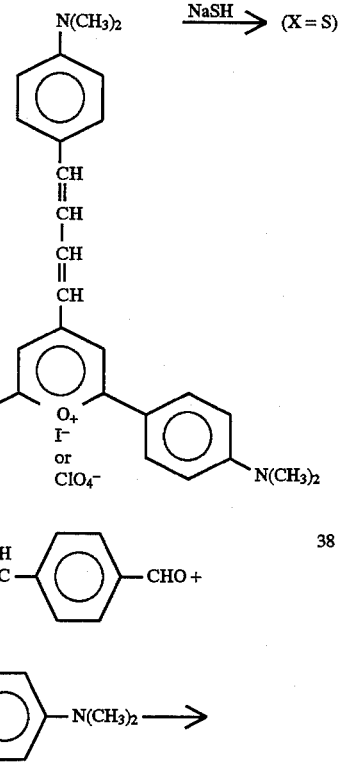
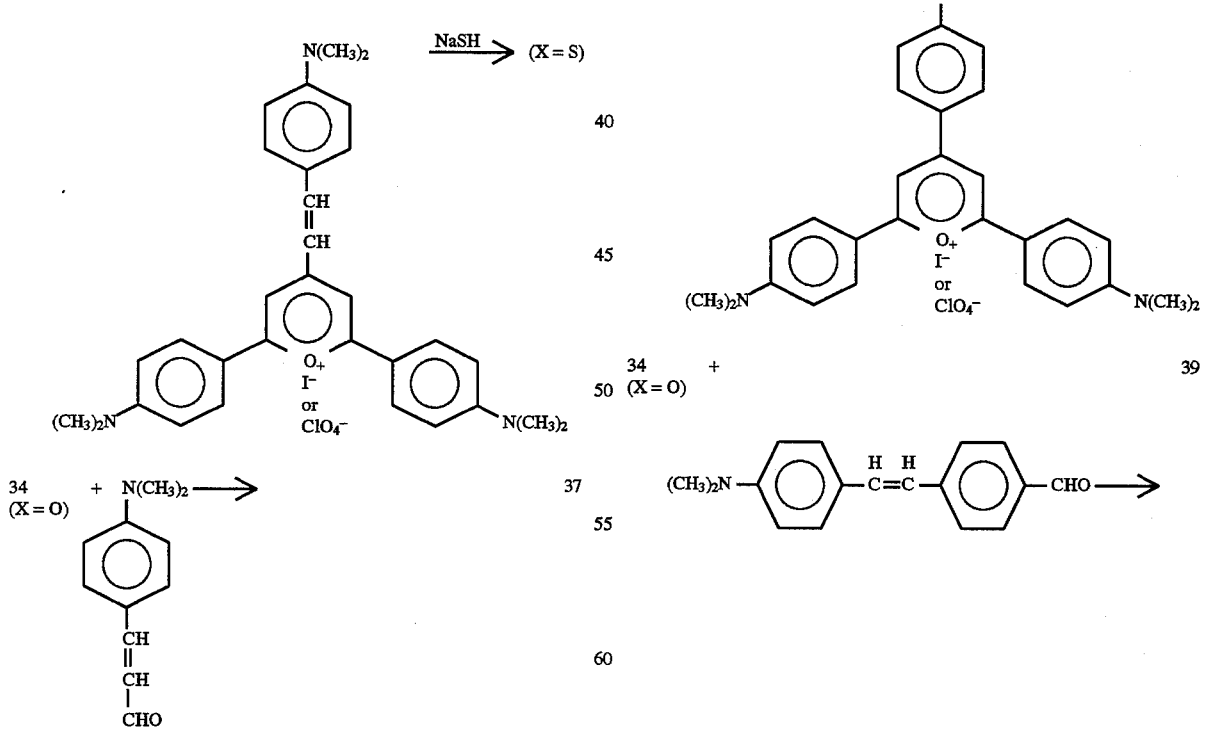

-continued

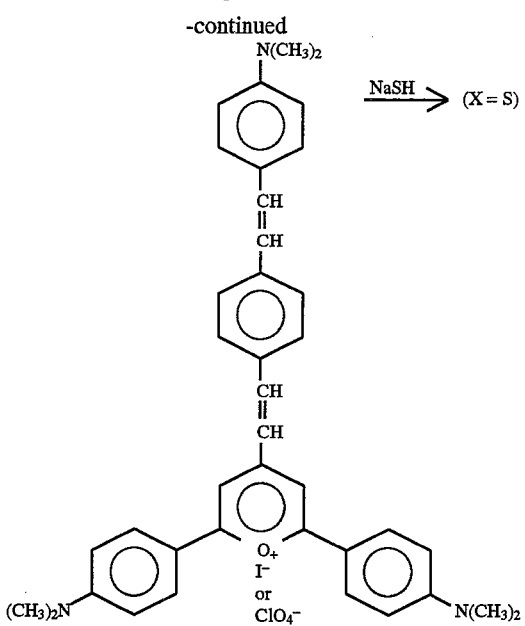

This compound was synthesized in the same manner as 36, except that

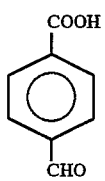

was employed intead of the material

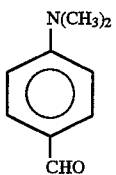

This compound was synthesized in the same manner as 37, except that

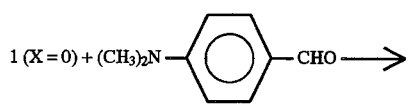

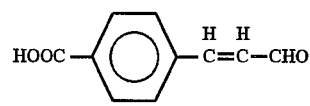

was employed instead of the material

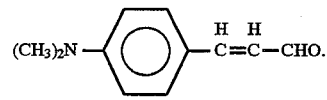

This compound was synthesized in the same manner as 38, except that

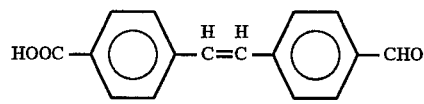

was employed instead of the material

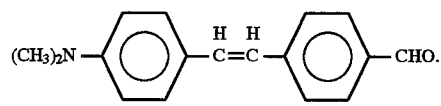

This compound was synthesized in the same manner as 39, except that

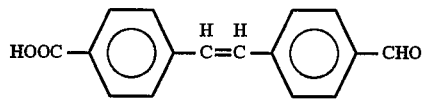

was employed instead of the material

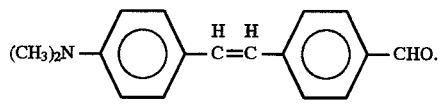

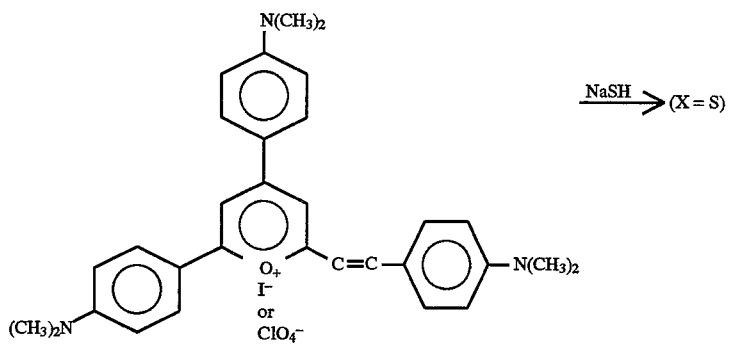

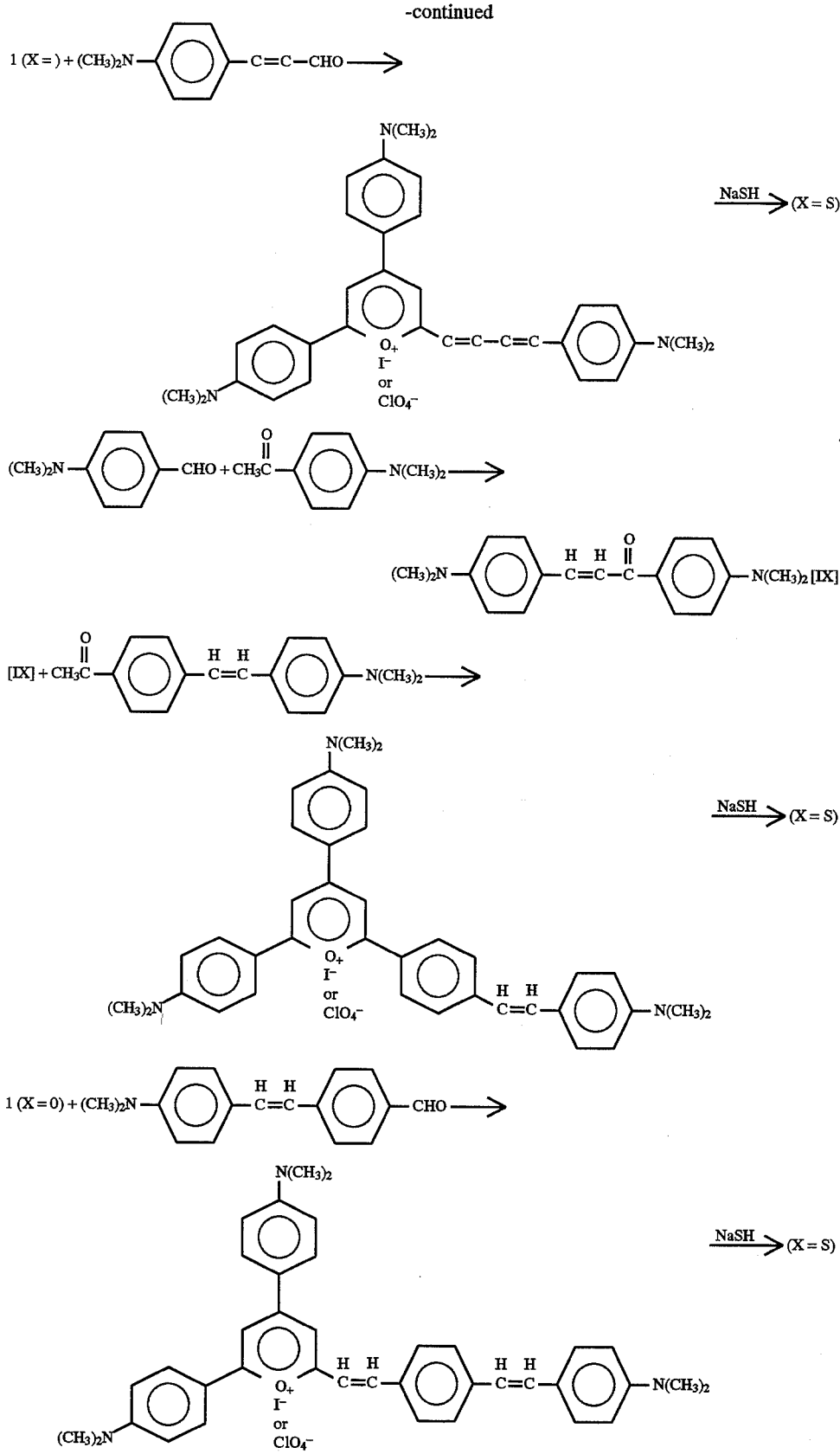
This compound was synthesized in the same manner as 44, except that

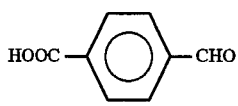
was employed instead of the material
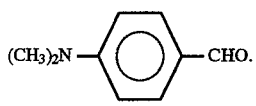
This compound was synthesized in the same manner as 45, except that
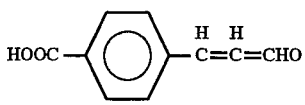
was employed instead of the material
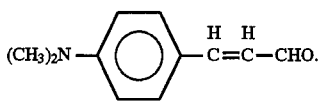
This compound was synthesized in the same manner as 46, except that
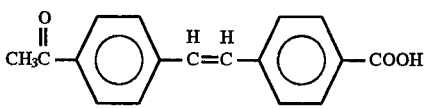
was employed instead of the material
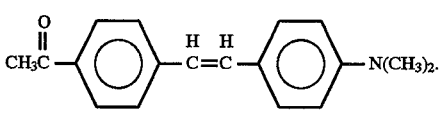
This compound was synthesized in the same manner as 47, except that
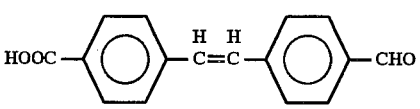
was employed instead of the material
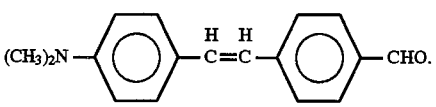
52
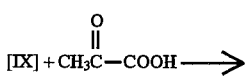
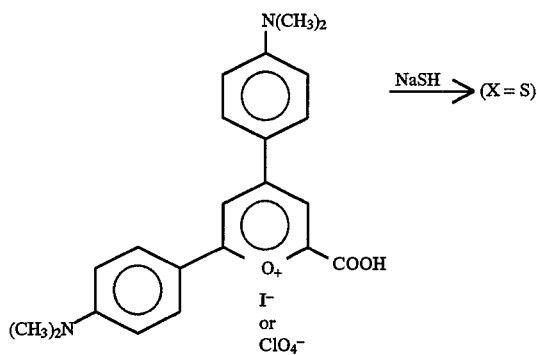
53
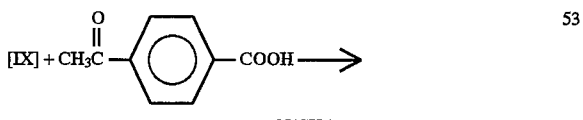
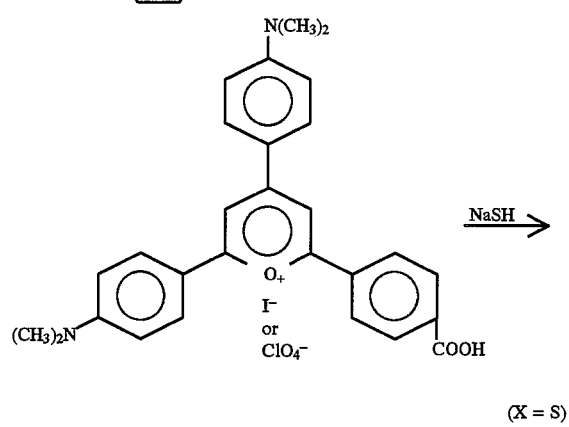

-continued

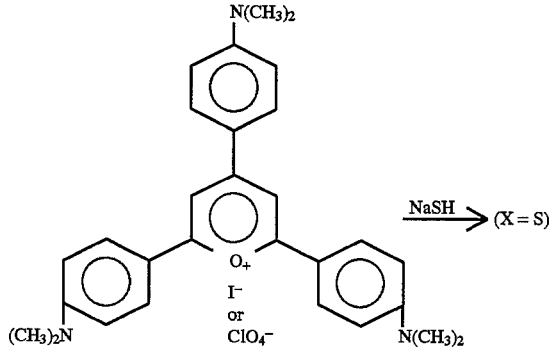

EXAMPLE 3

A compound 1 obtained in Example 1 was dissolved in a 10 mM phosphoric acid buffer solution containing 10% acetonitrile, and the solution was then regulated so that the final concentration of the compound 1 might be $3\times10^{-5}$M, to prepare a sample I. The absorption spectrum of this sample I was measured in a usual manner by the use of a part of the sample I with a spectrophotometer, so that the results shown by a curve A in FIG. 1 were obtained.

Next, a salmon sperm DNA (made by Sigma Co., Ltd.) was dissolved in a TE buffer solution (10 mM of tris-1 mM EDTA) and then purified by phenol extraction. For easy handling, the purified solution was further subjected to a digestion treatment using the restriction enzyme EcoRI to obtain a DNA solution. A part of this DNA solution was mixed with a part of the sample I, and the solution was then regulated so that the final concentration of DNA might be 50 μg/ml and so that the final concentration of the compound 1 might be $1\times10^{-4}$M, to obtain a sample II. The absorption spectrum of the sample II was measured in a usual manner by the use of a part of the sample II, so that the results shown by a curve B in FIG. 1 were obtained. That is, the absorption peak of this compound was shifted as much as 20–30 nm to a longer wavelength side by interaction with DNA. This was due to typical characteristics of an intercalater.

Figure 2:
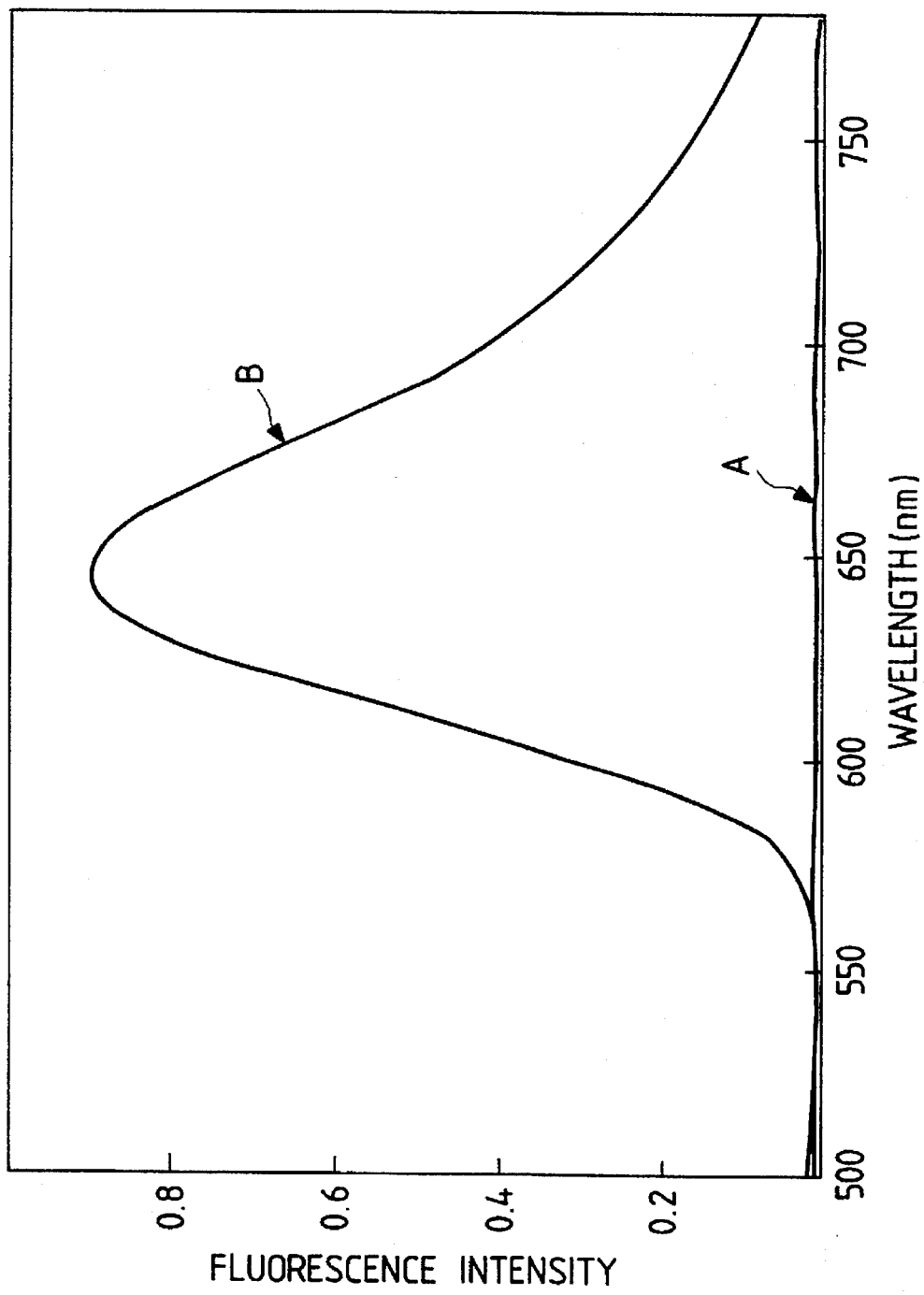
FIG. 2 is a graph showing fluorescence spectra obtained in Example 3, and A denotes the fluorescence spectrum in the absence of DNA and B denotes the fluorescence spectrum in the presence of DNA (50 μg/ml).

The fluorescence spectrum of the sample I was measured in a usual manner by the use of a part of the sample I, and as a result, when DNA was absent, a weak peak was detected at about 650 nm by excitation at 550 nm (refer to a curve A in FIG. 2). Next, the fluorescence spectrum of the sample II was similarly measured by the use of a part of the sample II, and as a result, a peak having fluorescence intensity which was about 100 times as much as the case of DNA being absent was detected in the vicinity of 650 nm by excitation at the same wavelength (refer to a curve B in FIG. 2). The above-mentioned results indicate that the compound I was a strong intercalater.

Figure 3:
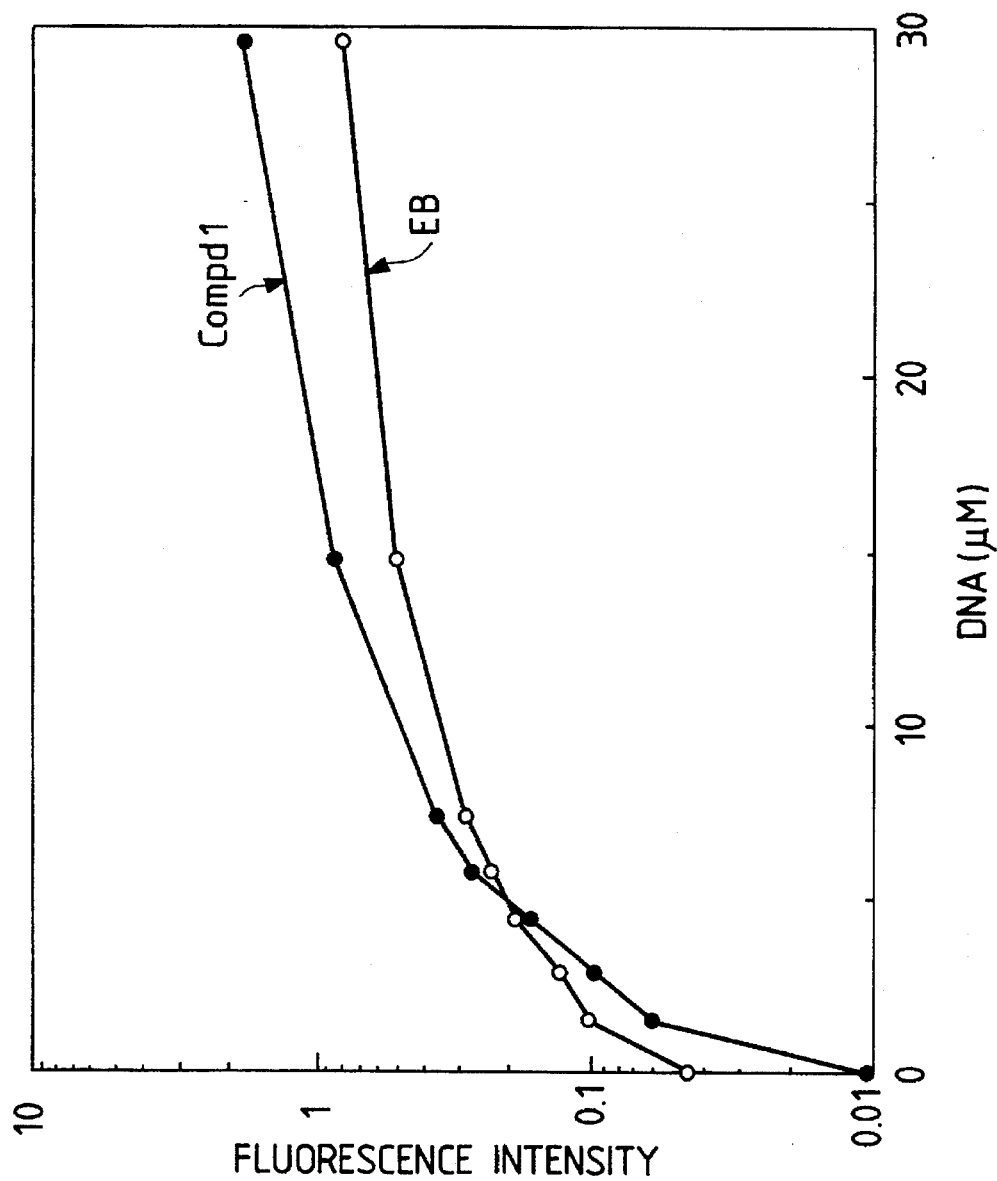
FIG. 3 is a graph showing the change of fluorescence intensity with respect to DNA concentration obtained in Example 3 and Comparative Example 1.
Figure 4:
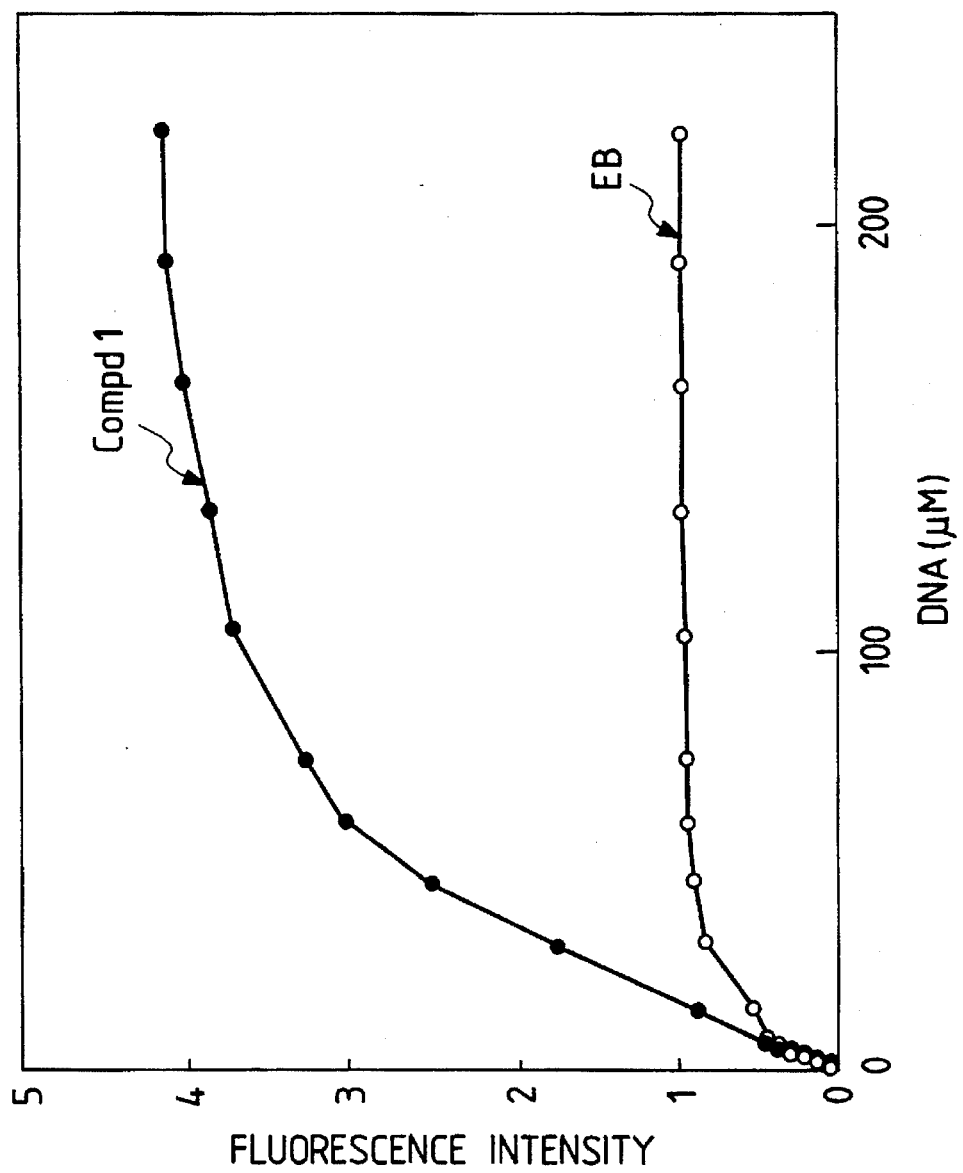
FIG. 4 is a graph showing the change of fluorescence intensity with respect to DNA concentration obtained in Example 3 and Comparative Example 1.

Next, solutions containing the compound 1 at a concentration of $5\times10^{-6}$M and different DNA concentrations were prepared by the use of the previously prepared DNA solution, the compound 1 and a 10 mM phosphoric acid buffer solution containing 10% of acetonitrile. Fluorescence intensities of the thus prepared solutions were measured in a usual manner to determine changes of the fluorescence intensities to the DNA concentrations. The obtained results are shown in FIGS. 3 and 4. The fluorescence intensity enhances with the increase of the DNA concentration, and it was at most about 400 times larger than when DNA was absent. In this case, as excitation light, there was used light from a Xe lamp light source from which ultraviolet portion was removed by a low cut filter of 480 nm.

Comparative Example 1

Changes of fluorescence intensities to DNA concentrations were determined in accordance with the same procedure as in Example 3 by the use of ethidium bromide (EB) which was known as an intercalater. The results are shown in FIGS. 3 and 4.

As is apparent from the results in FIG. 3, the fluorescence intensity of a compound 1 is substantially zero in the absence of DNA, but in the case of EB, it is high even in the absence of DNA. Furthermore, for example, at a DNA concentration of 4 μM, the fluorescence of the compound 1 increases about 17 times, whereas the fluorescence of EB increases about 4 times. Therefore, it is apparent that in the presence of DNA, S/N of the compound 1 is much better than that of EB. Hence, when the compound 1 is used as a stain for a nucleic acid, the high-sensitive detection of the nucleic acid is possible on very low background, and even in a low-concentration region of DNA, the detection with the high sensitivity is possible.

Moreover, as is apparent from the results in FIG. 4, the compound 1 can obtain the fluorescence intensity 4 times as much as EB, so long as visible light is used as excitation light, and so when the compound 1 is used, the nucleic acid can be detected with the high sensitivity.

EXAMPLE 4

A DNA size marker ξ/Hind III digest-ΦX174/Hae III digest (made by Toyobo Co., Ltd.) was used to prepare solutions having various concentrations of from 100 ng to 0.1 ng in all, and separation was then carried out by 0.8% agarose gel electrophoresis. Next, an acetonitrile solution of a compound 1 was dissolved in distilled water so that the final concentration of the dyestuff might be $1\times10^{-6}$M and so that the concentration of acetonitrile might be 10%, and the Gel which had undergone the electrophoresis was immersed in this acetonitrile solution for about 2 minutes.

One side of a transilluminator-like box was covered with a band pass filter of from 480 to 590 nm, and the stained Gel was then put on the filter, and another filter for fluorescence detection (a band pass filter of from 620 to 710 nm) was further superposed upon the gel. Afterward, the gel was irradiated with a halogen lamp, and as this time, the developed pattern of DNA could be directly confirmed by the naked eye and the stained band where 0.05 ng of DNA was considered to be present could be directly confirmed by the naked eye. In addition, photographs taken by a Polaroid camera were also Good. In this case, sensitivity was ten or more times better than in the case that the gel stained with conventional ethidium bromide was excited with ultraviolet rays (a transilluminator was used).

EXAMPLE 5

DNA size markers having various concentrations were prepared by the same procedure as in Example 4, and DNA fragments were separated in a 1% agarose gel (5×6 cm) by the use of a small-sized electrophoresis device. Next, a compound 1 was dissolved in the same manner as in Example 4, and the gel which had undergone the electrophoresis was then immersed in the solution of the compound 1. Afterward, the same band pass filter as in Example 4 was set instead of a glass above the surface of a strobe which was an excitation source. The stained gel was put on the filter, and photographs were taken by a Polaroid camera equipped with a band pass filter for fluorescence detection, the camera being connected to the strobe. Preferably, a shutter speed was 1 second and an aperture was about 1/16. Detection sensitivity was the same as in Example 4.

EXAMPLE 6

Solutions having various concentrations were prepared using a DNA size marker ΦX174/Hae III digest (made by Toyobo Co., Ltd.) by the same procedure as in Example 4, and separation was then made by 8% polyacrylamide gel electrophoresis. Next, a compound 10 was dissolved in the same manner as in Example 4, and the gel which had undergone the electrophoresis was then immersed in the solution of the compound 10. Afterward, a semiconductor laser (680 nm, made by Hitachi, Ltd.) was used as an excitation source and a band pass filter (a wavelength region of from 700 to 800 nm) was set in front of a photomultiplier, and fluorescence intensity was then determined by scanning on the gel. The intensity of each band was directly proportional to the length of the DNA fragment of the size marker, and quantitative handling was possible till the highest concentration, 1.3 kb (25 ng).

EXAMPLE 7

An M13 mp 18 single-strand DNA was used as the model of a target nucleic acid, and a 20-mer oligonucleotide having the following sequence which was complementary to the base sequence of the target nucleic acid was synthesized as a probe I by the use of a DNA synthesizer (trade name 381A, made by ABI Co., Ltd.):

5'GTTGTAAAACGACGGCCAGT3'SEQ IS NO:1

Moreover, a 20-mer for a control test consisting of T alone was similarly synthesized as a probe II.

The probe I and the M13 mp 18 single-strand DNA were added to a solution of 1 mM phosphoric acid buffer solution (pH=7.0), 145 mM of NaCl and 5 mM KCl so that the respective final concentrations the probe I and the single-strand DNA might be 10 µg/ml, and they were reacted with each other to obtain a specimen I. In addition, similar reaction was carried out using the probe II in place of the probe I to obtain a specimen II.

Next, an acetonitrile solution of a compound 1 was added to each of the specimens I and II so that the final concentration might be $3 \times 10^{-5}$M, and the solution was irradiated with light from a tungsten lamp. As a result, in the case of the specimen I, red luminescence was confirmed, but in the case of the specimen II, a transparent state was maintained. The results indicate that the detection of a hybrid of the probe and the target nucleic acid in the solution system can be achieved without B/F separation.

EXAMPLE 8

Figure 5:
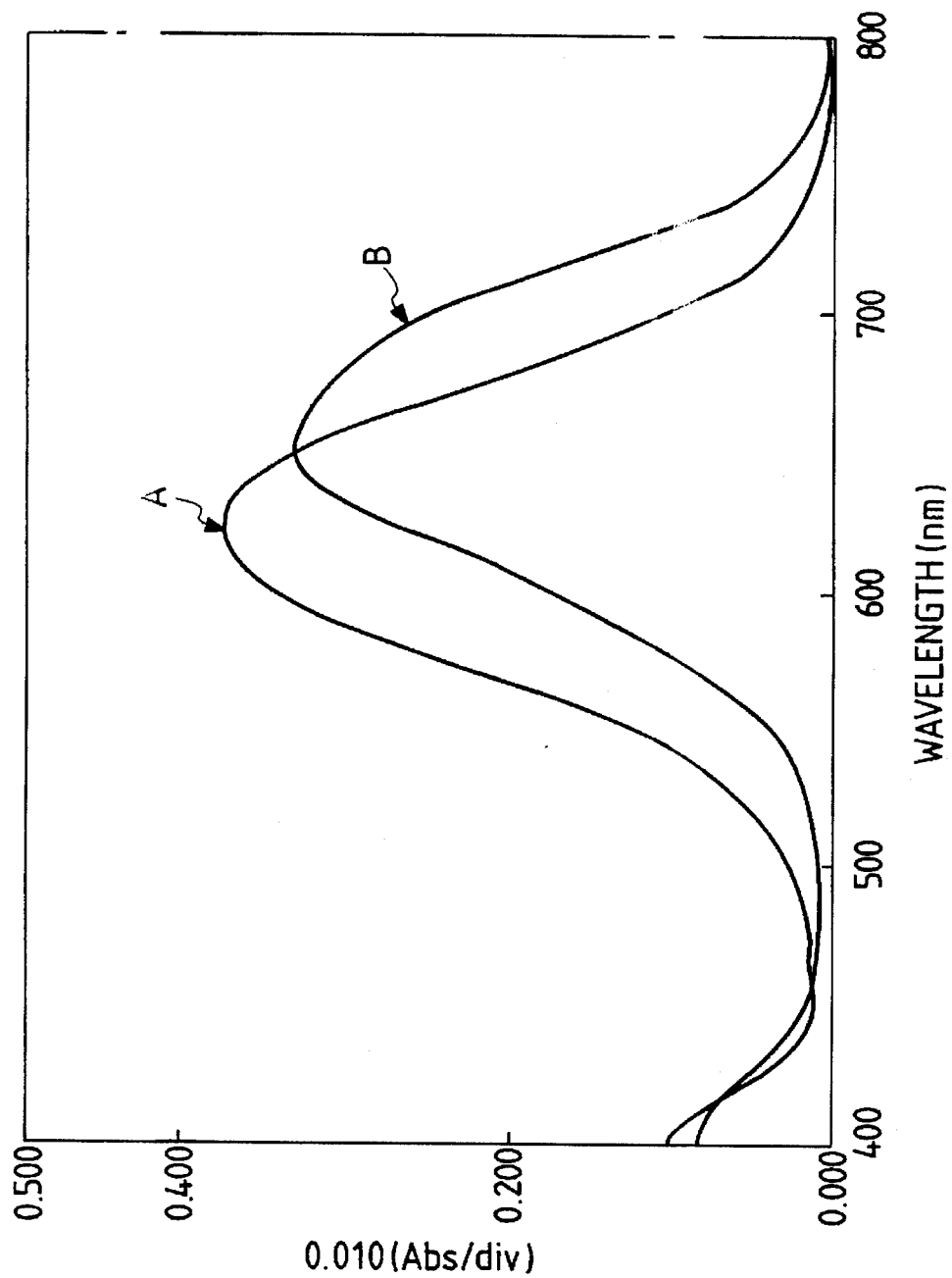
FIG. 5 is a graph showing the shift of an absorption peak in Example 8, and A denotes an absorption spectrum in the absence of DNA and B denotes an absorption spectrum in the presence of DNA (50 μg/ml).

For a compound 12, the same experiment as in Example 3 was carried out. That is, a suitable amount of the compound 12 was dissolved in a 100 mM acetic acid buffer solution containing 10% of acetonitrile, and the solution was then regulated so that the most absorption maximum might be about 0.4. As shown in FIG. 5, when DNA was absent, the compound 12 had the absorption maximum at 625 nm.

A DNA solution prepared in Example 3 was added to the solution of the compound 12 so that the final concentration might be 50 µg/ml, and at this time, the absorption was shifted as much as 35 nm to a long wavelength side and the compound 12 had absorption maximum at 660 nm. In addition, its absorbance decreased, and a hypochromic effect was shown, which were typical characteristics of an intercalater.

Figure 6:
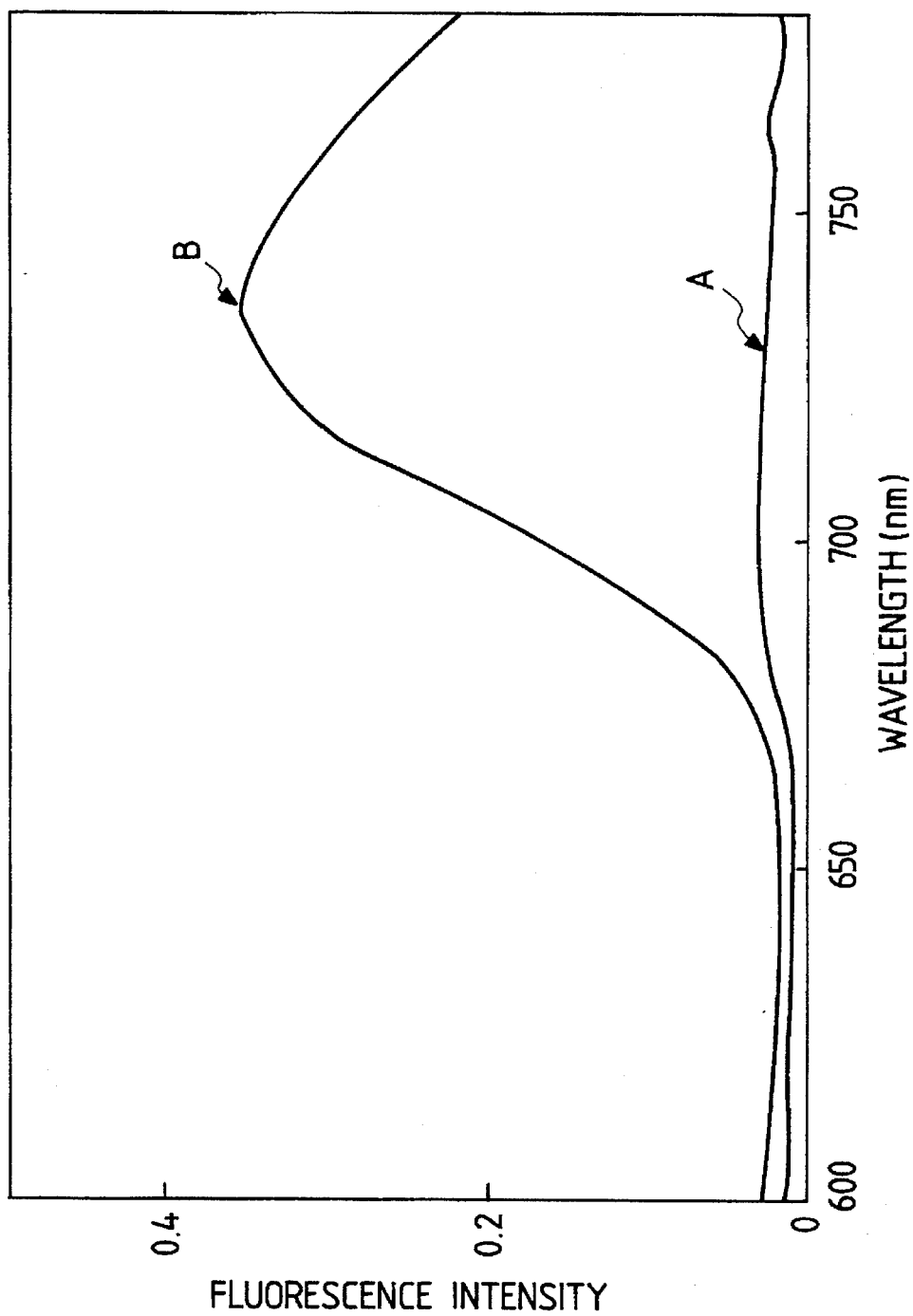
FIG. 6 is a graph showing fluorescence spectra obtained in Example 8, and A denotes the fluorescence spectrum in the absence of DNA and B denotes the fluorescence spectrum in the presence of DNA (50 μg/ml).

Fluorescence spectra were measured in the presence and the absence of DNA in the same manner as in Example 3, and in consequence, the results shown in FIG. 6 were obtained. As shown in FIG. 6, in the case of no DNA, weak fluorescence was observed at about 690 nm when excitation was given by a xenon lamp. Next, DNA was added to the solution so that the final concentration might be 50 µg/ml, and in this case, the wavelength of the fluorescence was 735 nm, and its fluorescence intensity increased about 10 times as much as the case of no DNA. That is, it was confirmed that the compound 12 was an intercalater. By the use of this compound 12, the detection of DNAs in Examples 4 and 7 could be carried out.

EXAMPLE 9

Figure 7:
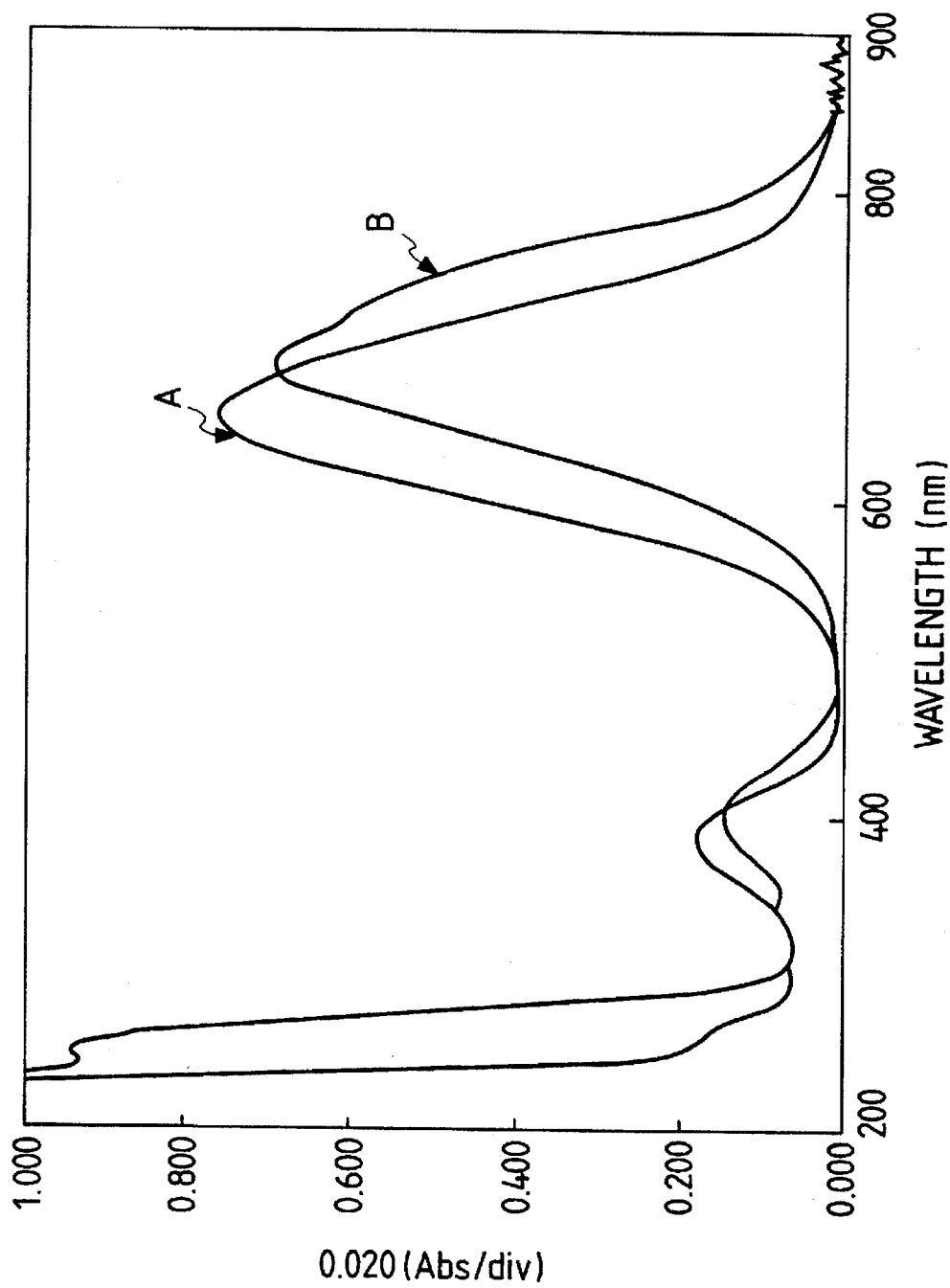
FIG. 7 is a graph showing the shift of an absorption peak in Example 9, and A denotes an absorption spectrum in the absence of DNA and B denotes an absorption spectrum in the presence of DNA (50 μg/ml).

For a compound 6, the same experiment as in Example 3 was carried out. That is, a suitable amount of the compound 6 was dissolved in a 10% aqueous acetonitrile dimethyl sulfoxide solution, and the solution was then regulated so that the most absorption maximum might be about 0.4. As shown in FIG. 7, when DNA was absent, the compound 6 had the absorption maximum at 660 nm.

A DNA solution prepared in Example 3 was added to the solution of the compound 6 so that the final concentration might be 50 µg/ml, and at this time, the absorption was shifted as much as 30 nm to a long wavelength side and the compound 6 had absorption maximum at 690 nm. In addition, its absorbance decreased, and a hypochromic effect was shown, which were typical characteristics of an intercalater.

Figure 8:
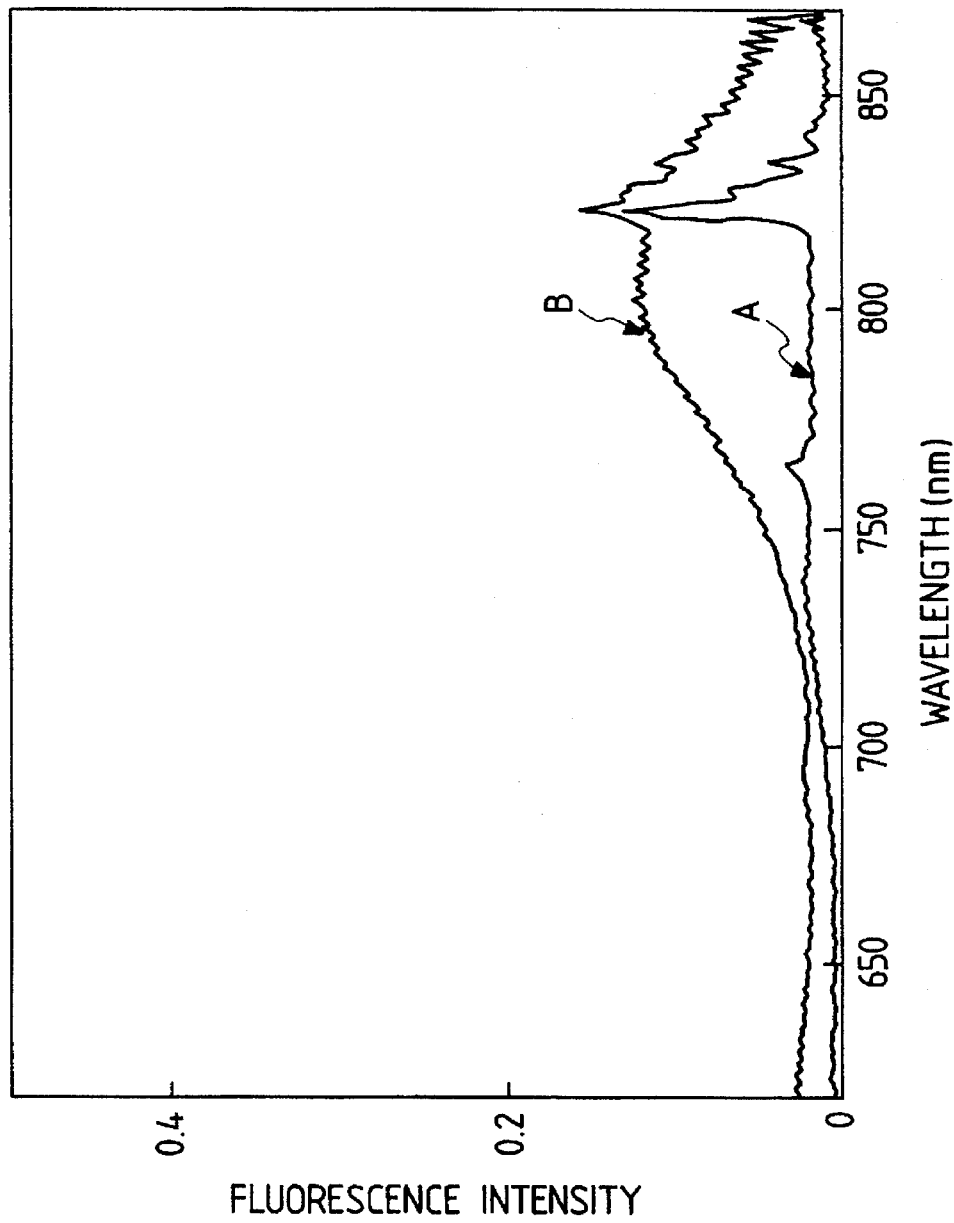
FIG. 8 is a graph showing fluorescence spectra obtained in Example 9, and A denotes the fluorescence spectrum in the absence of DNA and B denotes the fluorescence spectrum in the presence of DNA (50 μg/ml).

Fluorescence spectra were measured in the presence and the absence of DNA in the same manner as in Example 3, and in consequence, the results shown in FIG. 8 were obtained. As shown in FIG. 8, in the case of no DNA, weak fluorescence was observed at about 735 nm when excitation was given by a xenon lamp. Next, DNA was added to the solution so that the final concentration might be 50 µg/ml, and in this case, the wavelength of the fluorescence was 800 nm, and its fluorescence intensity increased about 7 times as much as the case of no DNA. That is, it was confirmed that the compound 6 was an intercalater. By the use of this compound 6, the detection of DNAs in Examples 4 and 7 could be carried out.

EXAMPLE 10

Figure 9:
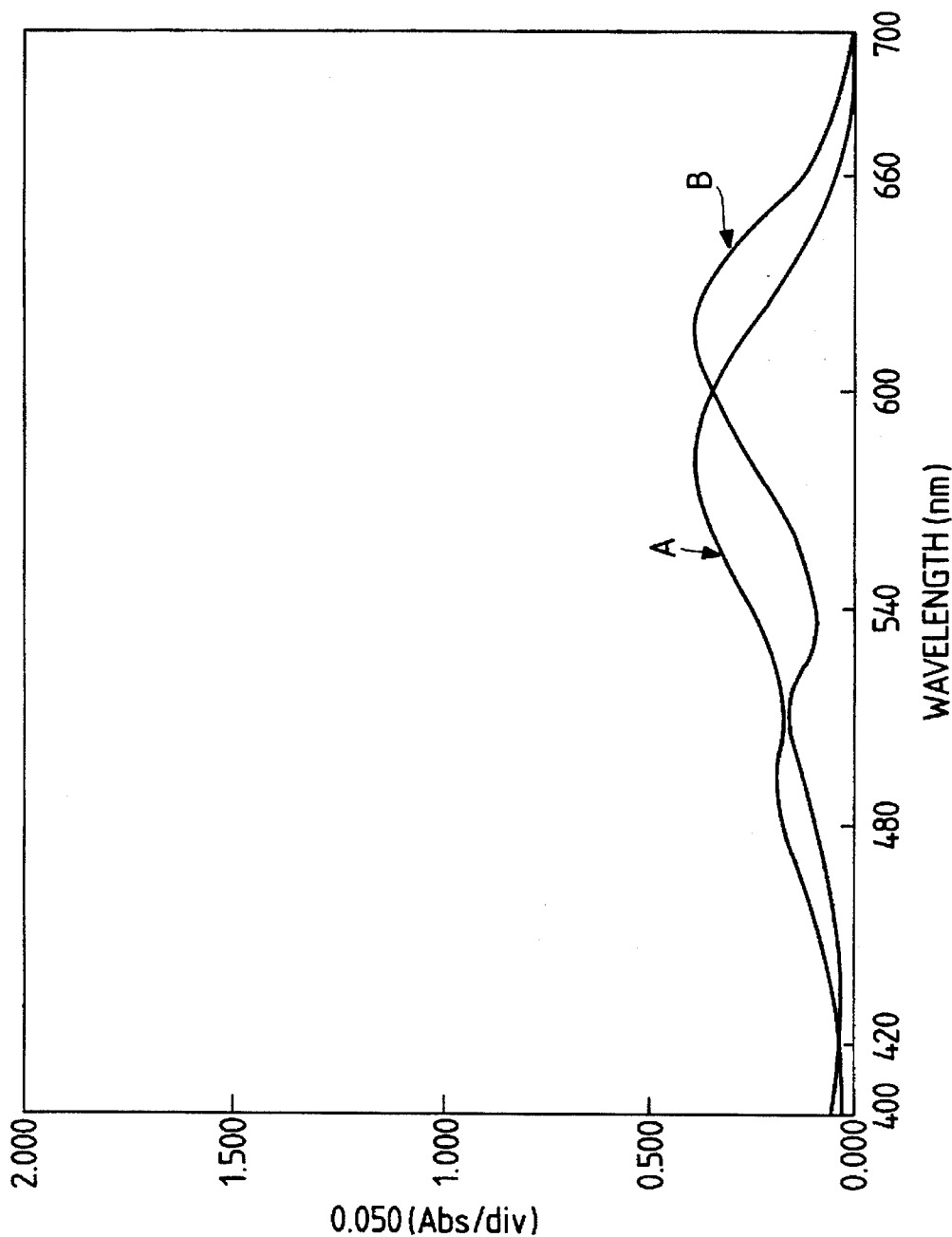
FIG. 9 is a graph showing the shift of an absorption peak in Example 10, and A denotes an absorption spectrum in the absence of DNA and B denotes an absorption spectrum in the presence of DNA (50 μg/ml).

A compound 2 was dissolved in a 10 mM phosphoric acid buffer solution containing 10% of acetonitrile, and the solution was then regulated so that the final concentration might be $5 \times 10^{-5}$M. As shown in FIG. 9, when DNA was absent, the compound 2 had absorption in the range of from 520 to 660 nm, and its absorption maximum was at 580 nm.

Figure 10:
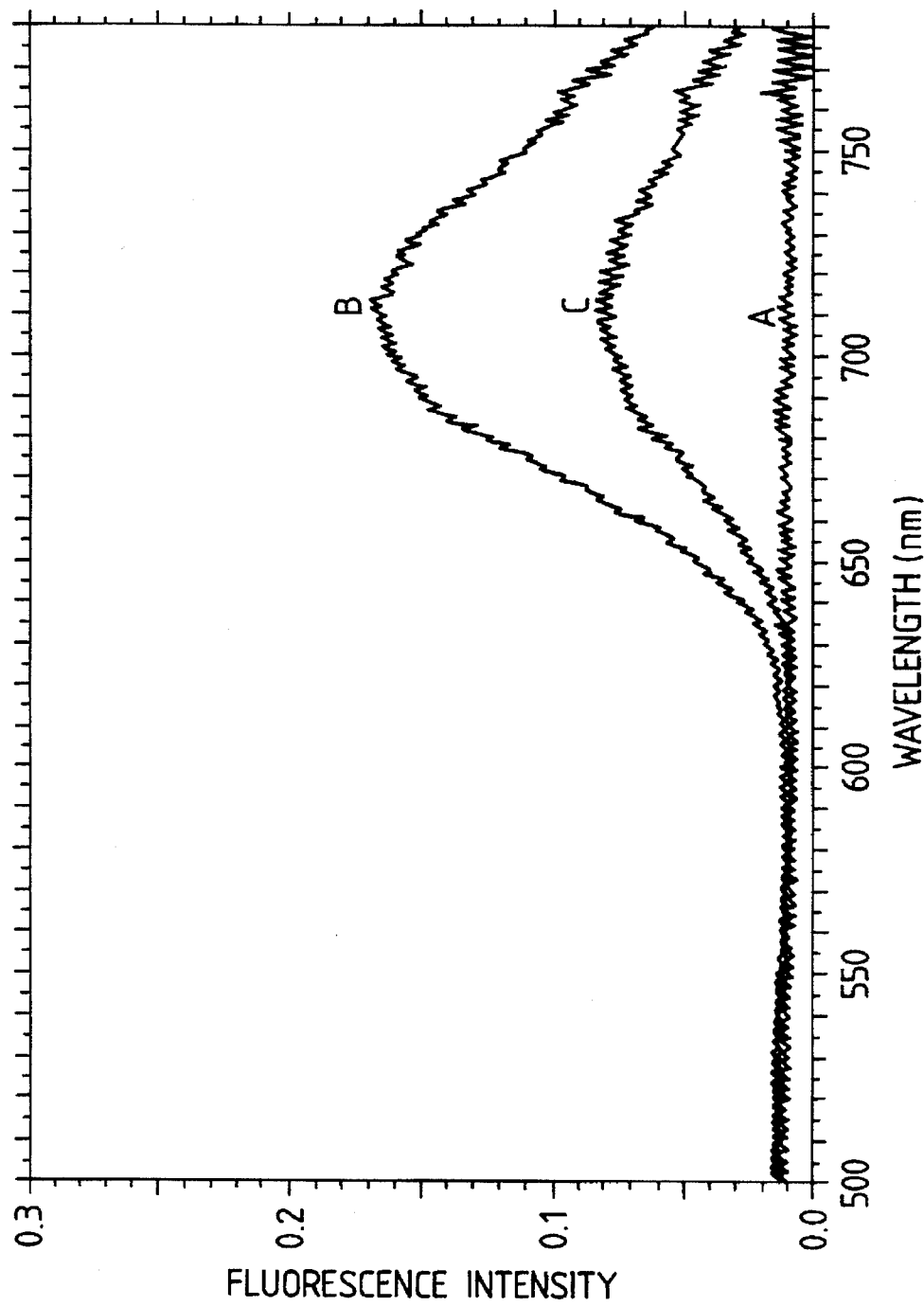
FIG. 10 is a graph showing fluorescence spectra obtained in Example 10. Here, A denotes the fluorescence spectrum in the absence of DNA, B denotes the fluorescence spectrum in the presence of DNA (10 μg/ml), and C denotes the fluorescence spectrum in the presence of DNA (5 μg/ml).

A DNA solution prepared in the same manner as in Example 3 was added to the solution of the compound 2 so that the final concentration might be 50 µg/ml, and at this time, the absorption was shifted as much as 30–40 nm to a long wavelength side, which was typical characteristics of an intercalater. Fluorescence spectra were similarly measured, and in consequence, the results shown in FIG. 10 were obtained. As shown in FIG. 10, in the case of no DNA, a peak was observed at about 700 nm when excitation was given by a xenon lamp.

Figure 11:
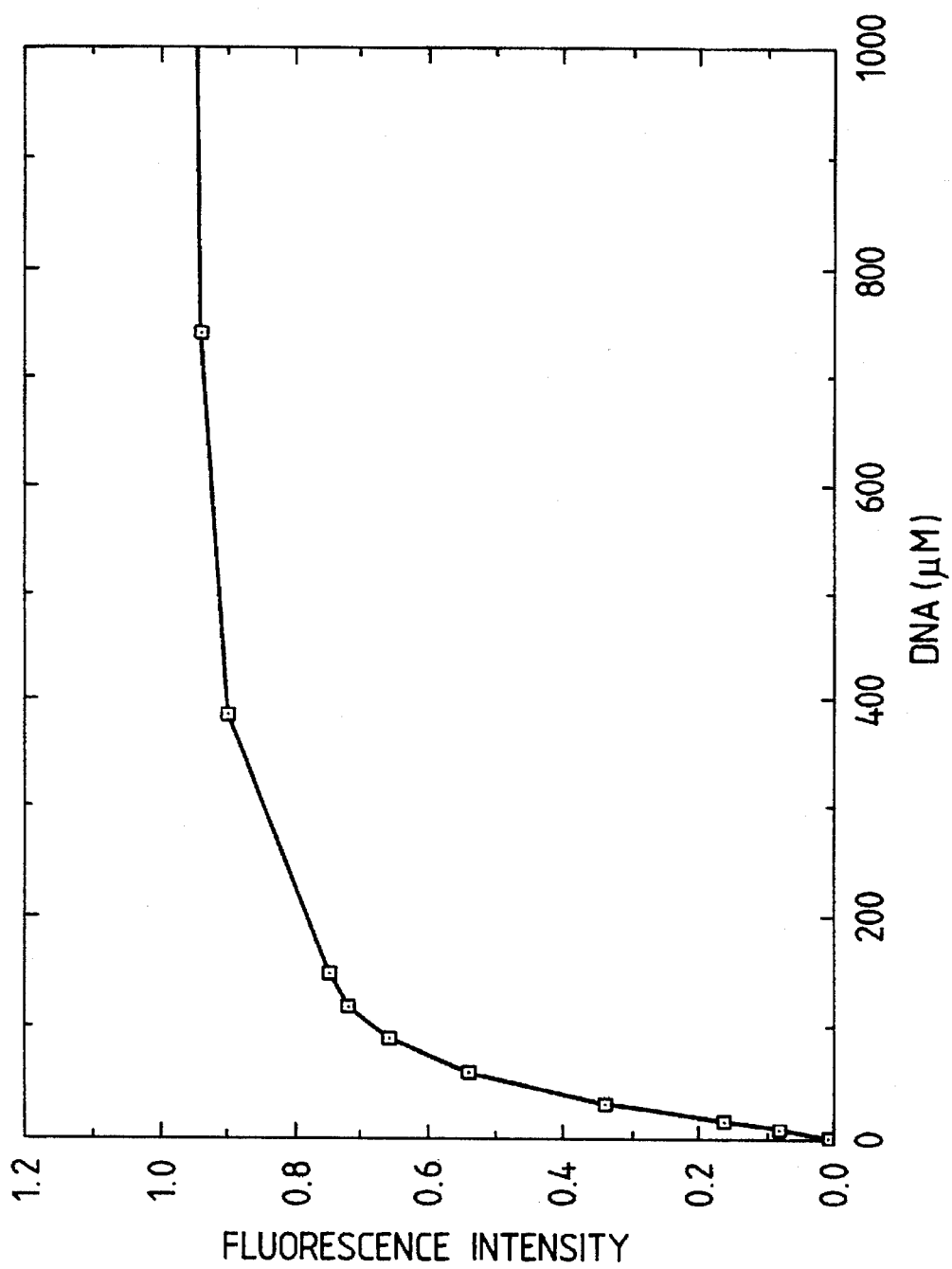
FIG. 11 is a graph showing the change of fluorescence intensity with respect to DNA concentration obtained in Example 10.

Next, the compound 2 was dissolved in a 10 mM phosphoric acid buffer solution containing 10% of acetonitrile, and the solution was then regulated so that the final concentration might be $1 \times 10^{-6}$M. DNA was then added to the solution at various concentrations to prepare solutions having different DNA concentrations. The fluorescence intensities of the thus prepared solutions were measured in a usual manner to inspect changes of the fluorescence intensities to the DNA concentrations. The results are shown in FIG. 11. The fluorescence intensities enhanced with the increase of the DNA concentration, and it enhanced at most about 100 times as much as the case of no DNA.

It was confirmed from the above-mentioned results that the compound 2 was the strong intercalater.

EXAMPLE 11

With regard to the shift of absorption maximum and the enhancement of fluorescence intensity of other compounds shown in Table 1 in the presence of DNA, measurement was made by the same procedure as in Examples 3, 8 and 9. Typical examples of the obtained results are shown in Table 2. In this connection, each degree of the enhancement is a value at the time of the final concentration of DNA being 50 µm/ml.

TABLE 2

| Compound No. | Absorption Maximum (λmax) | | Fluorescence Intensity | |
| --- | --- | --- | --- | --- |
| | in the absence of DNA | in the presence of DNA | $\lambda_{em}$ | Degree of Enchancement |
| 1 | 540 nm | 560 nm | 650 nm | 100 times |
| 2 | 580 nm | 620 nm | 700 nm | 60 times |
| 3 | 535 nm | 570 nm | 640nm | 13.6 times |
| 4 | 575 nm | 610 nm | 705 nm | 10 times |
| 6 | 660 nm | 690 nm | 800 nm | 7 times |
| 8 | 650 nm | 670 nm | weak | — |
| 9 | 660 nm | 720 nm | 750 nm | 16 times |
| 11 | 625 nm | 660 nm | 735 nm | 10 times |
| 15 | 670 nm | 680 nm | 820 nm | 5 times |
| 16 | 690 nm | 720 nm | 825 nm | 5 times |
| 17 | 690 nm | 720 nm | weak | — |

EXAMPLE 12

(Live cell staining of cultured cells)

L cells (NCTC clone 929, ATCC No. CCL1, Sanford, K. K., Earle, W. R., Likely, G. D.: J. Natl. Cancer Inst., 9.229–246, 1948) were used as cultured cells, and an ordinary culture method was employed and Eagle's MEM of an eagle (made by Nissui Co., Ltd.)+10% FCS was used as a culture medium.

Cultivation was carried out in a $CO_2$ incubator at 37° C., and the culture medium in which a cell density became about $1.2 \times 10^6$ cells/cm² was used for staining.

2-methyl-4,6-bis-(4-N,N-dimethylaminophenyl)pyrylium iodide [compound 1 wherein (Y was I)] was dissolved in ethanol (for fluorescence analysis) so that the concentration of the compound 1 might be 200 µg/ml. The resulting solution was passed through a filter having a pore size of 0.22 µm to sterilize the same and to remove particles therefrom, thereby obtaining a stock solution for a staining solution of the present invention.

As the cells to be stained, unfixed live cells were used. That is, the above-mentioned stock solution was directly aseptically added to the culture medium of the culture cells in accordance with a usual culture operation. In this experiment, the culture medium was regulated so that the final concentration of the compound 1 might be 100 ng/ml (the final ethanol concentration=0.5%).

The culture medium was statically incubated for 5 minutes in the $CO_2$ incubator, and fluorescence observation was then carried out. This fluorescence observation was made in the culture medium still containing the compound 1, i.e., in a state where the cells were present in the staining solution. In this observation, an inverted type refractive fluorescence microscope (trade name IMT-2, made by Olympus Optical Co., Ltd.) was used. As a result, cell nuclei were sharply stained, and fluorescence images emitting clear fluorescence were observed. In addition, the fade phenomenon of the fluorescence was not observed, and the fluorescence of the staining solution which became background was scarcely observed.

Moreover, after the observation, the staining solution was replaced with a usual culture medium, and the cultivation was then continued. The cells were normally propagated, and after subcultures, it was possible to stain them again and to observe the fluorescence.

In the case of the compound 1 which was the dyestuff which was used in this example, the excitation light and the fluorescence were in a relatively long wavelength region, and hence, in the fluorescence observation for a long time in one visual field, a bad influence such as heat generation on the cells could be presumed. However, any particular influence was not present owing to the very low concentration, the inhibition of the excitation light by much fluorescence, and the like.

Comparative Example 2

[Live cell staining of cultured cells by ethidium bromide (EB)]

Cells to be stained were prepared by the same procedure as in Example 12.

A dyestuff (EB) is usually used in the state of an aqueous solution, but in this experiment, it was used in the state of an ethanol solution for the sake of coordination with Example 12. The concentration of the dyestuff solution was set to 200 µg/ml, as in Example 12. The dyestuff solution was passed through a filter having a pore size of 0.22 µm to sterilize the same and to remove particles therefrom, thereby obtaining a stock solution for a staining solution for comparison.

Staining was also carried out by directly adding the stock dyestuff solution to the culture medium, as in Example 2.

After the addition of the dyestuff, statical incubation was carried out for four different times, i.e., 5 minutes, 15 minutes, 1 hour and 1.5 hours, and the specimens were then observed. A used observation device was the same as in Example 12.

The obtained results were as follows:

(1) Owing to the very strong background of EB, the cells were neither confirmed nor observed, and the direct observation in the intact staining solution was difficult irrespective of the staining time.

(2) After the staining solution was replaced with the culture medium or a physiological saline, the observation was made, and it was apparent that cell nuclei were weakly stained in the case that the staining time was 1.5 hours or more.

EXAMPLE 13

(Preparation of long-term storage specimens of stained cells)

Cells were prepared fundamentally in the same manner as in Example 12. However, at the time of cultivation, a sterilized slide glass (for fluorescence observation) was buried in a culture dish, and the cells were propagated on the slide glass. The slide glass with the propagated cells was taken out from the culture dish, and the following operations were then aseptically carried out to stain the cells.

In the first place, the taken slide glass was immersed in a 4% aqueous formaldehyde solution for 30 minutes to achieve fixation. Afterward, the slide glass was passed through distilled water to simply wash it, and a suitable amount of a staining solution (1 μg/ml, a 0.5% ethanol solution, filter sterilization) prepared by the use of a stock solution of the present invention was then dropped thereon. Next, a cover glass for the fluorescence observation was put on the specimen, and the excessive staining solution was then removed. Afterward, the cover glass was fixed with a sealing resin to form a storage specimen.

Observation was carried out in the same manner as in Example 12, and as a result, cell nuclei were sharply stained and fluorescence images emitting clear fluorescence were observed, as in Example 12.

The specimens were stored at $-20°$ C., $4°$ C. and room temperature (each specimen was wrapped in aluminum foil to shut out light), and after 3 months, the fluorescence observation was made again. Since the specimens were sealed up in the aqueous solvent, the specimens other than the specimen stored at $-20°$ C. were in a good storage state, though the specimen stored at $-20°$ C. gave rise to the partial breakage of cell morphology. In addition, even after the storage, the fluorescence was sufficiently emitted, and a staining state was also good.

EXAMPLE 14

(Live cell staining of blood cells)

Blood cells obtained by a blood culture method ("All of Staining", Ishiyaku Publishers Inc., p. 366) were stained in the state of the unfixed live cells.

That is, 5 ml of a sampled peripheral blood was first placed in a sterilized Spitz tube, and the tube was uprightly allowed to stand, thereby separating the blood cells. Next, 0.5 ml of bovine serum and 0.1 ml of PHAM (made by Gibco Co., Ltd.) were added to 5 ml of a cell culture medium (RPMI 11640, made by Gibco Co., Ltd.), and the resulting mixture was put in a culture dish. Next, about 0.5 ml of the supernatant liquid of the separated blood, i.e., a plasma portion rich in leukocyte was added to the culture dish, and the cells were cultured for 3 days in a $CO_2$ incubator at $37°$ C.

A staining solution (concentration=200 μg/ml, an ethanol solution) prepared in the same manner as in Example 12 was added to a part of the suspension of the cultured cells, and the solution was then regulated so that the final concentration of a compound 1 might be 100 ng/ml and so that the final concentration of ethanol might be 0.5% to stain the blood cells.

For fluorescence observation, a culture medium containing the compound 1 was used as it was, and an inverted type refractive fluorescence microscope (trade name IMT-2, made by Olympus Optical Co., Ltd.) was used. As a result, cell nuclei were sharply stained, and fluorescence images emitting clear fluorescence were observed, as in Example 12. In addition, the fade phenomenon of the fluorescence was scarcely observed.

EXAMPLE 15

(Staining of cultured *Escherichia coli*)

As *Escherichia coli*, there was used a JM-109 strain which was usually utilized as a host for genetic recombination.

About 1% of agarose was added to an M-9 culture medium (pH=7.0) having the following composition, and the agarose was then melted and sterilized in an autoclave. Next, the solution was poured into a culture dish to form a plate.

Composition of the M-9 culture medium (in one liter):

| $Na_2HPO_4.7H_2O$ | 12.8 g |
| --- | --- |
| $KH_2PO_4$ | 3 g |
| NaCl | 0.5 g |
| $NH_4Cl$ | 1 g |
| $MgSO_4$ | 1 mM |
| glucose | 0.2% |
| $CaCl_2$ | 0.1 mM |
| balance | water |

The bacteria from the stock of the JM-109 strain (Takara Shuzo Co., Ltd.) were inoculated into this M-9 plate, and they were then incubated overnight in an incubator at $37°$ C. to propagate the bacteria, thereby obtaining colonies on the plate. Next, the bacteria were picked up from one of these colonies by a sterilized platinum loop, and then inoculated into 100 ml of a 2×YT culture medium having the following composition in a culture vessel.

Composition of the 2×YT culture medium (in one liter):

| bacto-trypton | 16 g |
| --- | --- |
| bacto-yeast extract | 10 g |
| NaCl | 5 g |
| balance | water |
| (pH = 7) | |

This culture medium was set to a thermostatic water bath with a shaker, and shake culture was carried out at $37°$ C. for about 10 hours. After completion of the culture, the cultured bacteria were harvested from the culture medium by centrifugal separation, and then resuspended again in physiological saline so that the concentration of the bacteria might be about $10^8$ bacteria/ml. Next, the obtained suspension was divided into two portions, and they were used in comparative tests using fixed bacteria and unfixed bacteria.

(1) Fluorescence staining of the fixed bacteria

A 4% formaldehyde solution (pH=7.0) was added to one portion of the suspension of the JM-109 strain obtained by the above-mentioned operations, the amount of the formaldehyde solution being equal to that of the suspension. After sufficiently stirred, the solution was allowed to stand for 30 minutes at room temperature to fixed the bacteria. The thus fixed bacteria were harvested by centrifugal separation, and then resuspended in physiological saline again. At the time of this suspension, the concentration of the bacteria was set in the range of from $10^7$ to $10^8$ bacteria/ml which was suitable for observation by a fluorescence microscope.

A staining solution was prepared by dissolving a compound 1 (Y=I) in ethanol so as to become a concentration of 200 μg/ml, and then sterilizing the solution and removing grains therefrom by the use of a filter.

This staining solution was added to the suspension 10 of the previously prepared fixed bacteria so that the final concentration of the compound 1 might be 0.2 µg/ml and so that the concentration of ethanol might be 0.5%, and the solution was then allowed to stand at room temperature for 10 minutes, thereby staining the bacteria. Afterward, fluorescence observation was done in this intact state where the fixed bacteria were suspension, i.e., without removing the compound 1 which was the dyestuff from the suspension solvent.

(2) Fluorescence staining of live bacteria (unfixed bacteria)

The same procedure as in the preceding paragraph (1) was carried out except that bacteria were not fixed with formaldehyde, to obtain the suspension of the stained live bacteria. Also in this case, fluorescence observation was done without removing the compound 1 which was the dyestuff from the suspension solvent.

Each of the bacteria suspensions obtained in the above-mentioned operations (1) and (2) was dropped on a slide glass, and a cover glass was then put thereon. Afterward, the excessive liquid was removed therefrom, and the glasses were sealed with a sealing resin. The fluorescence observation of the thus obtained specimens was carried out by the use of a refractive fluorescence microscope (trade name IMT-2, made by Olympus Optical Co., Ltd.). As a result, it was observed that the *Escherichia coli* which was procaryotic microorganisms was wholly stained. A difference of staining properties between the fixed bacteria and the unfixed bacteria was not observed, and in both the cases, fluorescence images emitting very light red fluorescence were observed. In addition, the fade phenomenon of the fluorescence was not observed.

After the observation, the staining solution of the unfixed bacteria was replaced with a culture medium, and cultivation was then carried out. In this case, the *Escherichia coli* normally propagated, and for the bacteria obtained by subcultures, it was possible to stain them again and to observe the fluorescence.

Also in the this case, there could not be observed a bad influence on the *Escherichia coli* by heat generation or the like which was attributed to the fluorescence observation for a long time in one visual field.

Comparative Example 3

[Live bacteria staining of *Escherichia coli* by ethidium bromide (EB)]

*Escherichia coli* which was a target to be stained was prepared in the same manner as in Example 15. A dyestuff (EB) is usually used in the state of an aqueous solution, but in this experiment, it was used in the state of an ethanol solution for the sake of coordination with Example 15. The concentration of the dyestuff solution was set to 200 µg/ml, as in Example 15. The dyestuff solution was passed through a filter having a pore size of 0.22 µm to sterilize the same and to remove particles therefrom.

*Escherichia coli* was stained in the same manner as in Example 15 by the use of this dyestuff (EB) solution. After the addition of the dyestuff solution, statical incubation was carried out for four different times, i.e., 5 minutes, 30 minutes, 1 hour and 1.5 hours, and a staining state was then observed. The obtained results were as follows:

The obtained results were as follows:

(1) When the observation was made in the intact state in which the dyestuff solution was added to the bacteria suspension, the liquid medium emitted light very strongly. That is, background was very strong, which disturbed the judgement of the staining state of the bacteria.

(2) The bacteria were separated from the liquid medium, washed, resuspended in a culture medium or physiological saline again, and then observed. As a result, it was apparent that the fixed bacteria were stained in a standing (staining) time of about 30 minutes, and the unfixed bacteria were stained in about one hour. However, the staining state of the unfixed bacteria was weaker than that of the fixed bacteria, and it was uneven.

EXAMPLE 16

(Preparation of long-term storage specimens of stained bacteria)

The same procedure as in Example 15 (1) was carried out except that sodium azide was added as an antiseptic so that the final concentration might be about 0.05%, to carry out the fluorescence staining of the fixed bacteria. Afterward, a staining state was observed, and as a result, it was apparent that the whole bacteria clearly emitted fluorescence, as in Example 15.

Many specimens were prepared by placing the samples in vessels and then sealing up them, and they were wrapped in aluminum foil to shut out light. Afterward, they were stored at $-20°$ C., $4°$ C. and room temperature. After a passage of 3 months, the fluorescence of the specimens was observed again. As a result, the specimen which was stored at $-20°$ C. gave rise to the partial breakage of the morphology of the bacteria by freezing, because the suspension medium of the bacteria was aqueous. However, the specimens stored at other storage temperatures were kept in a good storage state. In addition, fluorescence was also sufficiently emitted, and a staining state was also good.

EXAMPLE 17

(Staining of tissue section)

A sliced section of a mouse liver covered with paraffin on a slide glass prepared by a usual manner was stained with 2-methyl-4,6-bis-(4-N,N-dimethylaminophenyl) pyrylium iodide (a compound 1) in accordance with the following procedure. However, for observation by fluorescence, there were used the slide glass, various solvents and solutions which were free from the fluorescence.

In the first place, a suitable amount of 2-methyl-4,6-bis-(4-N,N-dimethylaminophenyl) pyrylium iodide (a compound 1) was dissolved in ethanol and then diluted with physiological saline, and the solution was next regulated so that the final concentration of the dyestuff might be 1 µg/ml and the concentration of ethanol might be 0.5%. This dyestuff solution was passed through a filter having a pore size of 0.22 µm to sterilize the same and to remove grains therefrom, thereby preparing a staining solution.

In order to increase the permeability of the aqueous staining solution, the paraffin was removed from the sliced section covered therewith of the specimen prior to its use. That is, the specimen was immersed in a xylol for 3 to 5 minutes to dissolve and remove the paraffin. After the removal of the paraffin was carried out again with a fresh xylol, the specimen was immersed in pure ethanol to remove xylol therefrom, and a fresh ethanol was used again to completely remove xylol. Afterward, the specimen was immersed in a 70% ethanol solution, and then washed with water to bring the paraffin removal operation to an end. Simultaneously, the environmental solvent of the specimen was replaced with an aqueous system.

Next, the slide glass specimen from which the paraffin had been removed was immersed in a suitable amount of the staining solution for 5 minutes to stain the same. After the staining, a thin cover glass for fluorescence observation was put on the section on the slide glass without washing the slide glass, and the glasses were sealed along their peripheries with a sealing agent. If the specimen is held in the sealed glasses together with the solution containing the dyestuff without removing the solution by washing, the staining state of the specimen can be maintained.

For the fluorescence observation, an inverted type refractive fluorescence microscope (trade name IMT-2, made by Olympus Optical Co., Ltd.) was used. A visual field was set by a transmitted phase contrast image, and the tissue specimen was then irradiated with excitation light. As a result, cell nuclei were clearly stained, and a stained image emitted bright fluorescence. During the observation, background was scarcely observed. This fact means that the washing/removal of the excessive dyestuff after the staining is unnecessary and it is less needful to take care of the dyestuff concentration in the staining operation. In addition, no fade phenomenon was present, and operations of the setting of the visual field, the taking of photographs and the like could be carried out with leeway without stopping the irradiation with the excitation light.

In this connection, at the time of sealing after the staining, sodium azide could be added as an antiseptic so that the final concentration might be about 0.05%, and in the thus sealed specimen, the fluorescence-stained image did not change and could be observed even after the storage of 3 months of more.

Comparative Example 4

[Staining of tissue section by ethidium bromide (EB)]

A dyestuff (EB) is usually used in the state of an aqueous solution, but in this experiment, it was used in the state of an ethanol solution for the sake of coordination with Example 17. The concentration of the dyestuff solution was such that the final concentration was 1 µg/ml, as in Example 17 (the final concentration of ethanol was 0.5%). The dyestuff solution was passed through a filter having a pore size of 0.22 µm to sterilize the same and to remove particles therefrom, thereby preparing a staining solution. Staining was also carried out in the same manner as in Example 17. After the addition of the staining solution, a staining state was observed at passage times of 5 minutes, 15 minutes, 1 hour and 1.5 hours. The same observation device as in Example 17 was used. The following results were obtained:

(1) In the case of EB, background was so strong that the tissue seemed to be wholly stained, and an image having no contrast was observed. It was difficult to observe cell nuclei alone.

(2) In the specimen which was stained for 1.5 hours, washed with distilled water, and then sealed, it was observed that the cell nuclei were weakly stained.

EXAMPLE 18

(Staining of a chromosome)

(1) Preparation of a chromosome specimen 5 ml of peripheral blood sampled from a normal adult human was first placed in a sterilized Spitz tube, and the tube was uprightly allowed to stand for 3 hours or more at room temperature, thereby separating the blood cells. Next, 0.5 ml of bovine serum and 0.5 ml of PHkM (made by Gibco Co., Ltd.) were added to 5 ml of a culture medium of RPMI 11640 (made by Gibco Co., Ltd.), and the resulting mixture was put in a culture dish. Next, about 0.5 ml of a plasma and leukocyte layer of an upper portion in the Spitz tube was added to the culture dish, and the cells were cultured for 3 days in a $CO_2$ incubator at 37° C. Next, colcemid was added to the culture medium so that the final concentration might be in the range of from 0.2 to 0.5 µg/ml, and the medium was allowed to stand for 2 to 3 hours. The cultivation was stopped, and cells were then harvested by centrifugation for 5 minutes at 1,000 rpm. Afterward, 3 ml of 0.075M of a KCl solution was added to the harvested cells, and the mixture was mildly stirred, and then allowed to stand for 7 minutes. Next, these cells were harvested by centrifugation, and a supernatant was then removed. Afterward, a calnoa fixing solution (pure methanol:glacial acetic acid=3:1) was added to the cells, and the mixture was then allowed to stand for 1 hour to fix them. The used fixing solution was replaced with a fresh fixing solution twice or thrice, and finally the cells were suspended in a small amount of the fixing solution. Next, to this solution, there added a staining solution in which an ethanol solution of 2-methyl-4,6-bis-(4-N,N-dimethylaminophenyl)thiopyrylium iodide (a compound 2) was regulated so that the final concentration of the compound 2 might be 500 ng/ml and so that the concentration of ethanol might be 1% or less. Here, the staining solution was beforehand passed through a filter having a pore size of 0.22 µm to sterilize the same and to remove particles therefrom. One or two drops of the mixture of the cell suspension solution and the staining solution was dropped on a cooled fluorescence-free slide through a Pasteur piper, and then dried up in air.

(2) Observation of a chromosome

The specimen on the slide obtained in the preceding (1) was sealed with a sealing resin, and it was put on a refractive fluorescence microscope (Nikon K. K.) connected to a high-sensitive CCD camera (made by Hamamatsu Photonics Co., Ltd.) to analyze a fluorescence pattern of a chromosome. As a result, it was apparent that the chromosome was clearly differentially stained and its pattern was different from a differential staining pattern by quinacrine. By this differential staining pattern, the chromosome could be classified.

EXAMPLE 19

In the first place, cells were cultured in the same manner as in Example 18, and they were then hervested by centrifugation. Next, to the hervested cells, there was added a 0.075M KCl solution (3 ml) to which 2-methyl-4,6-bis-(4-N,N-dimethylaminophenyl)pyrylium iodide (a compound 1) was added so that the final concentration might be 500 ng/ml and the concentration of ethanol might be 1% or less. In this case, the harvested cells were not subjected to a fixation treatment with a calnoa fixing solution. Afterward, a chromosome was diffused in accordance with a vapor drying method ("All of Staining", Ishiyaku Publishers Inc., p. 366), and excessive water drops were wiped off without particular drying. Next, a cover glass was put on the chromosome, and its periphery was then sealed up with a sealing resin. The specimen was observed in the same manner as in Example 18. As a result, it was apparent that the chromosome was clearly differentially stained even without any fixation operation, and about the same results as in Example 18 were obtained. After that step, this fluorescence was scarcely faded. After one month, this specimen was observed again, and at this time, about the same fluorescence as at the time of the manufacture could be obtained again.

EXAMPLE 20

(Detection by in situ hybridization)

2-(4-carboxystyryl-4,6-bis-(4-N,N-dimethylaminophenyl)pyrylium iodide [a compound 48 (X=O and Y=I)] was synthesized from carboxybenzaldehyde and a compound 1 (Y=I).

Next, 170 mg of the thus synthesized compound 48 was dissolved in 5 ml of dry DMF, and 50 µl of dry pyridine and 128 mg of DSC (disuccimizyl carbonate) were added thereto, followed by stirring in a dark place at room temperature for 20 hours. Afterward, 150 ml of diethyl ether was added to the reaction mixture, and the resulting precipitate was harvested, washed with diethyl ether, and then dried. The thus obtained active ester was used in a reaction with a nucleic acid.

A 30-mer oligonucleotide having an amino linker at its 5' terminal and having the following base sequence which was complementary to a part of the base sequence of the mRNA of an immunoglobulin K chain in a mouse was synthesized by the use of a DNA synthesizer 381A made by ABI Co., Ltd.:

SEQ ID NO.2λ5'CTCACAGGTATAGCTGTTATGTCGTTCATA3'

The cleaving from a CPG support, deprotection, and purification by a high-performance liquid chromatography (HPLC) were carried out in usual manners.

Next, 200 µg of the above-mentioned oligonucleotide, 100 µl of 1M sodium sulfate buffer solution and 500 µl of water were mixed and dissolved, and 2 mg of the above-mentioned active ester beforehand dissolved in 400 µl of DMF was slowly added thereto with stirring. Reaction was carried out at 40° C. for 24 hours, and the reaction solution was then crudely purified through a gel filter column NAP-50 made by Farmacia Co., Ltd. and then further purified by HPLC to obtain about 150 µg of a following DNA probe labeled with the compound of the present invention:

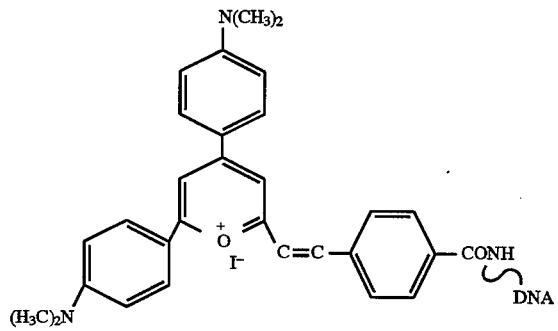

(2) In situ hybridization

P3×63 Ag8U.1 of myeloma cells of a mouse was suspended in a DMEM culture medium, and the suspension was spread on a dish so as to be $2.5 \times 10^5$ cells/ml. After cultivation at 37° C. for 36 hours, the DMEM culture medium was replaced with another DMEM culture medium containing the probe prepared in the above-mentioned step (1) at a concentration of 10 nM, and cultivation was further continued for 1 hour. Next, the operation of replacing the used culture medium with a culture medium containing no probe and then culturing the cells for 30 minutes was repeated twice, and observation was then made by the use of a fluorescence microscope. In this fluorescence microscope observation, filters suitable for the absorption wavelength and fluorescence wavelength of the probe were used, and detection was done by the use of a super-high-sensitive CCD camera. As a result, fluorescence was observed on the cells.

On the other hand, a probe for comparison was synthesized from a nucleotide having a base sequence in which homology was lower than in a nucleic acid in the above-mentioned cell, and similar observation was then made. As a result, any fluorescence was not observed.

EXAMPLE 21

(Detection of a PCR amplified product)

PCR was carried out, using 16S ribosomal RNA of E. coli as a target, and its amplified product was detected by the use of a compound 1.

In the first place, the whole DNA of an E. coli JM 109 strain was prepared as follows. 2 ml of the bacterial suspension had been cultured overnight in a 2×YT culture medium. And the bacteria was harvested by centrifugal separation, and then suspended in 0.5 ml of a 0.1M sodium phosphate buffer solution (pH=8.0). Next, 0.05 ml of a 10% SDS solution was added to this suspension, and after sufficient mixing, the mixture was held at 70° C. for 1 hour. This suspension was mixed with a vortex mixer to completely lyse the bacteria. Afterward, phenol/chloroform was added to this lysed solution, the amount of the phenol/chloroform being equal to that of the lysed solution, and mixing and centrifugal separation were then done. The resulting upper layer was taken out, and ethanol was added thereto, the amount of ethanol being twice as much as that of the upper layer, so that DNA was harvested in the form of a precipitate. This DNA was dissolved in 100 µl of a TE buffer solution (pH=8) to form a template DNA of PCR.

The following two primers were used in PCR:

Primer 1: SEQ ID NO. 3 5'AGAGTTTGATCCTGGCT-CAG3'

Primer 2: SEQ ID NO. 4 5'AACCCAACATCTCACGA-CAC3'

These primers were synthesized by the use of a DNA synthesizer 381A made by ABI Co., Ltd. Reagents and techniques necessary for the synthesis depend upon the protocol of the ABI Co., Ltd.

Reaction conditions of PCR were as follows:

Composition of a reaction solution (volume 30 µl)

| 10× buffer | 3 µl |
| --- | --- |
| dNTPs | 1 µl |
| Primer 1 | 10 pmoles |
| Primer 2 | 10 pmoles |
| Taq DNA polymerase | 0.5 unit |
| Template DNA | 100 pg, 10 pg, 1 pg, 100 fg and 10 fg |

A sterilized water was added to the reaction solution to bring the total volume to 30 µl.

The Taq DNA polymerase employed here had been manufactured by Takara Shuzo Co., Ltd. In addition, 10×buffer and dNTPs used here was the same that had been attaching to enzymes.

A reaction cycle was as follows:

Preincubation at 92° C. for 5 minutes 30 cycles of 92° C.-45 sec, 60° C.-60 sec, and 72° C.-90 sec Finally, incubation at 72° C. for 5 minutes.

Here, as a PCR device, there was used model PTC-100-96 made by MJ Research, Inc., and as a reaction vessel, there was used a 96-well microtiter plate (Falcon Assay Plate 3911 (U bottom) made by Becton-Dickinson Co., Ltd.).

PCR was carried out under the above-mentioned conditions and the amplified product was detected.

The detection was carried out as follows: 1 µl of a 5 µg/ml compound (an acetonitrile solution) was added to each well in which the reaction was over, and they were sufficiently mixed by pipetting and then allowed to stand at room temperature for 5 minutes. The thus treated sample was put on a transilluminator capable of irradiating the sample with light through the plate, and presence/absence of the amplified product was inspected by presence/absence of fluorescence. Furthermore, 10 µl of the reaction solution in the well was sampled, and agarose gel electrophoresis was also carried out. The results are shown in Table 3.

Comparative Example 5

[Detection of a PCR amplified product by use of EB]

PCR was carried out, using 16S ribosomal RNA of *E. coli* as a target, and its amplified product was detected by the use of EB.

A template DNA prepared in Example 21 was utilized. Furthermore, a primer, a reaction solution composition, a reaction cycle and the amount of the template DNA were all the same as in Example 21, and a compound to be detected was only changed.

The detection was carried out as follows: 1 µl of 5 µg/ml EB was added to each well in which reaction had been over, and they were sufficiently mixed by pipetting and then allowed to stand at room temperature for 5 minutes. The thus treated sample with a plate was put on a transilluminator (Model TM-10, made by UVP, Inc.), and presence/absence of the amplified product was inspected by presence/absence of fluorescence. Furthermore, 10 µl of the reaction solution in the well was sampled, and agarose gel electrophoresis was also carried out. The results are shown in Table 4.

TABLE 3

| Amount of DNA | 100 pg | 10 pg | 1 pg | 100 fg | 10 fg |
|---|---|---|---|---|---|
| Fluorescence | O | O | O | O | O |
| Electrophoresis | O | O | O | O | O |

O: The PCR amplified product was detected.
X: The PCR amplified product was not detected.

TABLE 4

| Amount of DNA | 100 pg | 10 pg | 1 pg | 100 fg | 10 fg |
|---|---|---|---|---|---|
| Fluorescence | O | O | O | X | X |
| Electrophoresis | O | O | O | X | X |

O: The PCR amplified product was detected.
X: The PCR amplified product was not detected.

As shown in Tables 3 and 4, the sensitivity of the detection of the PCR amplified product was increased two orders of magnitude by using the compound 1 of the present invention, over that using EB, the conventional intercalater.

Reference will be made to the effects of the present invention.

Most of the compounds of the formula [I] which is an effective component of a stain of the present invention have an excitation wavelength of 550 nm or more on a long wavelength side, and for example, the excitation can be achieved by a xenon lamp or a tungsten lamp, so that the use of harmful ultraviolet rays can be avoided. Furthermore, since the excitation light on the long wavelength side is utilized, the rise of background in the detection of a sample derived from an organism can be inhibited, whereby a high-sensitive analysis is possible. For example, the sample derived from the organism is often contaminated with substances which are excited by ultraviolet rays to emit fluorescence. Thus, if the ultraviolet rays are used as the excitation light, it is necessary that the sample is purified to some extent. On the contrary, if the stain of the present invention is used, the emission of the fluorescence from such substances can be inhibited, and so the high purification of the sample is not required any more. For example, the sample such as a crude extract can be directly utilized, and the detection with high sensitivity is possible.

Moreover, a compound having absorption in a near infrared region can be selected and utilized as the compound of the formula [I], which permits the utilization of a small-sized inexpensive semiconductor laser as a light source for the excitation, so that a measuring cost can be decreased.

Furthermore, the stokes shift of the compound of the formula [I] is about 100 nm, and the excited light can be completely separated from the fluorescence light. Thus, the high-sensitive detection is possible in a high S/N ratio, which is particularly effective for the automation of the measurement.

In addition, the detection of a nucleic acid and a nucleic acid fragment in a gel separated by electrophoresis can be sufficiently carried out by a light source such as the tungsten lamp, and thus the detection of DNA can be achieved with a good sensitivity without bathing in the ultraviolet rays which are harmful to humans. At this time, the detection sensitivity is 10 times or more higher than in the case of ethidium bromide, the S/N ratio is good, and the enhancement of fluorescence intensity which depends upon the concentration of DNA can be obtained in a wide region, which permits the detection in a wide concentration range.

In a hybridization reaction in a solution system, the stain of the present invention can be used to detect a hybrid of a probe and a target nucleic acid, and in this case, the compound of the formula [I] functions as an intercalater for the base pair of the nucleic acid. Thus, the compound intercalates in the double-strand nucleic acid, so that the fluorescence intensity increases, for example, in the case of the compound 1, at most 400 times as much as in a free state by interaction with the double-strand nucleic acid. Hence, the detection of the hybrid can be achieved without B/F separation, and so the detection of an amplified product of PCR can be very simply achieved. In addition, the hybrid can be stabilized, and so a stable analysis is possible.

The compound of the formula [I] of the present invention can be used as a dyestuff for staining a biological sample, whereby there can be provided a fluorescence staining method suitable for many biological samples in which fixation and a washing operation can be omitted or remarkably simplified in contrast to conventional methods. In addition, in the present invention, the fixing operation of the biological samples can be omitted, and so fluorescence observation is possible in a live state or in a natural state and the fluorescence observation with time in the cultivation of one sample is also possible. Moreover, a long-term storage specimen by the fluorescence staining can also be prepared. For the sake of the differential staining of a chromosome, there can be provided a differential staining method using a fluorescence dyestuff which is different from a conventional dyestuff in a differential pattern.

What is claimed is:

1. A process for detecting a double-stranded nucleic acid, comprising the steps of:
  providing a biological sample which may contain double-stranded nucleic acid;
  providing a pyrylium compound represented by the following formula I:

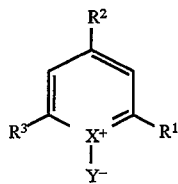

(I)

wherein

X is O, S, Se or Te, two of $R^1$, $R^2$ and $R^3$ are independently substituted or unsubstituted aryl groups; the other is a hydrogen atom, halogen atom, sulfonate group, amino group, styryl group, nitro group, hydroxyl group, carboxyl group, cyano group, substituted or unsubstituted lower alkyl group, or substituted or unsubstituted cycloalkyl group, -A or -L-A, L is $-L^1-$, $-L^2-L^3-$ or $-L^6-L^5-L^6-$, and each of $L^1$ to $L^6$ is independently —(CH=CH)—, a divalent group derived from the substituted or unsubstituted aryl group, a substituted or unsubstituted lower alkylene group, or —CH=$R^6$—, wherein $R^6$ is a ring structure having an oxo group, A is a substituted or unsubstituted aryl group or —CH=$R^5$—, wherein $R^5$ is a substituted or unsubstituted heterocyclic ring, a substituted or unsubstituted cycloalkyl group, or a substituted or unsubstituted aromatic ring, or substituted or unsubstituted lower aralkyl group, and $Y^-$ is an anion;

mixing the pyrylium compound with the biological sample to intercalate the pyrylium compound into the double-stranded nucleic acid;

irradiating the double-stranded nucleic acid in which the pyrylium compound is trapped as an intercalator with light including a frequency at which the trapped pyrylium compound exhibits significant absorptivity of sufficient magnitude to excite the trapped pyrylium compound; and measuring fluorescent light emitted from the trapped pyrylium compound which is excited to detect the presence of the double-stranded nucleic acid.

2. The process according to claim 1, wherein the pyrylium compound is represented by the following formula VII:

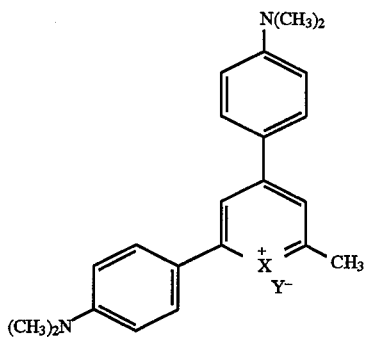

wherein X is O or S and $Y^-$ is an anion.

3. The process according to claim 1, wherein the pyrylium compound is represented by the following formula VIII:

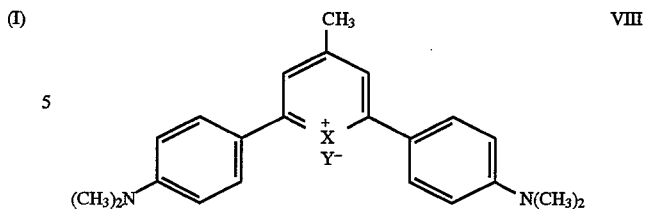

wherein X is O or S and $Y^-$ is an anion.

4. The process according to claim 1, wherein the sample is a double-stranded nucleic acid or double-stranded nucleic acid fragment separated by agarose gel electrophoresis or polyacrylamide gel electrophoresis.

5. The process according to claim 1, wherein the sample comprises a double-stranded hybrid in which a probe is complementary bound to a target single-stranded nucleic acid.

6. The process according to claim 1, wherein the sample is a double-stranded nucleic acid amplified by a PCR reaction.

7. A process for detecting a double-stranded nucleic acid in a biological sample, comprising the steps of:

providing a biological stain comprising a pyrylium compound represented by the following formula I;

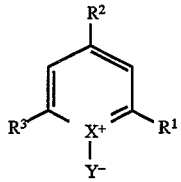

(I)

wherein

X is O, S, Se or Te, two of $R^1$, $R^2$ and $R^3$ are independently substituted or unsubstituted aryl groups; the other is a hydrogen atom, halogen atom, sulfonate group, amino group, styryl group, nitro group, hydroxyl group, carboxyl group, cyano group, substituted or unsubstituted lower alkyl group, unsubstituted aryl group, substituted or unsubstituted lower or substituted or unsubstituted cycloalkyl group, -A or -L-A, L is $-L^1-$, $-L^2-L^3-$ or $-L^4-L^5-L^6-$, and each of $L^1$ to $L^6$ is independently —(CH=CH)—, a divalent group derived form the substituted or unsubstituted aryl group, a substituted or unsubstituted lower alkylene group or —CH=$R^4$—, wherein $R^4$ is a ring structure having an oxo group, A is a substituted or unsubstituted aryl group or —CH=$R^4$—, wherein $R^5$ is a substituted or unsubstituted heterocyclic ring, a substituted or unsubstituted cycloalkyl group, or a substituted or unsubstituted aromatic ring, $Y^{-0}$ is an anion;

providing a biological sample which may contain a double-stranded nucleic acid;

bringing the biological sample into contact with the biological stain to intercalate the pyrylium compound into the double-stranded nucleic acid;

irradiating the double-stranded nucleic acid in which the pyrylium compound is trapped as an intercalator with light including a frequency at which the trapped pyrylium dye exhibits significant absorptivity of sufficient magnitude to excite the trapped pyrylium compound; and measuring a fluorescent light emitted from the trapped pyrylium compound is excited to detect the existence of the double-stranded nucleic acid.

8. The process according to claim 7, wherein the biological sample is a microorganism, a biological tissue, a biological tissue section, a human cell, an animal cell or a chromosome.

9. The process according to claim 7, wherein the stain further comprises physiological saline.

10. The process according to claim 7, wherein the biological sample is unfixed.

11. The process according to claim 10, wherein the unfixed biological sample is live microorganisms, live human cells or live animal cells.

12. The process according to claim 7, wherein the stain further comprises a culture medium for the biological sample.

13. The process according to claim 7, wherein the pyrylium compound is represented by the following formula VII:

[Structure VII: pyrylium compound with N(CH$_3$)$_2$ groups, X$^+$, Y$^-$, CH$_3$]

wherein X is O or S and Y$^-$ is an anion.

14. The process according to claim 7, wherein the pyrylium compound is represented by the following formula VIII:

[Structure VIII: pyrylium compound with CH$_3$, two (CH$_3$)$_2$N groups, X$^+$, Y$^-$]

wherein X is O or S and Y$^-$ is an anion.

15. A process for detecting a target single-stranded nucleic acid comprising the steps of:

providing a probe comprising a nucleic acid having a base sequence being complementary to a base sequence of a target nucleic acid and a pyrylium compound represented by the following formula I bound to the nucleic acid;

[Structure I: with R$^1$, R$^2$, R$^3$, X$^+$, Y$^-$]

wherein

X is O, S, Se or Te, two of R$^1$, R$^2$ and R$^3$ are independently substituted or unsubstituted aryl groups: the other is a hydrogen atom, halogen atom, sulfonate group, amino group, styryl group, nitro group, hydroxyl group, carboxyl group, cyano group, substituted or unsubstituted lower alkyl group, or substituted or unsubstituted cycloalkyl group, —A or —L—A, L is —L$^1$—, —L$^2$—L$^3$— or —L$^4$—L$^5$—L$^6$—, and each of L$^1$ to L$^6$ is independently —(CH=CH)—, a divalent group derived from the substituted or unsubstituted aryl group, a substituted or unsubstituted lower alkylene group, or —CH=R$^6$—, wherein R$^4$ is a ring structure having an oxo group, A is a substituted or unsubstituted aryl group or —Ch=R$^5$—, wherein R$^5$ is a substituted or unsubstituted heterocyclic ring, a substituted or unsubstituted cycloalkyl group, or a substituted or unsubstituted aromatic ring, and Y$^-$ is an anion;

providing a sample which may contain a single-stranded nucleic acid as the target;

mixing the probe and the sample to bind the probe to the target complementary to form a double-stranded hybrid which traps the pyrylium compound as an intercalator;

irradiating the mixture of the sample and the probe, which may contain the double-stranded hybrid trapping the pyrylium compound as an intercalator with light including a frequency at which the trapped pyrylium compound exhibits significant absorptivity of sufficient magnitude to excite the trapped pyrylium compound; and measuring fluorescent light emitted from the trapped pyrylium compound which is excited to detect the presence of the hybrid.

16. The process according to claim 15, wherein the compound is represented by the following formula VII;

[Structure VII: pyrylium compound with N(CH$_3$)$_2$ groups, X$^+$, Y$^-$, CH$_3$]

wherein X is O or S and Y$^-$ is an anion.

17. The process according to claim 15, wherein the compound is represented by the following formula VIII

[Structure VIII: pyrylium compound with CH$_3$, two (CH$_3$)$_2$N groups, X$^+$, Y$^-$]

wherein X is O or X and Y$^-$ is an anion.

18. A process for detecting a target single-stranded nucleic acid comprising the steps of:

providing a probe comprising a nucleic acid having a base sequence being complementary to a base sequence of a target nucleic acid and a pyrylium compound represented by the following formula I bound to the nucleic acid;

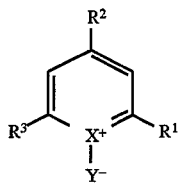
(I)

wherein

X is O, S, Se or Te, two of $R^1$, $R^2$ and $R^3$ are independently substituted or unsubstituted aryl groups; the other is a hydrogen atom, halogen atom, sulfonate group, amino group, styryl group, nitro group, hydroxyl group, carboxyl group, cyano group, substituted or unsubstituted lower alkyl group, or substituted or unsubstituted cycloalkyl group, -A or -L-A, L is -$L^1$-, -$L^2$-$L^3$- or -$L^4$-$L^5$-$L^6$-, and each of $L^1$ to $L^6$ is independently —(CH=CH)—, a divalent group derived from the substituted or unsubstituted aryl group, a substituted or unsubstituted lower alkylene group, or —CH=$R^4$—, wherein $R^4$ is a ring structure having an oxo group, A is a substituted or unsubstituted aryl group or —CH=$R^5$—, wherein $R^5$ is a substituted or unsubstituted heterocyclic ring, a substituted or unsubstituted cycloalkyl group, or a substituted or unsubstituted aromatic ring, and $Y^-$ is an anion;

providing a live biological sample which may contain a single-stranded nucleic acid as the target;

bringing the probe into contact with the sample to bind the robe to the target complementary to form a double-stranded hybrid which traps the pyrylium compound as an intercalator;

irradiating the mixture of the sample and the probe, which may contain the double-stranded hybrid trapping the pyrylium compound as an intercalator with light including a frequency at which the trapped pyrylium compound exhibits significant absorptivity of sufficient magnitude to excite the trapped pyrylium compound; and measuring fluorescent light emitted from the trapped pyrylium compound which is excited to detect the presence of the hybrid.

19. The process according to claim 18, wherein the live biological sample is selected from the group consisting of organisms, live cells and live bacteria.

20. The process according to claim 18, wherein the pyrylium compound is represented by the following formula VII:

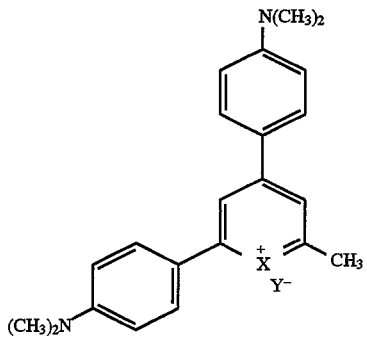
VII wherein X is O or S and $Y^-$ is an anion.

21. The process according to claim 18, wherein the pyrylium compound is represented by the following formula VIII:

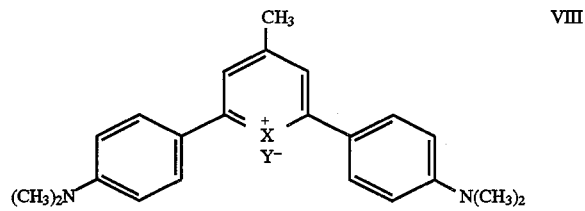
VIII wherein X is O or S and $Y^-$ is an anion.

22. A process for detecting a double-stranded nucleic acid, comprising the steps of:

providing a biological sample which may contain double-stranded nucleic acid;

providing a pyrylium compound represented by the following formula I:

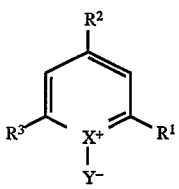
(I)

wherein

X is O, S, Se or Te, two of $R^1$, $R^2$ and $R^3$ are independently substituted or unsubstituted aryl groups; the other is a hydrogen atom, halogen atom, sulfonate group, amino group, styryl group, nitro group, hydroxyl group, carboxyl group, cyano group, substituted or unsubstituted lower alkyl group, or substituted or unsubstituted cycloalkyl group, -A or -L-A, L is -$L^1$-, -$L^2$-$L^3$- or -$L^4$-$L^5$-$L^6$-, and each of $L^1$ to $L^6$ is independently —(CH=CH)—, a divalent group derived from the substituted or unsubstituted aryl group, a substituted or unsubstituted lower alkylene group, or —CH=$R^4$—, wherein $R^4$ is a ring structure having an oxo group, A is a substituted or unsubstituted aryl group or —CH=$R^5$—, wherein $R^5$ is a substituted or unsubstituted heterocyclic ring, a substituted or unsubstituted cycloalkyl group, or a substituted or unsubstituted aromatic ring, and $Y^-$ is a anion;

mixing the pyrylium compound with the biological sample to intercalate the pyrylium compound into the double-stranded nucleic acid;

irradiating the double-stranded nucleic acid in which the pyrylium compound is trapped as an intercalator with light to excite the trapped pyrylium compound; and measuring fluorescent light emitted from the trapped pyrylium compound which is excited to detect the existence of the double-stranded nucleic acid.

23. The process for detecting a double-stranded nucleic acid, comprising the steps of:

providing a biological sample which may contain double-stranded nucleic acid;

providing a pyrylium compound represented by the following formula I:

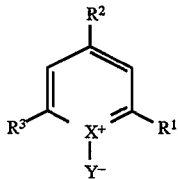

wherein

X is O, S, Se or Te, two of $R^1$, $R^2$ and $R^3$ are independently substituted or unsubstituted aryl groups; the other is a hydrogen atom, halogen atom, sulfonate group, amino group, styryl group, nitro group, hydroxyl group, carboxyl group, cyano group, substituted or unsubstituted lower alkyl group, or substituted or unsubstituted cycloalkyl group, -A or -L-A, L is $-L^1-$, $-L^2-L^3-$ or $-L^4-L^5-L^6-$, and each of $L^1$ to $L^6$ is independently $-(CH=CH)-$, a divalent group derived from the substituted or unsubstituted aryl group, a substituted or unsubstituted lower alkylene group, or $-CH=R^4-$, wherein $R^4$ is a ring structure having an oxo group, A is a substituted or unsubstituted aryl group or $-CH=R^5-$, wherein $R^5$ is a substituted or unsubstituted heterocyclic ring, a substituted or unsubstituted cycloalkyl group, or a substituted or unsubstituted aromatic ring, and $Y^-$ is an anion;

mixing the pyrylium compound with the biological sample to intercalate the pyrylium compound into the double-stranded nucleic acid;

irradiating the double-stranded nucleic acid in which the pyrylium compound is trapped as an intercalator with light to excite the trapped pyrylium compound; and measuring fluorescent light having a longer wavelength than that of the light for exciting the trapped pyrylium compound which is excited to detect the existence of the double-stranded nucleic acid.

24. The process for detecting a double-stranded nucleic acid, comprising the steps of:

intercalating a pyrylium compound represented by the following formula I into a double-strand nucleic acid in a biological sample:

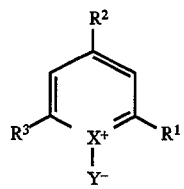

wherein

X is O, S, Se or Te, two of $R^1$, $R^2$ and $R^3$ are independently substituted or unsubstituted aryl groups; the other is a hydrogen atom, halogen atom, sulfonate group, amino group, styryl group, nitro group, hydroxyl group, carboxyl group, cyano group, substituted or unsubstituted lower alkyl group, or substituted or unsubstituted cyloalkyl group, -A or -L-A, L is $-L^1-$, $-L^2-L^3-$ or $-L^4-L^5-L^6-$, and each of $L^1$ to $L^6$ is independently $-(CH=CH)-$, a divalent group derived from the substituted or unsubstituted aryl group, a substituted or unsubstituted lower alkylene group, or $-CH=R^4-$, wherein $R^4$ is a ring structure having an oxo group, A is a substituted or unsubstituted aryl group or $-CH=R^5-$, wherein $R^5$ is a substituted or unsubstituted heterocyclic ring, a substituted or unsubstituted cycloalkyl group, or a substituted or unsubstituted aromatic ring, $Y^-$ is an anion;

irradiating the intercalated pyrylium compound with light including a frequency at which the intercalated pyrylium compound exhibits maximum absorption to excite the intercalated pyrylium compound; and measuring fluorescence having longer wavelength than that of the light for exciting the intercalated pyrylium compound to detect the quantity of the double-stranded nucleic acid.

25. The process for detecting a double-stranded nucleic acid according to any one of claims 22, 23 and 24, wherein the pyrylium compound is represented by the following formula VII:

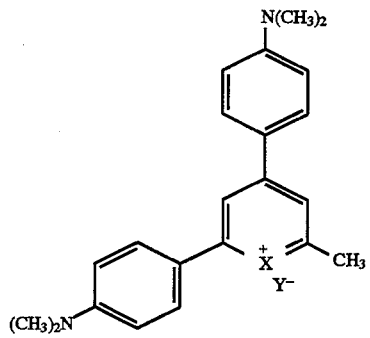

wherein X is O or S, and $Y^-$ is an anion.

26. The process according to any one of claims 22, 23 or 24, wherein the pyrylium compound is represented by the following formula VIII:

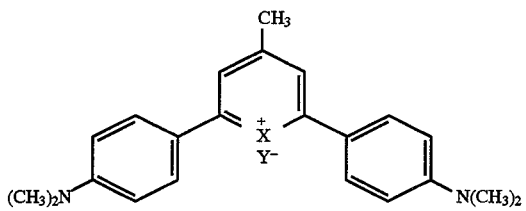

VIII wherein X is O or S and Y⁻ is an anion.

27. The process according to any one of claims 22, 23 or 24, wherein the biological sample is a double-stranded nucleic acid or double-stranded nucleic acid fragment separated by agarose gel electrophoresis or polyacrylamide gel electrophoresis.

28. The process according to any one of claims 22, 23 or 24, wherein the biological sample comprises a double-stranded hybrid formed by a target nucleic acid and a probe having a base sequence which is complementary to that of the target nucleic acid.

29. The process according to any one of claims 22, 23 or 24, wherein the biological sample is a cell or an organism.

30. The process according to any one of claims 22, 23 or 24, wherein the biological sample is unfixed.

31. The process according to any one of claims 22, 23 or 24, wherein the unfixed biological sample is live cell or live tissue.

32. A process for detecting a target single-stranded nucleic acid comprising the steps of:

providing a probe comprising a nucleic acid having a base sequence being complementary to a base sequence of a target nucleic acid and a pyrylium compound represented by the following formula I bound to the nucleic acid;

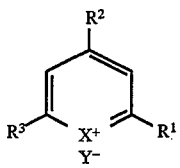

I wherein X is O, S, Se or Te, two of $R^1$, $R^2$ and $R^3$, are independently substituted or unsubstituted aryl groups; the other is a hydrogen atom, halogen atom, sulfonate group, amino group, styryl group, nitro group, hydroxyl group, carboxyl group, cyano group, substituted or unsubstituted lower alkyl group, or substituted or unsubstituted cycloalkyl group, -A or -L-A, L is -$L^1$-, -$L^2$-$L^3$- or -$L^4$-$L^5$-$L^6$-, and each of $L^1$ to $L^6$ is independently -(CH=CH)-, a divalent group derived from the substituted or unsubstituted aryl group, a substituted or unsubstituted lower alkylene group, or —CH=$R^4$—, wherein $R^4$ is a ring structure having an oxo group, A is a substituted or unsubstituted aryl group or —CH=$R^5$—, wherein $R^5$ is a substituted or unsubstituted heterocyclic ring, a substituted or unsubstituted cycloalkyl group, a substituted or unsubstituted aromatic ring, and Y⁻ is an anion;

providing a sample which may contain a single-stranded nucleic acid as the target;

mixing the probe and a sample which may contain a single-stranded target nucleic acid to bind the probe to the target complementary to form a double-stranded hybrid which traps the pyrylium compound as an intercalator;

irradiating a mixture of the sample and the probe, which may contain the double-stranded hybrid trapping the pyrylium compound as an intercalator with light to excite the trapped pyrylium compound; and measuring fluorescent light emitted from the trapped pyrylium compound which is excited to detect the presence of the hybrid.

* * * * *

UNITED STATES PATENT AND TRADEMARK OFFICE
CERTIFICATE OF CORRECTION

PATENT NO.  :  5,624,798

DATED       :  April 29, 1997

INVENTOR(S) :  NOBUKO YAMAMOTO ET AL.

It is certified that error appears in the above-identified patent and that said Letters Patent is hereby corrected as shown below:

On the title page, item
[56] REFERENCES CITED

OTHER PUBLICATIONS
      After "C. Picard et al.": "an" should read --and--;
      After "R. Cardullo et al.": "8790-94" should read
        --85,8790-94--; and
      After "C. Murphy et al.": Nov.n" should read --Nov.--.

[56] REFERENCES CITED

OTHER PUBLICATIONS, Page 2
      After "Bringmann et al.": "On" should read --Only--.

COLUMN 1

Line 31, "Gets" should read --gets--.

COLUMN 2

Line 42, "an" should read --a--.

COLUMN 4

Line 46, "the staining" should read --staining--.
   Line 48, "an" should be deleted.

COLUMN 5

Line 30, "a desired" should read --desired--.

UNITED STATES PATENT AND TRADEMARK OFFICE
CERTIFICATE OF CORRECTION

PATENT NO. : 5,624,798

DATED : April 29, 1997

INVENTOR(S) : NOBUKO YAMAMOTO ET AL.

It is certified that error appears in the above-identified patent and that said Letters Patent is hereby corrected as shown below:

COLUMN 10

Line 34, "diethylamono" should read --diethylamino--.

COLUMN 12

Line 30, "more increases" should read --increases more--.
    Line 33, "feature" should read --the feature--.

COLUMN 14

Line 27, "an" should read --a--.
    Line 28, "Generating" should read --generating--.

COLUMN 15

Line 10, "miss-matched" should read --mismatched--.
    Line 15, "in site" should read --in situ--.

COLUMN 17

Line 49, "up it," should read --it up,--.
    Line 59, "up it." should read --it up.--.

COLUMN 18

Line 6, "the a" should read --then a--.
    Line 10, "in" should read --with--.
    Line 27, "Green" should read --green--.

UNITED STATES PATENT AND TRADEMARK OFFICE
CERTIFICATE OF CORRECTION

PATENT NO. : 5,624,798

DATED : April 29, 1997

INVENTOR(S): NOBUKO YAMAMOTO ET AL.

It is certified that error appears in the above-identified patent and that said Letters Patent is hereby corrected as shown below:

COLUMN 19

Line 4, "recrystallication" should read --recrystallization--.
Line 18, "Vcm$^{-1}$" should read --Vcm$^{-1}$:--.

COLUMN 20

Line 2, "hydoriodic" should read --hydroiodic--.

COLUMN 29

Line 15, "(1964)";" should read --(1964);--.
Line 67, "route;" should read --route:--.

COLUMN 30

Line 43, "compound 5," should read --compounds 5,--.

COLUMN 37

Comp. 45, "1(X=)" should read --1(X=0)--.

COLUMN 38

Line 46, Insert: --47--.
Line 66, Insert: --48--.

UNITED STATES PATENT AND TRADEMARK OFFICE
CERTIFICATE OF CORRECTION

PATENT NO. : 5,624,798

DATED : April 29, 1997

INVENTOR(S) : NOBUKO YAMAMOTO ET AL.

Page 4 of 9

It is certified that error appears in the above-identified patent and that said Letters Patent is hereby corrected as shown below:

COLUMN 39

Line 13, Insert: --49--.
    Line 27, Insert: --50--.
    Line 42, Insert: --51--.

COLUMN 41

Line 2, "$N(CH_3)_2$" should be deleted.

COLUMN 42

Line 28, "ƒ/Hind III" should read --λ/Hind III--.
    Line 36, "Gel" should read --gel--.
    Line 39, "Gel" should read --gel--.
    Line 48, "Good." should read --good.--

COLUMN 43

Line 30, "5'GTTGTAAAACGACGGCCAGT3'SEQ IS NO:1" should read --SEQ ID NO. 1 5'GTTGTAAAACGACGGCCAGT3'--.

COLUMN 48

Line 4, "12.In" should read --12. In--.

UNITED STATES PATENT AND TRADEMARK OFFICE
CERTIFICATE OF CORRECTION

PATENT NO. : 5,624,798

DATED : April 29, 1997

INVENTOR(S) : NOBUKO YAMAMOTO ET AL.

Page 5 of 9

It is certified that error appears in the above-identified patent and that said Letters Patent is hereby corrected as shown below:

COLUMN 49

Line 1, "10" should be deleted.
Line 39, "the this" should read --this--.

COLUMN 50

Line 21, "up them," should read --them up,--.

COLUMN 51

Line 62, "PHkM" should read --PHAM--.

COLUMN 52

Line 25, "piper," should read --pipette,--.
Line 40, "hervested" should read --harvested--.
Line 41, "hervested" should read --harvested--.

COLUMN 53

Line 7, "hervested," should read --harvested,--.
Line 13, "K chain" should read --$\kappa$ chain--.
Line 16, "NO.2$\lambda$5'" should read --No.2 5'--.

COLUMN 54

Line 21, "hervested" should read --harvested--.

UNITED STATES PATENT AND TRADEMARK OFFICE
CERTIFICATE OF CORRECTION

PATENT NO. : 5,624,798

DATED : April 29, 1997

INVENTOR(S): NOBUKO YAMAMOTO ET AL.

It is certified that error appears in the above-identified patent and that said Letters Patent is hereby corrected as shown below:

COLUMN 59

Line 13, "Close up right margin.
Line 21, "-$L^6$-$L^5$-$L^6$-," should read ---$L^4$-$L^5$-$L^6$-,--
Line 25, "—CH=$R^6$—," should read ---CH=$R^4$—,-- and "$R^6$" should read --$R^4$--.
Line 31, "or substituted or unsubstituted lower" should be deleted.
Line 32, "aralkyl group," should be deleted.

COLUMN 60

Line 24, "formula I;" should read --formula I:--.
Line 30, "$X^+$ should read --$X^+$
         |                        |
         $Y^-$"                   $Y^-$--.
Line 40, "unsubstituted aryl group, substituted or unsub-" should be deleted.
Line 41, "stituted lower" should be deleted.
Line 51, "—CH=$R^4$—," should read ---CH=$R^5$—,--.
Line 55, "$Y^{-=0}$" should read --$Y^-$--.

COLUMN 61

Line 2, "is" should read --which is--.
Line 52, "acid;" should read --acid:--.
Line 59, "$X^+$ should read --$X^+$
         |                        |
         $Y^-$"                   $Y^-$--.
Line 65, Close up right margin.

UNITED STATES PATENT AND TRADEMARK OFFICE
CERTIFICATE OF CORRECTION

PATENT NO. : 5,624,798

DATED : April 29, 1997

INVENTOR(S): NOBUKO YAMAMOTO ET AL.

It is certified that error appears in the above-identified patent and that said Letters Patent is hereby corrected as shown below:

COLUMN 62

Line 9, "—CH=$R^6$—," should read ——CH=$R^4$—,——.
Line 34, "formula VII;" should read ——formula VII:——.
Line 51, "formula VIII" should read ——formula VIII:——.
Line 61, "or X" should read ——or S——.

COLUMN 63

Line 2, "acid;" should read ——acid:——.
Line 9, "$X^+$      should read ——$X^+$
          |                              |
          $Y^-$"                         $Y^-$——.
Line 18, Close up right margin.
Line 45, "robe" should read ——probe——.

COLUMN 64

Line 39, "$X^+$       should read ——$X^+$
          |                              |
          $Y^-$"                         $Y^-$——.
Line 45, Close up right margin.

UNITED STATES PATENT AND TRADEMARK OFFICE
CERTIFICATE OF CORRECTION

PATENT NO. : 5,624,798

DATED : April 29, 1997

INVENTOR(S) : NOBUKO YAMAMOTO ET AL.

It is certified that error appears in the above-identified patent and that said Letters Patent is hereby corrected as shown below:

COLUMN 65

Line 8, "The" should read --A--.
Line 20, "$X^+$" should read --$X^+$
$|$
$Y^-$"     $Y^-$--.
Line 28, Close up right margin.
Line 62, "The" should read --A--.
Line 65, "double-strand" should read --double stranded--.

COLUMN 66

Line 6, "$X^+$" should read --$X^+$
$|$
$Y^-$"     $Y^-$--.
Line 13, Close up right margin.

COLUMN 67

Line 34, "acid;" should read --acid:--.

UNITED STATES PATENT AND TRADEMARK OFFICE
CERTIFICATE OF CORRECTION

PATENT NO. : 5,624,798
DATED : April 29, 1997
INVENTOR(S) : NOBUKO YAMAMOTO ET AL.

It is certified that error appears in the above-identified patent and that said Letters Patent is hereby corrected as shown below:

<u>COLUMN 68</u>

Line 3, "$R^3$," should read --$R^3$--.

Signed and Sealed this

Eleventh Day of November, 1997

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA"

( x i ) SEQUENCE DESCRIPTION: SEQ ID NO:1:

GTTGTAAAAC GACGGCCAGT                                    20

( 2 ) INFORMATION FOR SEQ ID NO:2:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA"

( x i ) SEQUENCE DESCRIPTION: SEQ ID NO:2:

CTCACAGGTA TAGCTGTTAT GTCGTTCATA                         30

( 2 ) INFORMATION FOR SEQ ID NO:3:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA"

( x i ) SEQUENCE DESCRIPTION: SEQ ID NO:3:

AGAGTTTGAT CCTGGCTCAG                                    20

( 2 ) INFORMATION FOR SEQ ID NO:4:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: /desc = "SYNTHETIC DNA"

( x i ) SEQUENCE DESCRIPTION: SEQ ID NO:4:

AACCCAACAT CTCACGACAC                                    20